(12) United States Patent
Yamanoi et al.

(10) Patent No.: US 8,975,263 B2
(45) Date of Patent: Mar. 10, 2015

(54) PHENYLXANTHENE DERIVATIVES

(71) Applicant: Daiichi Sankyo Company, Limited, Tokyo (JP)

(72) Inventors: Shigeo Yamanoi, Tokyo (JP); Katsuji Kagechika, Tokyo (JP); Tsuyoshi Soneda, Tokyo (JP); Yuichi Ochiai, Tokyo (JP); Hidenori Namiki, Tokyo (JP); Fuminao Doi, Tokyo (JP); Madoka Hoshino, Tokyo (JP); Shoko Yoshida, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 14/291,860

(22) Filed: May 30, 2014

(65) Prior Publication Data

US 2014/0343052 A1 Nov. 20, 2014

Related U.S. Application Data

(63) Continuation of application No. PCT/JP2014/056349, filed on Mar. 11, 2014.

(30) Foreign Application Priority Data

Mar. 12, 2013 (JP) .................................. 2013-049428

(51) Int. Cl.
C07D 405/10 (2006.01)
C07D 405/14 (2006.01)
C07D 413/14 (2006.01)

(52) U.S. Cl.
CPC ............ C07D 405/10 (2013.01); C07D 405/14 (2013.01); C07D 413/14 (2013.01)
USPC ........... 514/256; 514/307; 514/337; 544/333; 546/144; 546/283.1

(58) Field of Classification Search
USPC ............... 514/256, 307, 337; 546/144, 283.1; 544/333
See application file for complete search history.

(56) References Cited

U.S. PATENT DOCUMENTS 5,969,139 A 10/1999 Martin et al.
2010/0075926 A1 3/2010 Tsai et al.
2013/0108568 A1 5/2013 Poigny et al.

FOREIGN PATENT DOCUMENTS

WO WO 2010/011318 1/2010

OTHER PUBLICATIONS

Mulakayala et al., "Catalysis by molecular iodine: A rapid synthesis of 1,8-dioxo-octahydroxanthenes and their evaluation as potential anticancer agents," *Bioorganic & Medicinal Chemistry Letters*, (2012), 22:2186-2191.
Nagarujan et al., "Synthesis and oral hypoglycemic properties of 3-(1-oxo-3-hydroxy-2-cyclohexen-2-yl)-4-oxo-4,5,6,7-tetrahydroindoles," *Indian Journal of Chemistry*, (1989), 28B:326-332.

*Primary Examiner* — Kahsay Habte
(74) *Attorney, Agent, or Firm* — Dorsey and Whitney LLP

(57) ABSTRACT

The present invention relates to a compound or a pharmacologically acceptable salt thereof having an excellent glucose lowering effect.

A compound represented by the following general formula (I) or a pharmacologically acceptable salt thereof:

[Formula 1]

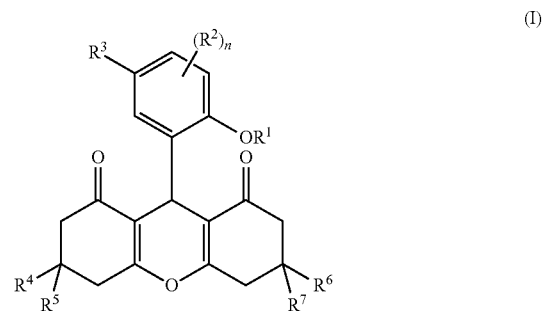

wherein $R^1$ represents a C1-C3 alkyl group, each substituent $R^2$ may be the same or different and may each represent a C1-C3 alkyl group, $R^3$ represents an optionally substituted pyridyl group or the like, $R^4$ and $R^5$, which are the same or different, each represent a C1-C3 alkyl group, $R^6$ and $R^7$, which are the same or different, each represent a C1-C3 alkyl group, and n represents 0 to 3.

28 Claims, No Drawings

PHENYLXANTHENE DERIVATIVES

This application claims the benefit under 35 U.S.C. §111(a) as a continuation application of International Application No. PCT/JP2014/056349, filed Mar. 11, 2014, entitled "Phenylxanthene Derivative," which claims priority to Japanese Patent Application No. 2013-049428, filed Mar. 12, 2013.

TECHNICAL FIELD

The present invention relates to a novel compound, which has a glucose lowering effect and the like and is useful as a therapeutic agent and/or a prophylactic agent for diabetes and the like, and a pharmacologically acceptable salt thereof.

The present invention relates to a therapeutic agent and/or a prophylactic agent for diabetes (type I diabetes, type II diabetes, gestational diabetes, etc.), postprandial hyperglycemia, impaired glucose tolerance, diabetic neuropathy, diabetic nephropathy, diabetic retinopathy, hyperlipidemia, arteriosclerosis, thrombotic disease, adiposity, hypertension, edema, insulin resistance, brittle diabetes, insulinoma, hyperinsulinemia and the like (preferably, a therapeutic agent and/or a prophylactic agent for diabetes), wherein the therapeutic agent and/or the prophylactic agent comprise(s) the above described compound or a pharmacologically acceptable salt thereof as an active ingredient.

Moreover, the present invention relates to a composition for the treatment or prophylaxis of the aforementioned diseases, which comprises the above described compound as an active ingredient, use of the above described compound for manufacture of a medicament for the treatment or prophylaxis of the aforementioned diseases, or a method for the treatment or prophylaxis of the aforementioned diseases, which comprises administering a pharmacologically effective amount of the above described compound to a mammal (preferably, a human).

BACKGROUND ART

Diabetes is a disease that has a chronic hyperglycemic condition as a cardinal symptom, and this disease is developed due to absolute or relative deficiency in insulin action. In clinical sites, diabetes is broadly classified into insulin dependent diabetes (type I diabetes) and non-insulin dependent diabetes (type II diabetes) based on its characteristics.

At present, the treatment of diabetes basically includes diet therapy and exercise therapy. When the blood glucose level cannot be controlled only by these therapies, a drug is administered. Hence, it is desired to develop a more safe and highly effective drug.

Patent Reference 1 discloses a compound, which has a partial structure that is partially the same as that of the compound of the present invention and which has therapeutic and prophylactic effects on infections provoked by simple herpes viruses.

CITATION LIST

Patent References

[Patent Reference 1] International Publication No. WO2010/011318 (corresponding to U.S. Pat. Nos. 6,162,918 and 5,969,139)

SUMMARY OF INVENTION

Technical Problem

As a result of intensive studies, the present inventors have found that a compound represented by formula (I) as shown below has really excellent activity such as glucose lowering activity because of its specific chemical structure, and it also has excellent physical properties as a pharmaceutical agent, such as stability, so that it can become a safe and useful medicament as a prophylactic and/or therapeutic agent for hyperglycemia, diabetes, and pathological conditions or diseases associated with these diseases. Based on these findings, the present inventors have achieved the present invention.

That is to say, a compound of the present invention has a glucose lowering effect and the like and is useful as a prophylactic and/or therapeutic agent for diseases such as diabetes (type I diabetes, type II diabetes, gestational diabetes, etc.), postprandial hyperglycemia, impaired glucose tolerance, diabetic neuropathy, diabetic nephropathy, diabetic retinopathy, hyperlipidemia, arteriosclerosis, thrombotic disease, adiposity, hypertension, edema, insulin resistance, brittle diabetes, insulinoma, and hyperinsulinemia, and in particular, for type II diabetes.

Solution to Problem

The present invention provides:
(1) A compound represented by the following general formula (I) or a pharmacologically acceptable salt thereof:

[Formula 1]

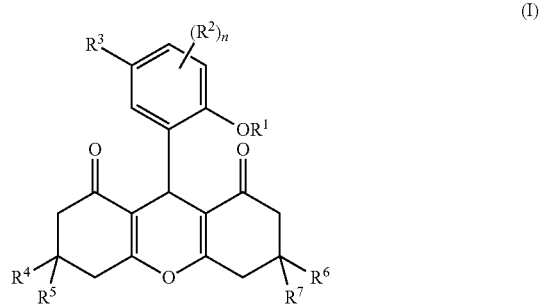

(I)

wherein
R$^1$ represents a C1-C3 alkyl group,
each substituent R$^2$ may be the same or different and may each represent C1-C3 alkyl group, R$^3$ represents a pyridyl group (wherein the pyridyl group may be optionally substituted with 1 to 4 substituents, which may be the same or different, selected from substituent group α), a 5,6,7,8-tetrahydroisoquinolyl group (wherein the 5,6,7,8-tetrahydroisoquinolyl group may be optionally substituted with 1 to 4 substituents, which may be the same or different, selected from substituent group α), or a pyrimidinyl group (wherein the pyrimidinyl group may be optionally substituted with 1 to 3 substituents, which may be the same or different, selected from substituent group α),
R$^4$ and R$^5$ may be the same or different and may each represent a C1-C3 alkyl group,
R$^6$ and R$^7$ may be the same or different and may each represent a C1-C3 alkyl group, and
n represents an integer selected from 0 to 3,
(substituent group α)
a C1-C3 alkyl group, a C2-C3 alkynyl group, a C1-C3 alkoxy group (wherein the C1-C3 alkoxy group may be optionally monosubstituted with a C6-C10 aryl group or a C1-C3 alkoxy group), a hydroxy C1-C3 alkyl group, a carbamoyl group (wherein the carbamoyl group may be optionally monosubstituted with a C1-C3 alkylsulfonyl group optionally monosubstituted with a C1-C3 alkoxy group, or with a hydroxy C1-C3 alkyl group), a 3- to 10-membered heterocyclic group containing 1 to 4 heteroatoms, which may be the same or different, selected from nitrogen, oxygen, and sulfur (wherein the 3- to 10-membered heterocyclic group may be optionally monosubstituted with a carbamoyl group or a carboxyl group), a 3- to 10-membered heterocyclic carbonyl group containing 1 to 4 heteroatoms, which may be the same or different, selected from nitrogen, oxygen, and sulfur, an amino group (wherein the amino group may be optionally monosubstituted with a C1-C3 alkylsulfonyl group, a C1-C3 alkylcarbonyl group, or a carboxy C1-C3 alkyl group), a ureido group (wherein the ureido group may be optionally monosubstituted with a hydroxy C1-C3 alkyl group), an aminosulfonyl group (wherein the aminosulfonyl group may be optionally monosubstituted with a C1-C3 alkylcarbonyl group), a halogen atom, a carboxyl group, a hydroxyl group, and a cyano group;

(2) A compound according to (1) or a pharmacologically acceptable salt thereof, wherein $R^1$ represents a methyl group;

(3) A compound according to (1) or (2), or a pharmacologically acceptable salt thereof, wherein $R^2$ represents a methyl group;

(4) A compound according to any one of (1) to (3) or a pharmacologically acceptable salt thereof, wherein $R^4$, $R^5$, $R^6$, and $R^7$ each represent a methyl group;

(5) A compound represented by the following general formula (IA) or a pharmacologically acceptable salt thereof:

[Formula 2]

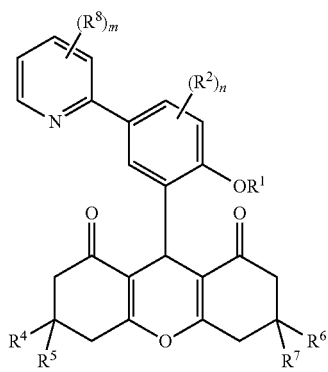

(IA)

wherein
$R^1$ represents a C1-C3 alkyl group, each substituent $R^2$ may be the same or different and may each represent C1-C3 alkyl group, $R^4$ and $R^5$ may be the same or different and may each represent a C1-C3 alkyl group, $R^6$ and $R^7$ may be the same or different and may each represent a C1-C3 alkyl group, each substituent $R^8$ may be the same or different and may each be selected from substituent group α, m represents an integer selected from 0 to 4, and n represents an integer selected from 0 to 3, (substituent group α)

a C1-C3 alkyl group, a C2-C3 alkynyl group, a C1-C3 alkoxy group (wherein the C1-C3 alkoxy group may be optionally monosubstituted with a C6-C10 aryl group or a C1-C3 alkoxy group), a hydroxy C1-C3 alkyl group, a carbamoyl group (wherein the carbamoyl group may be optionally monosubstituted with a C1-C3 alkylsulfonyl group optionally monosubstituted with a C1-C3 alkoxy group, or with a hydroxy C1-C3 alkyl group), a 3- to 10-membered heterocyclic group containing 1 to 4 heteroatoms, which may be the same or different, selected from nitrogen, oxygen, and sulfur (wherein the 3- to 10-membered heterocyclic group may be optionally monosubstituted with a carbamoyl group or a carboxyl group), a 3- to 10-membered heterocyclic carbonyl group containing 1 to 4 heteroatoms, which may be the same or different, selected from nitrogen, oxygen, and sulfur, an amino group (wherein the amino group may be optionally monosubstituted with a C1-C3 alkylsulfonyl group, a C1-C3 alkylcarbonyl group, or a carboxy C1-C3 alkyl group), a ureido group (wherein the ureido group may be optionally monosubstituted with a hydroxy C1-C3 alkyl group), an aminosulfonyl group (wherein the aminosulfonyl group may be optionally monosubstituted with a C1-C3 alkylcarbonyl group), a halogen atom, a carboxyl group, a hydroxyl group, and a cyano group;

(6) A compound according to (5) or a pharmacologically acceptable salt thereof, wherein $R^1$, $R^2$, $R^4$, $R^5$, $R^6$, and $R^7$ each represent a methyl group;

(7) A compound represented by the following general formula (II) or a pharmacologically acceptable salt thereof:

[Formula 3]

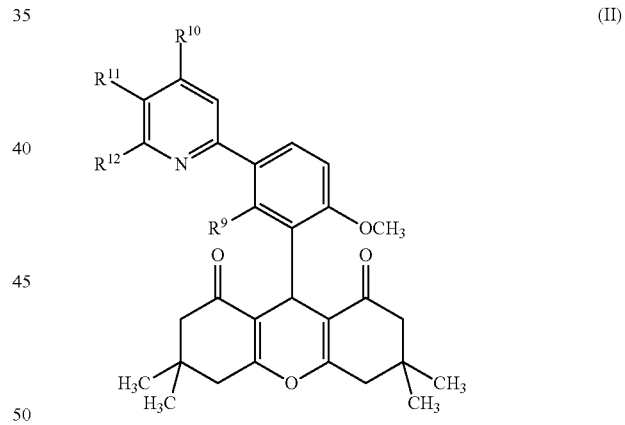

(II)

wherein $R^9$ represents a hydrogen atom or a C1-C3 alkyl group, $R^{10}$ represents a hydrogen atom or a C1-C3 alkyl group, $R^{11}$ represents a hydrogen atom, a C1-C3 alkyl group, or a C2-C3 alkynyl group, $R^{12}$ represents a hydroxy C1-C3 alkyl group, a carbamoyl group (wherein the carbamoyl group may be optionally monosubstituted with a C1-C3 alkylsulfonyl group optionally monosubstituted with a C1-C3 alkoxy group, or with a hydroxy C1-C3 alkyl group), a 3- to 10-membered heterocyclic group containing 1 to 4 heteroatoms, which may be the same or different, selected from nitrogen, oxygen, and sulfur (wherein the 3- to 10-membered heterocyclic group may be optionally monosubstituted with a carbamoyl group or a carboxyl group), a 3- to 10-membered heterocyclic carbonyl group containing 1 to 4 heteroatoms, which may be the same or different, selected from nitrogen, oxygen, and sulfur, a carboxyl group, or a cyano group;

(8) A compound according to (7) or a pharmacologically acceptable salt thereof, wherein $R^9$ represents a methyl group;

(9) A compound according to (7) or (8), or a pharmacologically acceptable salt thereof, wherein $R^{10}$ represents a hydrogen atom or a methyl group;

(9-1) A compound according to (7) or (8), or a pharmacologically acceptable salt thereof, wherein $R^{10}$ represents a hydrogen atom;

(9-2) A compound according to (7) or (8), or a pharmacologically acceptable salt thereof, wherein $R^{10}$ represents a methyl group;

(10) A compound according to any one of (7) to (9), or a pharmacologically acceptable salt thereof, wherein $R^{11}$ represents a hydrogen atom or a methyl group;

(10-1) A compound according to any one of (7) to (9), or a pharmacologically acceptable salt thereof, wherein $R^{11}$ represents a hydrogen atom;

(10-2) A compound according to any one of (7) to (9), or a pharmacologically acceptable salt thereof, wherein $R^{11}$ represents a methyl group;

(11) A compound according to any one of (7) to (10), or a pharmacologically acceptable salt thereof, wherein $R^{12}$ represents a carbamoyl group (wherein the carbamoyl group may be optionally monosubstituted with a C1-C3 alkylsulfonyl group) or a carboxyl group;

(11-1) A compound according to any one of (7) to (10) or a pharmacologically acceptable salt thereof, wherein $R^{12}$ represents a carbamoyl group monosubstituted with a methylsulfonyl group;

(11-2) A compound according to any one of (7) to (10) or a pharmacologically acceptable salt thereof, wherein $R^{12}$ represents a carboxyl group;

Examples of a compound according to (7) or a pharmacologically acceptable salt thereof include the following compounds, the compounds according to (12) to (22) below, and pharmacologically acceptable salts thereof:

6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid, 3-ethyl-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid, 6-[4-methoxy-2-methyl-3-(3,3,6,6-tetramethyl-1,8-dioxo-2,3,4,5,6,7,8,9-octahydro-1H-xanthen-9-yl)phenyl]-3-methylpyridine-2-carboxylic acid, and 6-[4-methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide;

(12) 6-[4-Methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid represented by the following formula:

[Formula 4]

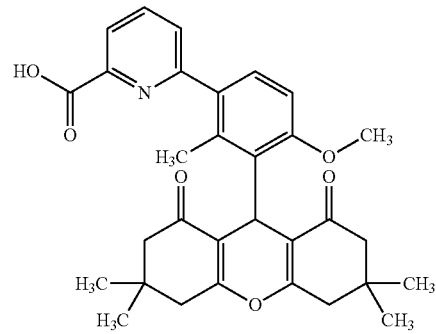

(13) 3-Ethyl-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid represented by the following formula:

[Formula 5]

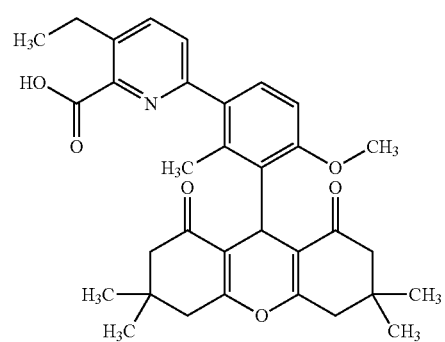

(14) 6-[4-Methoxy-2-methyl-3-(3,3,6,6-tetramethyl-1,8-dioxo-2,3,4,5,6,7,8,9-octahydro-1H-xanthen-9-yl)phenyl]-3-methylpyridine-2-carboxylic acid represented by the following formula:

[Formula 6]

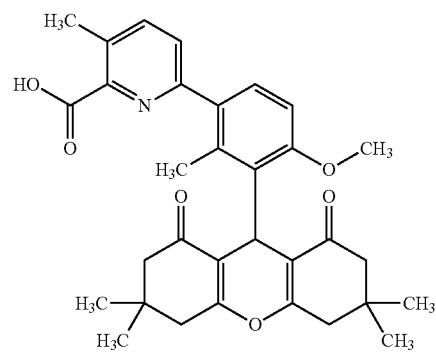

(15) 6-[4-Methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide represented by the following formula:

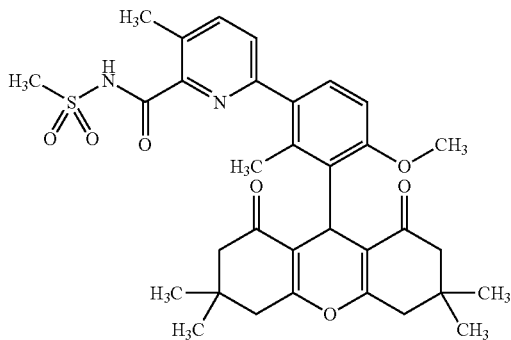

(16) 6-[4-Methoxy-2-methyl-3-(3,3,6,6-tetramethyl-1,8-dioxo-2,3,4,5,6,7,8,9-octahydro-1H-xanthen-9-yl)phenyl]-4-methylpyridine-2-carboxylic acid represented by the following formula:

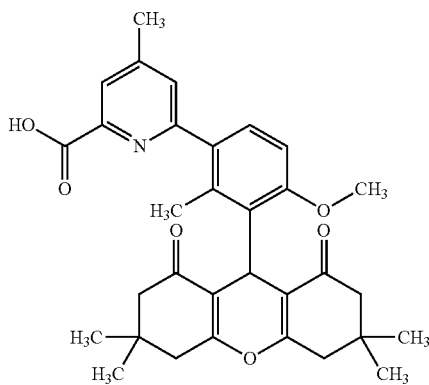 [SMILES: COc1ccc(-c2cc(C)cc(C(=O)O)n2)c(C)c1C1C2=C(CC(C)(C)CC2=O)OC2=C1C(=O)CC(C)(C)C2]

(17) 6-[4-Methoxy-2-methyl-3-(3,3,6,6-tetramethyl-1,8-dioxo-2,3,4,5,6,7,8,9-octahydro-1H-xanthen-9-yl)phenyl]-4-methyl-N-(methylsulfonyl)pyridine-2-carboxamide represented by the following formula:

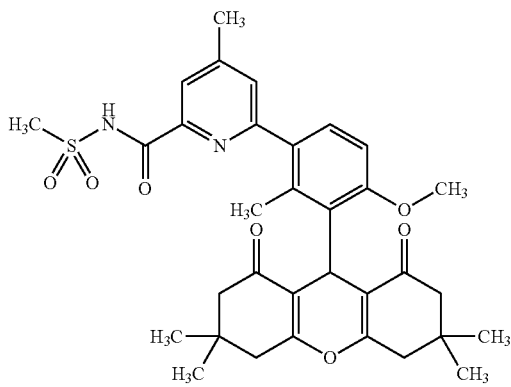

(18) A pharmacologically acceptable salt of a compound according to any one of (12) to (17);

(19) An alkali metal salt or an alkaline-earth metal salt of a compound according to any one of (12) to (17);

(20) A hemi-calcium salt of a compound according to any one of (12) to (17), such as the following compounds (20-1) to (20-6):

(20-1) 6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid hemi-calcium salt;

(20-2) 3-ethyl-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid hemi-calcium salt;

(20-3) 6-[4-methoxy-2-methyl-3-(3,3,6,6-tetramethyl-1,8-dioxo-2,3,4,5,6,7,8,9-octahydro-1H-xanthen-9-yl)phenyl]-3-methylpyridine-2-carboxylic acid hemi-calcium salt;

(20-4) 6-[4-methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide hemi-calcium salt;

(20-5) 6-[4-methoxy-2-methyl-3-(3,3,6,6-tetramethyl-1,8-dioxo-2,3,4,5,6,7,8,9-octahydro-1H-xanthen-9-yl)phenyl]-4-methylpyridine-2-carboxylic acid hemi-calcium salt;

(20-6) 6-[4-methoxy-2-methyl-3-(3,3,6,6-tetramethyl-1,8-dioxo-2,3,4,5,6,7,8,9-octahydro-1H-xanthen-9-yl)phenyl]-4-methyl-N-(methylsulfonyl)pyridine-2-carboxamide hemi-calcium salt;

(21) A sodium salt of the compound according to any one of (12) to (17), such as the following compounds (21-1) to (21-6):

(21-1) 6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid sodium salt;

(21-2) 3-ethyl-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid sodium salt;

(21-3) 6-[4-methoxy-2-methyl-3-(3,3,6,6-tetramethyl-1,8-dioxo-2,3,4,5,6,7,8,9-octahydro-1H-xanthen-9-yl)phenyl]-3-methylpyridine-2-carboxylic acid sodium salt;

(21-4) 6-[4-methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide sodium salt;

(21-5) 6-[4-methoxy-2-methyl-3-(3,3,6,6-tetramethyl-1,8-dioxo-2,3,4,5,6,7,8,9-octahydro-1H-xanthen-9-yl)phenyl]-4-methylpyridine-2-carboxylic acid sodium salt;

(21-6) 6-[4-methoxy-2-methyl-3-(3,3,6,6-tetramethyl-1,8-dioxo-2,3,4,5,6,7,8,9-octahydro-1H-xanthen-9-yl)phenyl]-4-methyl-N-(methylsulfonyl)pyridine-2-carboxamide sodium salt;

(22) A 2-methylpropan-2-amine salt of the compound according to any one of (12) to (17), such as the following compounds (22-1) to (22-6):

(22-1) 6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid 2-methylpropane-2-amine salt;

(22-2) 3-ethyl-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid 2-methylpropane-2-amine salt;

(22-3) 6-[4-methoxy-2-methyl-3-(3,3,6,6-tetramethyl-1,8-dioxo-2,3,4,5,6,7,8,9-octahydro-1H-xanthen-9-yl)phenyl]-3-methylpyridine-2-carboxylic acid 2-methylpropane-2-amine salt;

(22-4) 6-[4-methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide 2-methylpropane-2-amine salt;

(22-5) 6-[4-methoxy-2-methyl-3-(3,3,6,6-tetramethyl-1,8-dioxo-2,3,4,5,6,7,8,9-octahydro-1H-xanthen-9-yl)phenyl]-4-methylpyridine-2-carboxylic acid 2-methylpropane-2-amine salt;

(22-6) 6-[4-methoxy-2-methyl-3-(3,3,6,6-tetramethyl-1,8-dioxo-2,3,4,5,6,7,8,9-octahydro-1H-xanthen-9-yl)phenyl]-4-methyl-N-(methylsulfonyl)pyridine-2-carboxamide 2-methylpropane-2-amine salt;

(23) A glucose lowering agent comprising, as an active ingredient, a compound according to any one of (1) to (22) or a pharmacologically acceptable salt thereof;

(24) A medicament comprising, as an active ingredient, a compound according to any one of (1) to (22) or a pharmacologically acceptable salt thereof;

(24-1) A medicament according to (24) for the treatment or prophylaxis of diabetes, postprandial hyperglycemia, impaired glucose tolerance, diabetic neuropathy, diabetic nephropathy, diabetic retinopathy, hyperlipidemia, arteriosclerosis, thrombotic disease, adiposity, hypertension, edema, insulin resistance, brittle diabetes, insulinoma, or hyperinsulinemia;

(25) A medicament according to (24) for the treatment or prophylaxis of diabetes, postprandial hyperglycemia, impaired glucose tolerance, or insulin resistance;

(26) A medicament according to (24) for the treatment of diabetes, postprandial hyperglycemia, impaired glucose tolerance, or insulin resistance;

(26-1) A medicament according to (24) for the treatment of diabetes or postprandial hyperglycemia;

(27) A medicament according to (24) for the treatment of type II diabetes;

(28) Use of a compound according to any one of (1) to (22) or a pharmacologically acceptable salt thereof for manufacturing a pharmaceutical composition;

(29) A method for treating type II diabetes, which comprises administering a pharmacologically effective amount of a compound according to any one of (1) to (22) or a pharmacologically acceptable salt thereof to a warm-blooded animal; and

(30) A method for the treatment or prophylaxis of type II diabetes, which comprises administering a pharmacologically effective amount of a compound according to any one of (1) to (22) or a pharmacologically acceptable salt thereof to a warm-blooded animal.

In the present invention, the term "C1-C3 alkyl group" means a linear or branched alkyl group containing 1 to 3 carbon atoms. Examples of a C1-C3 alkyl group include methyl, ethyl, n-propyl, and isopropyl groups. The C1-C3 alkyl group is preferably a methyl or ethyl group in $R^1, R^2, R^4, R^5, R^6, R^7, R^8, R^9, R^{10}, R^{11}$, and the substituent group α.

In the present invention, the term "hydroxy C1-C3 alkyl group" means a group in which the above described "C1-C3 alkyl group" is substituted with a hydroxyl group. Examples of a hydroxy C1-C3 alkyl group include hydroxymethyl, 1-hydroxyethyl, 2-hydroxyethyl, and 3-hydroxypropyl groups. The hydroxy C1-C3 alkyl group is preferably a hydroxymethyl group or 1-hydroxyethyl group in $R^8, R^{12}$, the substituent group α, a substituent for the "carbamoyl group" in the substituent group α and $R^{12}$, and a substituent for the "ureido group" in the substituent group α.

In the present invention, the term "C1-C3 alkoxy group" means a group in which the above described "C1-C3 alkyl group" binds to an oxygen atom. Examples of a C1-C3 alkoxy group include linear or branched alkoxy groups containing 1 to 3 carbon atoms, such as a methoxy, ethoxy, n-propoxy, or isopropoxy group. The C1-C3 alkoxy group is preferably a methoxy or ethoxy group in $R^8$, the substituent group α, a substituent for the "C1-C3 alkoxy group" in the substituent group α, and a substituent for the "carbamoyl group" in the substituent group α and $R^{12}$.

In the present invention, the term "C2-C3 alkynyl group" means a linear or branched alkynyl group containing 2 or 3 carbon atoms. Examples of a C2-C3 alkynyl group include ethynyl and prop-2-yn-1-yl groups. The C2-C3 alkynyl group is preferably an ethynyl group in $R^8, R^{11}$, and the substituent group α.

In the present invention, the term "C6-C10 aryl group" means an aromatic hydrocarbon group containing 6 to 10 carbon atoms. Examples of a C6-C10 aryl group include phenyl, indenyl, and naphthyl groups. The C6-C10 aryl group is preferably a phenyl group in a substituent for the C1-C3 alkoxy group in the substituent group α.

In the present invention, the term "3- to 10-membered heterocyclic group containing 1 to 4 heteroatoms, which may be the same or different, selected from nitrogen, oxygen, and sulfur" means a 3- to 10-membered heterocyclic group containing 1 to 4 nitrogen, oxygen, or sulfur atoms. Examples of a 3- to 10-membered heterocyclic group containing one to four heteroatoms, which may be the same or different, selected from nitrogen, oxygen, and sulfur include: aromatic heterocyclic groups such as furyl, thienyl, pyrrolyl, azepinyl, pyrazolyl, imidazolyl, oxazolyl, oxadiazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, or pyrazinyl; and partially or completely reduced groups corresponding to the aforementioned groups, such as oxetanyl, morpholinyl, thiomorpholinyl, pyrrolidinyl, pyrrolinyl, imidazolidinyl, imidazolinyl, pyrazolidinyl, pyrazolinyl, piperidinyl, piperazinyl, tetrahydrofuranyl, tetrahydropyranyl, or 5-oxo-4,5-dihydro-1,2,4-oxadiazolyl. It is to be noted that the above described "3- to 10-membered heterocyclic group" may be condensed with another cyclic group. Examples include benzofuranyl, chromenyl, indolizinyl, isoindolyl, indolyl, indazolyl, purinyl, quinolizinyl, isoquinolyl, quinolyl, phthalazinyl, naphthylidinyl, quinoxalinyl, quinazolinyl, isoindolinyl, 2,3-dihydro-1-benzofuranyl, 3,4-dihydro-1H-isochromenyl, 1,2,3,4-tetrahydroquinolinyl, and 1,2,3,4-tetrahydroisoquinolinyl groups. Examples of the above-mentioned 3- to 10-membered heterocyclic group preferably used in the substituent group α include triazolyl, tetrazolyl, morpholinyl, pyrrolidinyl, piperidinyl, and 5-oxo-4,5-dihydro-1,2,4-oxadiazolyl groups.

In the present invention, the term "3- to 10-membered heterocyclic carbonyl group containing 1 to 4 heteroatoms, which may be the same or different, selected from nitrogen, oxygen, and sulfur" means a group in which the above described "3- to 10-membered heterocyclic group containing 1 to 4 heteroatoms, which may be the same or different, selected from nitrogen, oxygen, and sulfur" binds to a carbonyl group. Examples of a 3- to 10-membered heterocyclic carbonyl group containing one to four heteroatoms, which may be the same or different, selected from nitrogen, oxygen, and sulfur include pyridylcarbonyl, oxetanylcarbonyl, morpholinylcarbonyl, piperidinylcarbonyl, and tetrahydrofuranylcarbonyl groups. The 3- to 10-membered heterocyclic carbonyl group containing one to four heteroatoms, which may be the same or different, selected from nitrogen, oxygen, and sulfur is preferably a morpholinylcarbonyl group in the substituent group α.

In the present invention, the term "C1-C3 alkylcarbonyl group" means a group in which the above described "C1-C3 alkyl group" binds to a carbonyl group. Examples of a C1-C3 alkylcarbonyl group include linear or branched alkoxycarbonyl groups containing 1 to 3 carbon atoms, such as an acetyl, propionyl, n-propylcarbonyl, and isopropylcarbonyl group.

The C1-C3 alkylcarbonyl group is preferably an acetyl or propionyl group in a substituent for the "amino group" in the substituent group α, and in a substituent for the "aminosulfonyl group" in the substituent group α.

In the present invention, the term "C1-C3 alkylsulfonyl group" means a group to which the above described "C1-3 alkyl group" binds via a sulfonyl group. Examples of a C1-C3 alkylsulfonyl group include methanesulfonyl, ethanesulfonyl, n-propanesulfonyl, and isopropanesulfonyl groups. The C1-C3 alkylsulfonyl group is preferably a methanesulfonyl group in a substituent for the "carbamoyl group" in the substituent group α and $R^{12}$, and in a substituent for the "amino group" in the substituent group α.

In the present invention, the term "carboxy C1-C3 alkyl group" means a group in which carboxylic acid binds to the above described "C1-3 alkyl group." Examples of a carboxy C1-C3 alkyl group include ethanoic acid, propanoic acid, or butanoic acid. The carboxy C1-C3 alkyl group is preferably ethanoic acid in a substituent for the "amino group" in the substituent group α.

In the present invention, the term "halogen atom" means a fluorine atom, a chlorine atom, a bromine atom, or an iodine atom. The halogen atom is preferably a chlorine atom or a fluorine atom in $R^8$ and the substituent group α.

In the present invention, the term "pharmacologically acceptable salt" means a salt that can be formed by reacting a compound with an acid, when the compound has a basic group such as an amino group; or by reacting a compound with a base, when the compound has an acidic group such as a carboxyl group.

Preferred examples of the salt based on a basic group include: inorganic acid salts, such as hydrohalic acid salts including hydrofluoric acid salts, hydrochloric acid salts, hydrobromic acid salts, and hydroiodic acid salts, nitrates, perchlorates, sulfates, and phosphates; organic acid salts, such as lower alkane sulfonates including methanesulfonates, trifluoromethanesulfonates, and ethanesulfonates, aryl sulfonates including benzensulfonates and p-toluenesulfonates, acetates, malates, fumarates, succinates, citrates, ascorbates, tartrates, oxalates, and maleates; and amino acid salts such as glycine salts, lysine salts, arginine salts, ornithine salts, glutamates, and aspartates. Hydrohaloic salts or inorganic acid salts are preferred.

Preferred examples of the salt based on an acidic group include: metal salts, such as alkali metal salts including sodium salts, potassium salts, and lithium salts, alkaline-earth metal salts including calcium salts and magnesium salts, aluminum salts, and iron salts; amine salts, such as inorganic salts including ammonium salts, and organic salts including 2-methylpropan-2-amine salts, t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts, and tris(hydroxymethyl)aminomethane salts; and amino acid salts such as glycine salts, lysine salts, arginine salts, ornithine salts, glutamates, and aspartates. More preferred examples include sodium salts, calcium salts, and 2-methylpropan-2-amine salts. Particularly preferred examples include hemi-calcium salts and 2-methylpropan-2-amine salts.

The compound represented by the general formula (I) of the present invention or a pharmacologically acceptable salt thereof includes all types of isomers (keto-enol isomers, stereoisomers, etc.)

When the compound represented by the general formula (I) of the present invention or a pharmacologically acceptable salt thereof has an asymmetric carbon atom in a molecule thereof, it has various isomers. In the compound of the present invention, these isomers and mixtures of these isomers are all represented by a single formula, namely, the general formula (I). Accordingly, the present invention includes all of these isomers and mixtures comprising these isomers in any given ratio.

The above-mentioned stereoisomer can be obtained by isolating the synthesized compound according to the present invention using an ordinary optical resolution method or separation method, as desired.

The compound represented by the general formula (I) of the present invention or a pharmacologically acceptable salt thereof may also contain atomic isotopes at a non-natural rate, in addition to one or more atoms constituting the compound. Examples of such an atomic isotope include deuterium ($^2$H), tritium ($^3$H), iodine-125 ($^{125}$I), and carbon-14 ($^{14}$C). In addition, the above described compound can be radiolabeled with radioisotopes such as tritium ($^3$H), iodine-125 ($^{125}$I), or carbon-14 ($^{14}$C). The radiolabeled compound is useful as a therapeutic or prophylactic agent, or a reagent used for studies, e.g., an assay reagent, or a diagnostic agent, e.g., an in vivo diagnostic imaging agent. All of the isotopic variants of the compound of the present invention are included in the scope of the present invention, regardless of whether or not they are radioactive.

When the compound represented by the general formula (I) of the present invention or a pharmacologically acceptable salt thereof is left in the air or is recrystallized, it will absorb water, and as a result, adsorbed water will bind to the compound or it will form a hydrate. Such a hydrate is also included in the salts of the present invention.

There may be a case in which the compound represented by the general formula (I) of the present invention or a pharmacologically acceptable salt thereof will absorb another certain type of solvent, so that it becomes a solvate. Such a solvate is also included in the salts of the present invention.

Furthermore, the present invention includes all compounds, which are metabolized in vivo to the phenylxanthene derivative represented by the above described general formula (I) or a salt thereof (e.g. a derivative in which a carboxylic acid portion of the above described general formula (I) is esterified).

In the present invention, $R^1$ preferably represents a methyl group.

In the present invention, $R^2$ preferably represents a methyl group or a hydrogen atom, and more preferably a methyl group.

In the present invention, $R^3$ preferably represents a pyridyl group (wherein the pyridyl group may be optionally substituted with 1 to 4 substituents, which may be the same or different, selected from the substituent group α).

In the present invention, $R^4$, $R^5$, $R^6$, and $R^7$ each preferably represent a methyl group.

In the present invention, preferably, each substituent $R^8$, which may be the same or different, represents a hydrogen atom, a methyl group, a carbamoyl group (wherein the carbamoyl group may be optionally monosubstituted with a C1-C3 alkylsulfonyl group optionally monosubstituted with a C1-C3 alkoxy group, or with a hydroxy C1-C3 alkyl group), or a carboxyl group.

In the present invention, $R^9$ preferably represents a hydrogen atom or a methyl group, and more preferably a methyl group.

In the present invention, $R^{10}$ preferably represents a hydrogen atom or a methyl group.

In the present invention, $R^{11}$ preferably represents a hydrogen atom or a methyl group.

In the present invention, $R^{12}$ preferably represents a carbamoyl group (wherein the carbamoyl group may be optionally monosubstituted with a C1-C3 alkylsulfonyl group optionally monosubstituted with a C1-C3 alkoxy group, or with a hydroxy C1-C3 alkyl group), or a carboxyl group, and more preferably a carbamoyl group (wherein the carbamoyl group may be optionally monosubstituted with a C1-C3 alkylsulfonyl group optionally monosubstituted with a C1-C3 alkoxy group, or with a hydroxy C1-C3 alkyl group).

In the present invention, m preferably represents 2.

In the present invention, n preferably represents 1.

In the present invention, the substituent group a preferably represents a carbamoyl group (which may be optionally monosubstituted with a C1-C3 alkylsulfonyl group optionally monosubstituted with a C1-C3 alkoxy group, or with a hydroxy C1-C3 alkyl group) in a substituent for the pyridyl group in $R^3$.

In the present invention, the substituent group α preferably represents a carboxyl group in a substituent for the 5,6,7,8-tetrahydroisoquinolyl group in $R^3$.

In the present invention, the substituent group a preferably represents a carbamoyl group (which may be optionally monosubstituted with a C1-C3 alkylsulfonyl group optionally monosubstituted with a C1-C3 alkoxy group, or with a hydroxy C1-C3 alkyl group) or a hydroxy C1-C3 alkyl group in a substituent for the pyrimidinyl group in $R^3$.

The general formula (I) of the present invention is preferably the following formula (IA) or (IB):

[Formula 10]

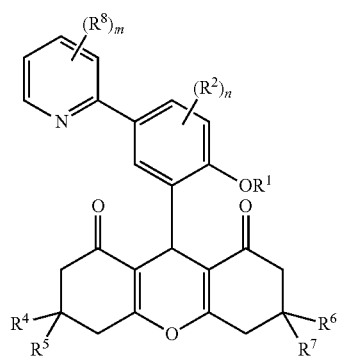

(IA)

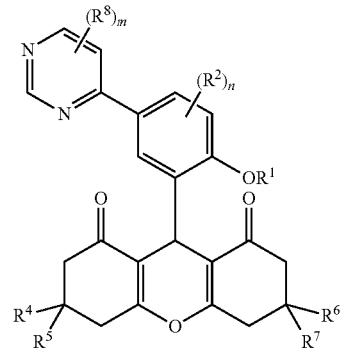

(IB)

wherein $R^8$ represents a group selected from the substituent group α; m represents an integer selected from 0 to 4; and $R^1$, $R^2$, $R^4$, $R^5$, $R^6$, $R^7$, n, and the substituent group α have the same definitions as those described above, and the general formula (I) is more preferably the following general formula (II):

[Formula 11]

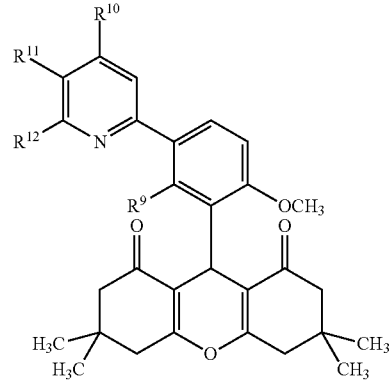

(II)

wherein $R^9$ represents a hydrogen atom or a C1-C3 alkyl group; $R^{10}$ represents a hydrogen atom or a C1-C3 alkyl group; $R^{11}$ represents a hydrogen atom, a C1-C3 alkyl group, or a C2-C3 alkynyl group; $R^{12}$ represents a hydroxy C1-C3 alkyl group, a carbamoyl group (wherein the carbamoyl group may be optionally monosubstituted with a C1-C3 alkylsulfonyl group optionally monosubstituted with a C1-C3 alkoxy group, or with a hydroxy C1-C3 alkyl group), a 3- to 10-membered heterocyclic group containing 1 to 4 heteroatoms, which may be the same or different, selected from nitrogen, oxygen, and sulfur (wherein the 3- to 10-membered heterocyclic group may be optionally monosubstituted with a carbamoyl group or a carboxyl group), a 3- to 10-membered heterocyclic carbonyl group containing 1 to 4 heteroatoms, which may be the same or different, selected from nitrogen, oxygen, and sulfur, a carboxyl group, or a cyano group.

The compound represented by the general formula (I) of the present invention can be produced, for example, by the following method.

Method A:

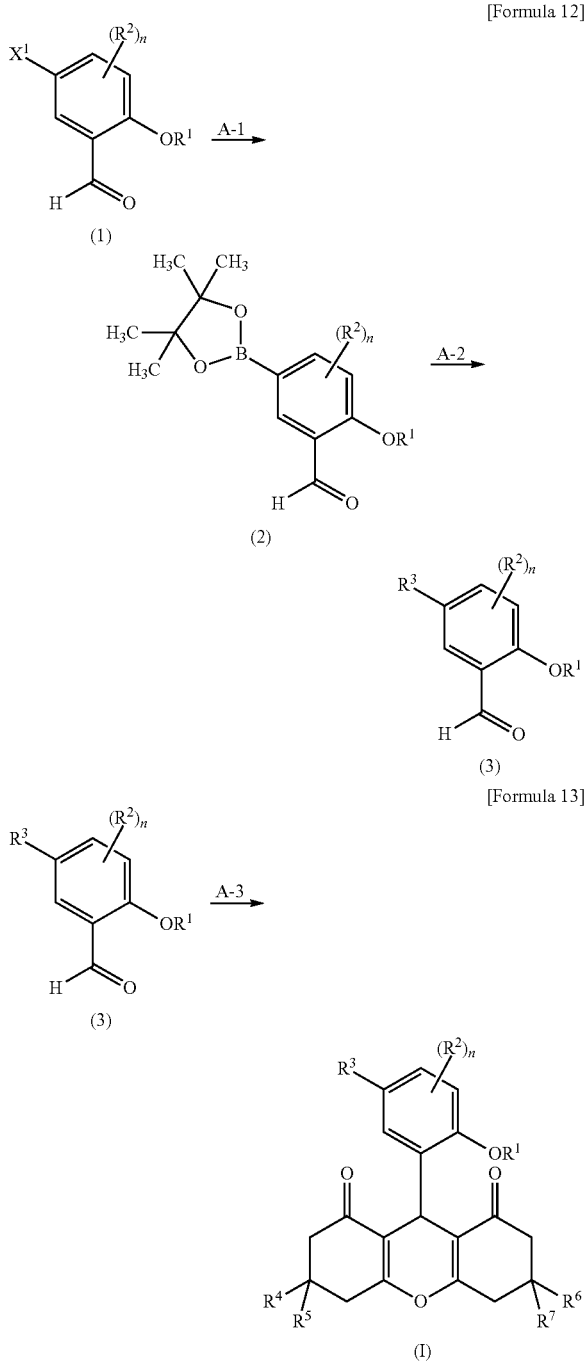

In the above described formulae and the following descriptions, $R^1$, $R^2$, $R^3$, $R^4$, $R^5$, $R^6$, $R^7$, and n have the same definitions as those described above; and $X^1$ represents a halogen atom selected from a fluorine atom, a chlorine atom, a bromine atom, and an iodine atom.

In the above described step and the following descriptions, protection and deprotection of a hydroxyl group, an amino group, and a carboxyl group can be carried out according to an ordinary method used in the field of synthetic organic chemistry, for example, the methods and protective groups described in Greene & Wuts, "Protective Groups in Organic Synthesis," Third Edition, Wiley-Interscience, U.S.A., but the methods and protective groups applicable herein are not limited thereto.

Hereafter, individual steps will be described.

(Method A)

(Step A-1)

The present step is a step of converting the known compound (1) to a boron compound in the presence of a catalyst to produce the intermediate compound (2).

The solvent is not particularly limited, as long as it does not inhibit the reaction and it dissolves the starting material to a certain extent. Examples of the solvent include: amides such as N,N-dimethylformamide, N,N-dimethylacetamide, and N-methylpyrrolidone; sulfoxides such as dimethyl sulfoxide; and ethers such as 1,2-dimethoxyethane, 1,4-dioxane, and tetrahydrofuran. Dimethyl sulfoxide or 1,4-dioxane is preferred.

The boron used as a reagent is preferably bis(pinacolato)diboron.

Preferred examples of the catalyst include palladium complexes including, as typical examples, dichlorobis(triphenylphosphine) palladium(II) and a 1,1'-bis(diphenylphosphino)ferrocene-palladium(II) dichloride-dichloromethane complex. More preferred examples of the catalyst include dichlorobis(triphenylphosphine) palladium(II) and a 1,1'-bis(diphenylphosphino)ferrocene-palladium(II) dichloride-dichloromethane complex.

It is preferred that a metallic acetate including, as a typical example, potassium acetate, or a metallic carbonate including, as a typical example, potassium carbonate, be added as a reagent. Potassium acetate is more preferred.

The reaction temperature is 70° C. to 140° C., and preferably 90° C. to 120° C.

The reaction time is 1 hour to 24 hours, and preferably 5 hours to 8 hours.

(Step A-2)

The present step is a step of subjecting the intermediate compound (2) to a cross-coupling reaction with a halide of $R^3$ to produce the intermediate compound (3).

The solvent is not particularly limited, as long as it does not inhibit the reaction and it dissolves the starting material to a certain extent. Examples of the solvent include: nitriles such as acetonitrile and isobutyronitrile; amides such as N,N-dimethylformamide, N,N-dimethylacetamide, and N-methylpyrrolidone; ethers such as 1,2-dimethoxyethane, 1,4-dioxane, and tetrahydrofuran; and water. Dimethoxyethane or water is preferred.

Preferred examples of the catalyst include palladium complexes including, as a typical example, tetrakis(triphenylphosphine) palladium(0). Tetrakis(triphenylphosphine) palladium(0) is more preferred.

The halide of $R^3$ is preferably a chloride of $R^3$.

It is preferred that a metallic carbonate including, as a typical example, sodium carbonate, or potassium phosphate, be added as a reagent. Sodium carbonate is more preferred.

The reaction temperature is 30° C. to 120° C., and preferably 70° C. to 100° C.

The reaction time is 1 hour to 24 hours, and preferably 3 hours to 8 hours.

(Step A-3)

The present step is a step of constructing a xanthene skeleton on the intermediate compound (3) to produce the phenylxanthene derivative compound (1). The protective group may be removed by performing hydrolysis or the like, as necessary.

The solvent is not particularly limited, as long as it does not inhibit the reaction and it dissolves the starting material to a certain extent. Examples of the solvent include: water; halogenated hydrocarbons such as chloroform; ethers such as dioxane and tetrahydrofuran; and alcohols such as methanol and ethanol. The solvent is preferably ethanol, chloroform, 1,4-dioxane, water, or methanol.

Examples of the acid include dodecylbenzenesulfonic acid, pyrrolidine-p-toluenesulfonic acid monohydrate, and pyrrolidine-2 N or 5 N hydrochloric acid. The acid is preferably pyrrolidine-p-toluenesulfonic acid monohydrate or dodecylbenzenesulfonic acid.

The reaction temperature is 20° C. to 120° C., and preferably 60° C. to 120° C.

The reaction time is 2 hours to 12 hours, and preferably 3.5 hours to 6 hours.

After completion of the reaction in each of the above described steps, the compound of interest is collected from the reaction mixture according to a conventional method. For example, the reaction mixture is appropriately neutralized, or if an insoluble matter is present, it is removed by filtration. Thereafter, immiscible organic solvents, such as water and ethyl acetate, are added to the resultant, and the mixture obtained is then washed with water or the like. Thereafter, an organic layer containing the compound of interest is separated from the resultant, and is then dried over anhydrous magnesium sulfate or the like. The solvent is distilled away so as to obtain the compound of interest.

If necessary, the compound of interest obtained can be separated and purified by performing an appropriate combination of conventional methods such as recrystallization, reprecipitation, or methods commonly used in separation and purification of organic compounds, e.g. methods using a synthetic adsorbent, such as adsorption column chromatography or partition column chromatography, methods using ion exchange chromatography, and normal-phase or reversed-phase chromatography using silica gel or alkylated silica gel, and then performing elution with a suitable eluting agent.

Further, an optically active substance can be separated and purified using a chiral column, as necessary.

The phenylxanthene derivative represented by the above described general formula (I) of the present invention or a pharmacologically acceptable salt thereof is administered in various administration forms. The administration route is not particularly limited, and it is determined depending on the forms of various preparations, the age, sex, and other conditions of a patient, the severity of the disease, etc. For example, a tablet, a pill, a powder preparation, a granule preparation, a syrup preparation, a liquid preparation, a suspension preparation, an emulsion preparation, and a capsule preparation are orally administered. On the other hand, in the case of an injection, the aforementioned phenylxanthene derivative or a pharmacologically acceptable salt thereof is intravenously administered, singly or in the form of a mixture with a common replacement fluid containing glucose, amino acids, or the like. Further, it is singly administered intramuscularly, intracutaneously, subcutaneously, or intraperitoneally, as necessary. In the case of a suppository, it is intrarectally administered. Oral administration is preferred.

Various types of these preparations can be formulated according to conventional methods by adding to the principal agent known auxiliary agents that can be commonly used in the field of known drug preparation, such as an excipient, a binding agent, a disintegrating agent, a lubricant, a solubilizer, a flavoring agent, and a coating agent.

When the present phenylxanthene derivative or a pharmacologically acceptable salt thereof is molded into the form of a tablet, carriers conventionally known in the present field can be broadly used. Examples of the carrier include: excipients such as lactose, saccharose, sodium chloride, glucose, urea, starch, calcium carbonate, kaolin, crystalline cellulose, and silicic acid; binding agents such as water, ethanol, propanol, simple syrup, glucose solution, starch solution, gelatin solution, carboxymethylcellulose, shellac, methylcellulose, potassium phosphate, and polyvinyl pyrrolidone; disintegrating agents such as dry starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, and lactose; disintegration-suppressing agents such as saccharose, stearin, cacao butter, and hydrogenated oil; absorption-promoting agents such as quaternary ammonium bases and sodium lauryl sulfate; moisturizing agents such as glycerin and starch; adsorbents such as starch, lactose, kaolin, bentonite, and colloidal silica; and lubricants such as purified talc, stearate, boric acid powder, and polyethylene glycol. Moreover, the tablet can be processed into tablets coated with a common coating, such as a sugar-coated tablet, a gelatin-coated tablet, an enteric-coated tablet, a film-coated tablet, a double-coated tablet, or a multi-layered tablet.

When the present phenylxanthene derivative or a pharmacologically acceptable salt thereof is molded into the form of a pill, carriers conventionally known in the present field can be broadly used. Examples of the carrier include: excipients such as glucose, lactose, starch, cacao butter, hydrogenated vegetable oil, kaolin, and talc; binding agents such as gum arabic powder, tragacanth powder, gelatin, and ethanol; and disintegrating agents such as laminaran agar.

When the present phenylxanthene derivative or a pharmacologically acceptable salt thereof is molded into the form of a suppository, carriers conventionally known in the present field can be broadly used. Examples of the carrier include polyethylene glycol, cacao butter, higher alcohols, esters of higher alcohols, gelatin, and semisynthetic glycerides.

When the present phenylxanthene derivative or a pharmacologically acceptable salt thereof is prepared as an injection, it is preferred that the liquid agent and the suspension agent be sterilized and be isotonic to the blood. When the present phenylxanthene derivative or a pharmacologically acceptable salt thereof is molded into the form of such a liquid agent, emulsion, or suspension agent, all of the diluents that are commonly used in the present field can be used. Examples of the diluent include water, ethyl alcohol, propylene glycol, ethoxylated isostearyl alcohol, polyoxylated isostearyl alcohol, and polyoxyethylene sorbitan fatty acid esters. In this case, common salt, glucose, or glycerin may be added to the pharmaceutical preparation in an amount sufficient for preparation of an isotonic solution. Also, a common solubilizing agent, buffer, soothing agent, or the like may be added thereto.

Moreover, a coloring agent, a preservative, an aromatic agent, a flavoring agent, a sweetener, and other pharmaceutical agents may be added to the pharmaceutical preparation, as necessary.

The amount of the compound contained as an active ingredient in the above described pharmaceutical preparation is not particularly limited, and it is appropriately selected from a broad range. It is appropriate that the active ingredient compound be contained in the composition at a weight percentage of usually 1% to 70%, and preferably 1% to 30%, based on the total weight of the composition.

The dose applied is different depending on symptoms, age, body weight, administration method, dosage form, and the like. In general, the lower limit of the dose is 0.001 mg/kg (preferably 0.01 mg/kg, and more preferably 0.1 mg/kg) per adult per day, and the upper limit thereof is 200 mg/kg (preferably 20 mg/kg, and more preferably 10 mg/kg) per adult per day. The aforementioned dose can be administered once or divided over several administrations per day.

The compound of the present invention can be used in combination with various therapeutic or prophylactic agents for the above described diseases, for which the present invention is considered to be effective. With regard to this combined use, the present compound and such agents may be administered simultaneously, or separately continuously, or at desired intervals. The simultaneously administered preparations may be either a combination drug, or individual agents that have been formulated separately.

Advantageous Effects of Invention

A phenylxanthene derivative or a pharmacologically acceptable salt thereof, which is a compound of the present invention, has an excellent glucose lowering effect and is useful as a therapeutic agent or a prophylactic agent for diseases such as diabetes (type I diabetes, type II diabetes, gestational diabetes, etc.), postprandial hyperglycemia, impaired glucose tolerance, diabetic neuropathy, diabetic nephropathy, diabetic retinopathy, hyperlipidemia, arteriosclerosis, thrombotic disease, adiposity, hypertension, edema, insulin resistance, brittle diabetes, insulinoma, and hyperinsulinemia. Moreover, since the present compound has low toxicity and is excellent in terms of safety, it can be said that it is extremely useful as a medicament.

DESCRIPTION OF EMBODIMENTS

Hereinafter, the present invention will be described in more detail in the following working examples and the like. However, these working examples are not intended to limit the scope of the present invention.

As silica gel used for columns in the working examples, Silica Gel SK-85 (230 to 400 meshes), Silica Gel SK-34 (70 to 230 meshes), each manufactured by Merck KGaA, or Chromatorex NH (200 to 350 meshes) manufactured by Fuji Silysia Chemical Ltd. was used. In addition to the common column chromatography, the automatic chromatographic apparatus (SP-1) manufactured by Biotage AB, the automatic chromatographic apparatus (Parallel Frac FR-260) manufactured by YAMAZEN Corporation, and the automatic chromatographic apparatus (CombiFlash Rf) manufactured by Teledyne Isco, Inc. were used as appropriate. It is to be noted that the abbreviations used in the working examples have the following meanings.

mg: milligram, g: gram, ml: millilitre, MHz: megahertz.

In the following working examples, nuclear magnetic resonance (hereinafter referred to as "$^1$H NMR") spectra are described, using tetramethylsilane as a standard substance and a δ value (ppm) as a chemical shift value. With regard to division patterns, "s" indicates singlet, "d" indicates doublet, "t" indicates triplet, "q" indicates quartet, and "m" indicates multiplet. Mass spectrometry (hereinafter referred to as "MS") was carried out according to a FAB (Fast Atom Bombardment) method, an EI (Electron Ionization) method, or an ESI (Electron Spray Ionization) method.

"Hexane" indicates n-hexane, "THF" indicates tetrahydrofuran, and "DMF" indicates dimethylformamide.

EXAMPLES

Example 1

6-[4-Methoxy-3-(3,3,6,6-tetramethyl-1,8-dioxo-2,3,4,5,6,7,8,9-octahydro-1H-xanthen-9-yl)phenyl]pyridine-2-carboxylic acid

[Formula 14]

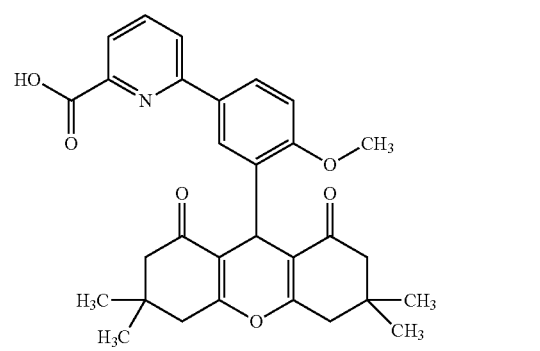

Example 1-1

[4-Methoxy-3-(3,3,6,6-tetramethyl-1,8-dioxo-2,3,4,5,6,7,8,9-octahydro-1H-xanthen-9-yl)phenyl]boronic acid (3-Formyl-4-methoxyphenyl)boronic acid (5.30 g, 29.5 mmol) and 5,5-dimethylcyclohexane-1,3-dione (8.26 g, 58.9 mmol) were added to a suspension of dodecylbenzenesulfonic acid (0.96 g, 2.94 mmol) in water (196 ml) at room temperature, and the mixture thus obtained was then stirred under heating to reflux for 5 hours. After air-cooling, a solid was collected from the reaction solution by filtration. The solid thus obtained was suspended in ethanol, and the solution thus obtained was then stirred under heating to reflux. After air-cooling, the solvent was distilled away from the reaction solution under reduced pressure. Diethyl ether was added to the residue thus obtained, and the solid thus generated was collected by filtration and was then dried to obtain the title compound (7.99 g, yield: 64%).

$^1$H-NMR Spectrum (500 MHz, DMSO-D$_6$) δ ppm: 7.69 (1H, m), 7.56-7.54 (1H, m), 6.82-6.80 (1H, m), 4.57 (1H, s), 3.68 (3H, s), 2.57-2.54 (2H, m), 2.38-2.35 (2H, m), 2.25-2.21 (2H, m), 1.99-1.96 (2H, m), 1.02 (6H, s), 0.83 (6H, s).

Example 1-2

6-[4-Methoxy-3-(3,3,6,6-tetramethyl-1,8-dioxo-2,3,4,5,6,7,8,9-octahydro-1H-xanthen-9-yl)phenyl]pyridine-2-carboxylic acid A suspension of the [4-methoxy-3-(3,3,6,6-tetramethyl-1,8-dioxo-2,3,4,5,6,7,8,9-octahydro-1H-xanthen-9-yl)phenyl]boronic acid produced in Example 1-1 (2.41 g, 5.68 mmol), 6-bromopyridine-2-carboxylic acid (1.17 g, 5.68 mmol), sodium carbonate (2.41 g, 22.7 mmol), and tetrakis(triphenylphosphine) palladium(0) (0.33 g, 0.28 mmol) in 1,2- dimethoxyethane (48.2 ml) and water (21 ml) was prepared at room temperature, and the prepared suspension was then stirred at 90° C. for 4 hours. After air-cooling, a 10% aqueous solution of citric acid was added to the reaction solution, and the mixed solution was then extracted with dichloromethane three times. The organic layer thus obtained was dried over anhydrous sodium sulfate. The solvent was distilled away under reduced pressure, and the residue thus obtained was then dissolved in THF (48 ml). Thereafter, an aqueous solution of lithium hydroxide monohydrate (524 mg, 12.5 mmol) was added to the solution obtained above, and the mixture thus obtained was then stirred at room temperature. Water was added to the reaction solution, and the resulting solution was then washed with diethyl ether. Thereafter, a 1 N aqueous solution of hydrochloric acid (12.5 ml) was added to the water layer, and the resultant was then extracted with dichloromethane four times. The organic layer thus obtained was dried over anhydrous sodium sulfate. The solvent was distilled away under reduced pressure, and the residue thus obtained was then purified by silica gel column chromatography (methanol:dichloromethane=3:97 to 4:96, v/v). The solid thus obtained was washed with a mixed solution of diethyl ether and hexane, followed by collection by filtration and drying, to obtain the title compound (2.19 g, yield: 77%).

$^1$H-NMR Spectrum (400 MHz, CDCl$_3$) δ ppm: 8.10-7.94 (4H, m), 7.82 (1H, dd, J=8.6, 2.3 Hz), 6.90 (1H, d, J=8.6 Hz), 4.94 (1H, s), 3.84 (3H, s), 2.53-2.37 (4H, m), 2.26-2.12 (4H, m), 1.11 (6H, s), 0.96 (6H, s);

MS (ESI) m/z: 500 [M−H]$^-$.

Example 2

4-[4-Methoxy-3-(3,3,6,6-tetramethyl-1,8-dioxo-2,3,4,5,6,7,8,9-octahydro-1H-xanthen-9-yl)phenyl]pyridine-2-carboxylic acid

[Formula 15]

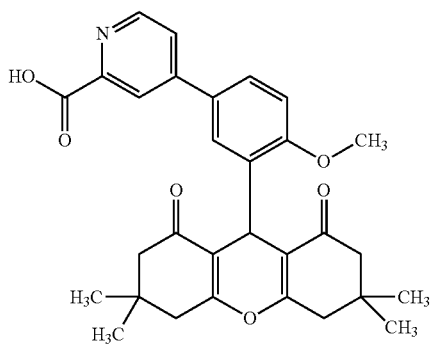

Example 2-1

Methyl 4-[4-methoxy-3-(3,3,6,6-tetramethyl-1,8-dioxo-2,3,4,5,6,7,8,9-octahydro-1H-xanthen-9-yl)phenyl]pyridine-2-carboxylate A suspension of the [4-methoxy-3-(3,3,6,6-tetramethyl-1,8-dioxo-2,3,4,5,6,7,8,9-octahydro-1H-xanthen-9-yl)phenyl]boronic acid produced in Example 1-1 (511 mg, 1.20 mmol), methyl 4-chloropyridine-2-carboxylate (207 mg, 1.20 mmol), tri(o-tolyl)phosphine (73.3 mg, 0.24 mmol), cesium fluoride (548 mg, 3.61 mmol), and palladium(II) acetate (13.5 mg, 0.06 mol) in 1,2-dimethoxyethane (10.2 ml) was prepared at room temperature, and the suspension thus prepared was then stirred at 90° C. for 7 hours. After air-cooling, water was added to the reaction solution, and the mixed solution was then extracted with ethyl acetate. The organic layer thus obtained was dried over anhydrous sodium sulfate. The solvent was distilled away under reduced pressure, and the residue thus obtained was then purified by silica gel column chromatography (ethyl acetate:hexane=34:66 to 25:75, v/v) to obtain the title compound (123 mg, yield: 20%).

$^1$H-NMR Spectrum (500 MHz, CDCl$_3$) δ ppm: 8.71 (1H, d, J=5.4 Hz), 8.34 (1H, d, J=2.0 Hz), 7.80 (1H, d, J=2.0 Hz), 7.71-7.70 (1H, m), 7.50-7.49 (1H, m), 6.88 (1H, d, J=8.3 Hz), 4.93 (1H, s), 4.04 (3H, s), 3.84 (3H, s), 2.51-2.38 (4H, m), 2.25-2.13 (4H, m), 1.11 (6H, s), 0.97 (6H, s).

Example 2-2

4-[4-Methoxy-3-(3,3,6,6-tetramethyl-1,8-dioxo-2,3,4,5,6,7,8,9-octahydro-1H-xanthen-9-yl)phenyl]pyridine-2-carboxylic acid A solution of lithium hydroxide monohydrate (21.7 mg, 0.52 mmol) in water (2.4 ml) was added to a solution of the methyl 4-[4-methoxy-3-(3,3,6,6-tetramethyl-1,8-dioxo-2,3,4,5,6,7,8,9-octahydro-1H-xanthen-9-yl)phenyl]pyridine-2-carboxylate produced in Example 2-1 (121 mg, 0.23 mmol) in THF (4.8 ml) at room temperature, and the mixed solution was then stirred at the same temperature as above for 1 hour. Thereafter, water was added to the reaction solution, and the mixed solution was then washed with diethyl ether. A 1 N aqueous solution of hydrochloric acid (0.52 ml) was added to the water layer, and the mixed solution was then extracted with dichloromethane four times. The organic layer thus obtained was dried over anhydrous sodium sulfate. Thereafter, the solvent was distilled away under reduced pressure, and the residue thus obtained was then washed with a mixed solution of diethyl ether and hexane, followed by collection by filtration and drying, to obtain the title compound (84.5 mg, yield: 72%).

$^1$H-NMR Spectrum (400 MHz, DMSO-D$_6$) δ ppm: 8.73-8.72 (1H, m), 8.21 (1H, m), 7.85-7.84 (1H, m), 7.66-7.64 (2H, m), 7.06-7.04 (1H, m), 4.67 (1H, s), 3.76 (3H, s), 2.62-2.57 (2H, m), 2.43-2.39 (2H, m), 2.29-2.24 (2H, m), 2.04-1.99 (2H, m), 1.04 (6H, s), 0.86 (6H, s);

MS (ESI) m/z: 502 [M+H]$^+$.

Example 3

9-{2-Methoxy-5-[6-(morpholin-4-ylcarbonyl)pyridin-2-yl]phenyl}-3,3,6,6-tetramethyl-3,4,5,6,7,9-hexahydro-1H-xanthene-1,8(2H)-dione

[Formula 16]

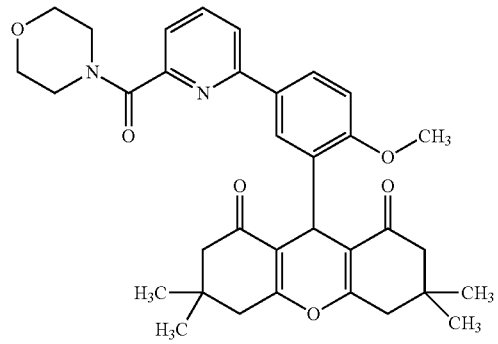

Morpholine (0.0625 ml, 0.72 mmol) was added to a solution of the 6-[4-methoxy-3-(3,3,6,6-tetramethyl-1,8-dioxo-2,3,4,5,6,7,8,9-octahydro-1H-xanthen-9-yl)phenyl]pyridine-2-carboxylic acid produced in Example 1-2 (180 mg, 0.36 mmol), 1-ethyl-3-(3-dimethylaminopropyl)carbodiimide hydrochloride (138 mg, 0.72 mmol), and 1-hydroxybenzotriazole monohydrate (55.0 mg, 0.36 mmol) in DMF (4 ml) at room temperature, and the mixture thus obtained was then stirred at the same temperature as above for 24.5 hours. Thereafter, water was added to the reaction solution, and the mixed solution was then extracted with ethyl acetate. The organic layer thus obtained was washed with water, and was then dried over anhydrous sodium sulfate. The solvent was distilled away under reduced pressure, and the residue thus obtained was then purified by silica gel column chromatography (ethyl acetate). The solid thus obtained was washed with a mixed solution of diethyl ether and hexane, followed by collection by filtration and drying, to obtain the title compound (161 mg, yield: 79%).

$^1$H-NMR Spectrum (400 MHz, CDCl$_3$) δ ppm: 8.06 (1H, d, J=2.3 Hz), 7.85-7.80 (3H, m), 7.59-7.56 (1H, m), 6.85 (1H, d, J=8.6 Hz), 4.92 (1H, s), 3.85-3.82 (11H, m), 2.51-2.37 (4H, m), 2.25-2.11 (4H, m), 1.10 (6H, s), 0.96 (6H, s);

MS (ESI) m/z: 571 [M+H]$^+$

Example 4

6-[4-Methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid

[Formula 17]

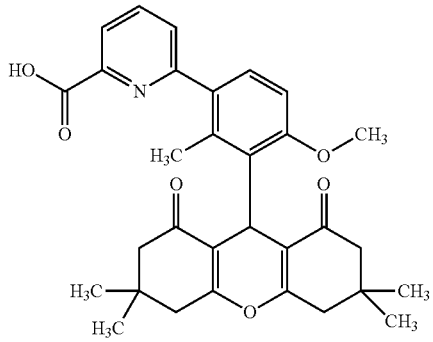

Example 4-1

6-Methoxy-2-methyl-3-(4,4,5,5-tetramethyl-1,3,2-dioxaborolan-2-yl)benzaldehyde

Bis(triphenylphosphine)palladium(II) dichloride (4.14 g, 5.78 mmol) was added to a suspension of 3-bromo-6-methoxy-2-methylbenzaldehyde (26.5 g, 116 mmol) as a known compound, bis(pinacolato)diboron (31.8 g, 121 mmol), and potassium acetate (35.1 g, 347 mmol) in 1,4-dioxane (265 ml) under a nitrogen atmosphere, and the mixture thus obtained was then stirred under heating to reflux for 6 hours. After air-cooling, water was added to the reaction solution, and the mixed solution was then extracted with ethyl acetate. The organic layer thus obtained was dried over anhydrous sodium sulfate. The solvent was distilled away under reduced pressure, and the residue thus obtained was then purified by silica gel column chromatography (ethyl acetate:hexane=1:9 to 1:8, v/v). The solid thus obtained was washed with a mixed solution of diethyl ether and hexane, followed by collection by filtration and drying, to obtain the title compound (22.0 g, yield: 69%).

$^1$H-NMR Spectrum (400 MHz, CDCl$_3$) δ ppm: 10.64 (1H, s), 7.90 (1H, d, J=8.2 Hz), 6.81 (1H, d, J=8.2 Hz), 3.90 (3H, s), 2.77 (3H, s), 1.34 (12H, s).

Example 4-2

Methyl 6-(3-formyl-4-methoxy-2-methylphenyl)pyridine-2-carboxylate

A suspension of the 6-methoxy-2-methyl-3-(4,4,5,5-tetramethyl-1,3,2-dioxaborolan-2-yl)benzaldehyde produced in Example 4-1 (1.01 g, 3.66 mmol), methyl 6-bromopyridine-2-carboxylate (0.79 g, 3.66 mmol), sodium carbonate (1.16 g, 11.0 mmol), and tetrakis(triphenylphosphine)palladium(0) (0.21 g, 0.18 mmol) in 1,2-dimethoxyethane (20.2 ml) and water (8.8 ml) was prepared at room temperature, and the suspension thus prepared was then stirred at 90° C. for 7 hours. After air-cooling, an aqueous solution of ammonium chloride was added to the reaction solution, and the mixed solution was then extracted with dichloromethane 21 times. The organic layer thus obtained was dried over anhydrous sodium sulfate. The solvent was distilled away under reduced pressure, and the residue thus obtained was then dissolved in DMF (20.2 ml). Thereafter, potassium carbonate (1.21 g, 8.78 mmol) and methyl iodide (0.27 ml, 4.39 mmol) were added to the resulting solution, and the mixture thus obtained was then stirred at 40° C. for 4 hours. After air-cooling, water was added to the reaction solution, and the mixed solution was then extracted with ethyl acetate. The organic layer thus obtained was washed with water, and was then dried over anhydrous sodium sulfate. The solvent was distilled away under reduced pressure, and the residue thus obtained was then purified by silica gel column chromatography (ethyl acetate:hexane=40:60, v/v) to obtain the title compound (0.625 g, yield: 60%).

$^1$H-NMR Spectrum (500 MHz, CDCl$_3$) δ ppm: 10.69 (1H, s), 8.11 (1H, d, J=7.8 Hz), 7.92-7.88 (1H, m), 7.59 (1H, d, J=8.8 Hz), 7.52 (1H, d, J=7.8 Hz), 6.94 (1H, d, J=8.8 Hz), 4.01 (3H, s), 3.95 (3H, s), 2.50 (3H, s).

Example 4-3

Methyl 6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylate Pyrrolidine (0.018 ml, 0.22 mmol) was added to a suspension of the methyl 6-(3-formyl-4-methoxy-2-methylphenyl)pyridine-2-carboxylate produced in Example 4-2 (620 mg, 2.17 mmol) and 5,5-dimethylcyclohexane-1,3-dione (701 mg, 5.00 mmol) in ethanol (12.4 ml) at room temperature, and the mixture thus obtained was then stirred at 80° C. for 2 hours. After air-cooling, the solvent was distilled away from the reaction solution under reduced pressure. The residue thus obtained was dissolved in chloroform (12.4 ml), and p-toluenesulfonic acid monohydrate (112 mg, 0.65 mmol) was then added to the solution obtained above. The mixture thus obtained was stirred at 70° C. for 4 hours. After air-cooling, water was added to the reaction solution, and the mixed solution was then extracted with dichloromethane. The organic layer thus obtained was dried over anhydrous sodium sulfate. The solvent was distilled away under reduced pressure, and the residue thus obtained was then purified by silica gel column chromatography (ethyl acetate:hexane=1:1, v/v) to obtain the title compound (1.05 g, yield: 91%).

¹H-NMR Spectrum (400 MHz, CDCl₃) δ ppm: 8.07-8.04 (1H, m), 7.84-7.80 (1H, m), 7.62-7.59 (1H, m), 7.24 (1H, d, J=8.2 Hz), 6.69 (1H, d, J=8.6 Hz), 5.07 (1H, s), 3.99 (3H, s), 3.71 (3H, s), 2.86 (3H, s), 2.49-2.11 (8H, m), 1.10 (6H, s), 0.95 (6H, s).

Example 4-4

6-[4-Methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid A solution of lithium hydroxide monohydrate (0.18 g, 4.36 mmol) in water (10.5 ml) was added dropwise to a solution of the methyl 6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylate produced in Example 4-3 (1.05 g, 1.98 mmol) in THF (21 ml) at room temperature, and the mixture thus obtained was then stirred at the same temperature as above for 3 hours. Thereafter, water was added to the reaction solution, and the mixed solution was then washed with diethyl ether. Thereafter, a 1 N aqueous solution of hydrochloric acid (4.36 ml) was added to the water layer, and the mixed solution was then extracted with dichloromethane. The organic layer thus obtained was dried over anhydrous sodium sulfate. The solvent was distilled away under reduced pressure, and the residue thus obtained was then washed with a mixed solution of diethyl ether and hexane, followed by collection by filtration and drying, to obtain the title compound (0.75 g, yield: 73%).

¹H-NMR Spectrum (400 MHz, CDCl₃) δ ppm: 8.16-8.14 (1H, m), 7.96-7.93 (1H, m), 7.71-7.68 (1H, m), 7.19 (1H, d, J=8.6 Hz), 6.73 (1H, d, J=8.6 Hz), 5.07 (1H, s), 3.74 (3H, s), 2.88 (3H, s), 2.51-2.35 (4H, m), 2.26-2.13 (4H, m), 1.11 (6H, s), 0.97 (6H, s).
MS (ESI) m/z: 516 [M+H]⁺.

Example 5

6-[4-Methoxy-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide

[Formula 18]

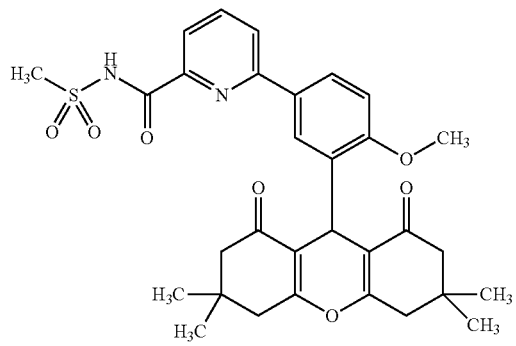

1,1'-Carbonyldiimidazole (54.6 mg, 0.34 mmol) was added to a solution of the 6-[4-methoxy-3-(3,3,6,6-tetramethyl-1,8-dioxo-2,3,4,5,6,7,8,9-octahydro-1H-xanthen-9-yl)phenyl]pyridine-2-carboxylic acid produced in Example 1-2 (130 mg, 0.26 mmol) in DMF (2.6 ml) at room temperature, and the mixture thus obtained was then stirred at the same temperature as above for 2 hours. Thereafter, methanesulfonamide (32.1 mg, 0.34 mmol) and 1,8-diazabicyclo[5.4.0]undec-7-ene (0.050 ml, 0.34 mmol) were added to the resulting solution at room temperature, and the mixture thus obtained was then stirred at the same temperature as above for 71 hours. Thereafter, an aqueous solution of citric acid (249 mg, 1.30 mmol) was added to the reaction solution, and the mixed solution was then extracted with ethyl acetate. The organic layer thus obtained was washed with water, and was then dried over anhydrous sodium sulfate. The solvent was distilled away under reduced pressure, and the residue thus obtained was then purified by silica gel column chromatography (methanol:dichloromethane=0:1 to 1:9, v/v). Ethanol was added to the fraction thus obtained, and the generated solid was then collected by filtration and dried to obtain the title compound (84.4 mg, yield: 56%).

¹H-NMR Spectrum (400 MHz, CDCl₃) δ ppm: 8.09-7.92 (4H, m), 7.87-7.84 (1H, m), 6.91 (1H, d, J=8.6 Hz), 4.94 (1H, s), 3.85 (3H, s), 3.43 (3H, s), 2.52-2.41 (4H, m), 2.26-2.12 (4H, m), 1.11 (6H, s), 0.96 (6H, s);
MS (ESI) m/z: 579 [M+H]⁺.

Example 6

6-[4-Methoxy-3-(3,3,6,6-tetramethyl-1,8-dioxo-2,3,4,5,6,7,8,9-octahydro-1H-xanthen-9-yl)phenyl]pyridine-2-carbonitrile

[Formula 19]

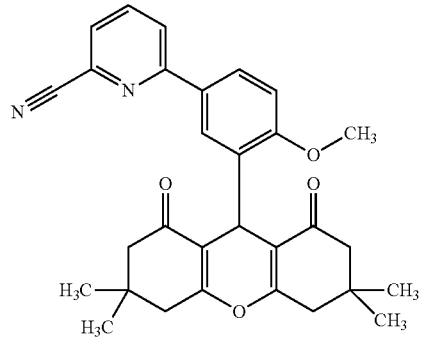

A suspension of the [4-methoxy-3-(3,3,6,6-tetramethyl-1,8-dioxo-2,3,4,5,6,7,8,9-octahydro-1H-xanthen-9-yl)phenyl]boronic acid produced in Example 1-1 (1.01 g, 2.37 mmol), 6-chloropyridine-2-carbonitrile (342 mg, 2.37 mmol), sodium carbonate (1.01 g, 9.48 mmol), and tetrakis(triphenylphosphine)palladium(0) (137 mg, 0.12 mmol) in 1,2-dimethoxyethane (20.1 ml) and water (8.7 ml) was prepared at room temperature, and the suspension thus prepared was then stirred at 90° C. for 45 minutes. After air-cooling, water was added to the reaction solution, and the mixed solution was then extracted with ethyl acetate. The organic layer thus obtained was dried over anhydrous sodium sulfate. The solvent was distilled away under reduced pressure, and the residue thus obtained was then purified by silica gel column chromatography (ethyl acetate:hexane=1:1, v/v). The solid thus obtained was washed with a mixed solution of diethyl ether and hexane, followed by collection by filtration and drying, to obtain the title compound (1.09 g, yield: 95%).

¹H-NMR Spectrum (400 MHz, CDCl₃) δ ppm: 8.02-7.92 (3H, m), 7.82-7.78 (1H, m), 7.52 (1H, d, J=7.0 Hz), 6.88 (1H, d, J=8.6 Hz), 4.93 (1H, s), 3.84 (3H, s), 2.51-2.38 (4H, m), 2.25-2.11 (4H, m), 1.10 (6H, s), 0.96 (6H, s);
MS (ESI) m/z: 483 [M+H]⁺.

Example 7

9-{2-Methoxy-5-[6-(1H-tetrazol-5-yl)pyridin-2-yl]phenyl}-3,3,6,6-tetramethyl-3,4,5,6,7,9-hexahydro-1H-xanthene-1,8(2H)-dione

[Formula 20]

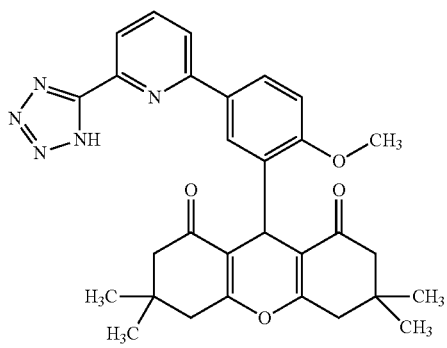

A suspension of the 6-[4-methoxy-3-(3,3,6,6-tetramethyl-1,8-dioxo-2,3,4,5,6,7,8,9-octahydro-1H-xanthen-9-yl)phenyl]pyridine-2-carbonitrile produced in Example 6 (500 mg, 1.04 mmol), sodium azide (76.4 mg, 1.14 mmol), and ammonium chloride (61.0 mg, 1.14 mmol) in DMF (10 ml) was prepared at room temperature, and the suspension thus prepared was then stirred at 80° C. for 4 hours. After air-cooling, water was added to the reaction solution, and the mixed solution was then extracted with ethyl acetate. The organic layer thus obtained was dried over anhydrous sodium sulfate. The solvent was distilled away under reduced pressure, and the residue thus obtained was then purified by silica gel column chromatography (ethyl acetate:hexane=66:34, v/v, methanol:dichloromethane=3:97 to 5:95, v/v). The solid thus obtained was washed with a mixed solution of diethyl ether and hexane, followed by collection by filtration and drying, to obtain the title compound (51 mg, yield: 9.4%).

$^1$H-NMR Spectrum (400 MHz, CDCl$_3$) δ ppm: 8.35 (1H, d, J=2.3 Hz), 8.25-8.23 (1H, m), 7.91-7.87 (1H, m), 7.73-7.70 (1H, m), 7.60 (1H, dd, J=8.2, 2.3 Hz), 6.84 (1H, d, J=8.2 Hz), 4.87 (1H, s), 3.78 (3H, s), 2.54-2.38 (4H, m), 2.28-2.14 (4H, m), 1.12 (6H, s), 0.96 (6H, s);
MS (ESI) m/z: 526 [M+H]$^+$.

Example 8

9-{2-Methoxy-5-[6-(5-oxo-4,5-dihydro-1,2,4-oxadiazol-3-yl)pyridin-2-yl]phenyl}-3,3,6,6-tetramethyl-3,4,5,6,7,9-hexahydro-1H-xanthene-1,8(2H)-dione

[Formula 21]

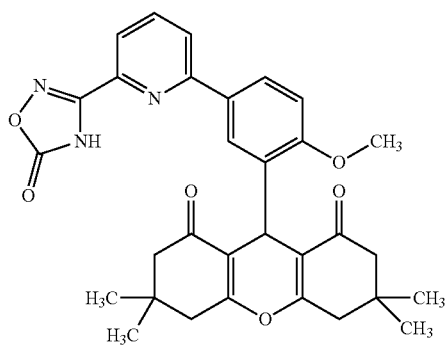

Example 8-1

N'-hydroxy-6-[4-methoxy-3-(3,3,6,6-tetramethyl-1,8-dioxo-2,3,4,5,6,7,8,9-octahydro-1H-xanthen-9-yl)phenyl]pyridine-2-carboximidamide Sodium carbonate (122 mg, 1.15 mmol) was added to a suspension of the 6-[4-methoxy-3-(3,3,6,6-tetramethyl-1,8-dioxo-2,3,4,5,6,7,8,9-octahydro-1H-xanthen-9-yl)phenyl]pyridine-2-carbonitrile produced in Example 6 (410 mg, 0.85 mmol) and hydroxylamine hydrochloride (73.8 mg, 1.06 mmol) in methanol (8.2 ml) at room temperature, and the mixture thus obtained was then stirred at the same temperature as above for 25 hours. Thereafter, water was added to the reaction solution, and the mixed solution was then extracted with dichloromethane. The organic layer thus obtained was dried over anhydrous sodium sulfate. The solvent was distilled away under reduced pressure to obtain the title compound (429 mg, yield: 98%).

$^1$H-NMR Spectrum (400 MHz, CDCl$_3$) δ ppm: 8.05 (1H, d, J=2.3 Hz), 7.85 (1H, dd, J=8.6, 2.3 Hz), 7.78-7.69 (3H, m), 6.87 (1H, d, J=8.6 Hz), 5.77 (2H, s), 4.97 (1H, s), 3.84 (3H, s), 2.51-2.37 (4H, m), 2.25-2.12 (4H, m), 1.10 (6H, s), 0.96 (6H, s).

Example 8-2

9-{2-Methoxy-5-[6-(5-oxo-4,5-dihydro-1,2,4-oxadiazol-3-yl)pyridin-2-yl]phenyl}-3,3,6,6-tetramethyl-3,4,5,6,7,9-hexahydro-1H-xanthene-1,8(2H)-dione 1,1'-Carbonyldiimidazole (173 mg, 1.07 mmol) was added to a solution of the N'-hydroxy-6-[4-methoxy-3-(3,3,6,6-tetramethyl-1,8-dioxo-2,3,4,5,6,7,8,9-octahydro-1H-xanthen-9-yl)phenyl]pyridine-2-carboximidamide produced in Example 8-1 (424 mg, 0.82 mmol) in THF (8.5 ml) at room temperature, and the mixture thus obtained was then stirred at the same temperature as above for 2 hours. Thereafter, 1,8-diazabicyclo[5.4.0]undec-7-ene (0.160 ml, 1.07 mmol) was added to the resulting solution, and the mixture thus obtained was then stirred for 4.5 hours. Subsequently, an aqueous solution of ammonium chloride was added to the reaction solution, and the mixed solution was then extracted with dichloromethane twice. The organic layer thus obtained was dried over anhydrous sodium sulfate. The solvent was distilled away under reduced pressure, and the residue thus obtained was then purified by silica gel thin-layer chromatography (methanol:dichloromethane=1:10, v/v). The solid thus obtained was washed with a mixed solution of diethyl ether and hexane, followed by collection by filtration and drying, to obtain the title compound (309 mg, yield: 69%).

$^1$H-NMR Spectrum (400 MHz, CDCl$_3$) δ ppm: 8.21 (1H, d, J=2.3 Hz), 7.88-7.81 (3H, m), 7.74-7.71 (1H, m), 6.84 (1H, d, J=8.6 Hz), 4.88 (1H, s), 3.78 (3H, s), 2.52-2.37 (4H, m), 2.26-2.13 (4H, m), 1.11 (6H, s), 0.96 (6H, s);
MS (ESI) m/z: 542 [M+H]$^+$.

Example 9

6-[4-Methoxy-2-methyl-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide

[Formula 22]

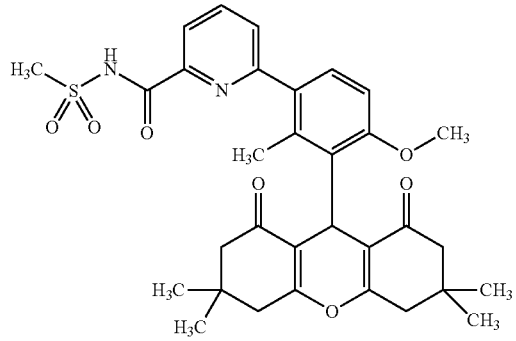

A solution of the 6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid produced in Example 4-4 (1.16 g, 2.25 mmol), methanesulfonamide (0.26 g, 2.70 mmol), 1-ethyl-3-(3-dimethylaminopropyl)carbodiimide hydrochloride (0.86 g, 4.50 mmol), and 4-dimethylaminopyridine (0.05 g, 0.45 mmol) in dichloromethane (23 ml) was prepared at room temperature, and the solution thus obtained was then stirred at the same temperature as above for 3.5 hours. Thereafter, an aqueous solution of ammonium chloride was added to the reaction solution, and the mixed solution was then extracted with dichloromethane. The organic layer thus obtained was dried over anhydrous sodium sulfate. The solvent was distilled away under reduced pressure, and the residue thus obtained was then purified by silica gel column chromatography (ethyl acetate:dichloromethane=1:4, v/v, methanol:dichloromethane=2:98 to 4:96, v/v). The solid thus obtained was washed with a mixed solution of diethyl ether and hexane, followed by collection by filtration and drying, to obtain the title compound (419 mg, yield: 31%).

$^1$H-NMR Spectrum (500 MHz, CDCl$_3$) δ ppm: 8.13 (1H, d, J=7.8 Hz), 7.93-7.90 (1H, m), 7.69 (1H, d, J=7.8 Hz), 7.20 (1H, d, J=8.3 Hz), 6.74 (1H, d, J=8.3 Hz), 5.06 (1H, s), 3.75 (3H, s), 3.40 (3H, s), 2.86 (3H, s), 2.50-2.36 (4H, m), 2.25-2.14 (4H, m), 1.11 (6H, s), 0.98 (6H, s);

MS (ESI) m/z: 593 [M+H]$^+$.

Example 10

6-[4-Methoxy-2-methyl-3-(3,3,6,6-tetramethyl-1,8-dioxo-2,3,4,5,6,7,8,9-octahydro-1H-xanthen-9-yl)phenyl]-3-methylpyridine-2-carboxylic acid

[Formula 23]

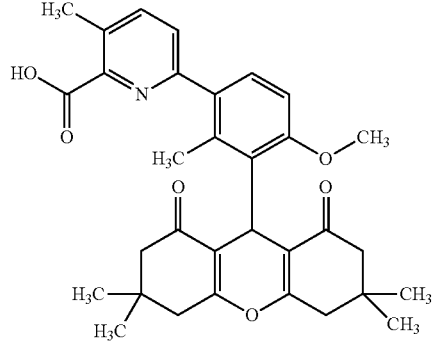

Example 10-1

Tert-butyl 6-chloro-3-methylpyridine-2-carboxylate p-Toluenesulfonyl chloride (10.5 g, 55.1 mmol) was added to a solution of 6-chloro-3-methylpyridine-2-carboxylic acid (4.73 g, 27.6 mmol) as a known compound in tert-butyl alcohol (150 ml) and pyridine (21 ml) at room temperature, and the mixture thus obtained was then stirred at the same temperature as above for 24 hours. Thereafter, a solution of sodium hydrogen carbonate (11.6 g, 138 mmol) in water (300 ml) was added to the resulting solution, and the mixed solution was then stirred. Then, the solvent was distilled away from the reaction solution under reduced pressure. While being washed with water, the solid thus generated was collected by filtration, and was then dried to obtain the title compound (5.85 g, yield: 93%).

$^1$H-NMR Spectrum (400 MHz, CDCl$_3$) δ ppm: 7.53-7.51 (1H, m), 7.31-7.29 (1H, m), 2.46 (3H, s), 1.63 (9H, s).

Example 10-2

Tert-butyl 6-(3-formyl-4-methoxy-2-methylphenyl)-3-methylpyridine-2-carboxylate

A suspension of the 6-methoxy-2-methyl-3-(4,4,5,5-tetramethyl-1,3,2-dioxaborolan-2-yl)benzaldehyde produced in Example 4-1 (1.00 g, 3.62 mmol), the tert-butyl 6-chloro-3-methylpyridine-2-carboxylate produced in Example 10-1 (0.82 g, 3.62 mmol), sodium carbonate (1.15 g, 10.9 mmol), and tetrakis(triphenylphosphine)palladium(0) (0.21 g, 0.18 mmol) in 1,2-dimethoxyethane (20 ml) and water (8.7 ml) was prepared at room temperature, and the suspension thus prepared was then stirred at 90° C. for 4.5 hours. After air-cooling, water was added to the reaction solution, and the mixed solution was then extracted with ethyl acetate. The organic layer thus obtained was dried over anhydrous sodium sulfate. The solvent was distilled away under reduced pressure, and the residue thus obtained was then purified by silica gel column chromatography (ethyl acetate:hexane=1:3, v/v) to obtain the title compound (1.31 g, yield: 106%).

$^1$H-NMR Spectrum (400 MHz, CDCl$_3$) δ ppm: 10.68 (1H, s), 7.61-7.59 (2H, m), 7.32-7.30 (1H, m), 6.92 (1H, d, J=9.0 Hz), 3.93 (3H, s), 2.53 (3H, s), 2.52 (3H, s), 1.63 (9H, s).

Example 10-3

6-[4-Methoxy-2-methyl-3-(3,3,6,6-tetramethyl-1,8-dioxo-2,3,4,5,6,7,8,9-octahydro-1H-xanthen-9-yl)phenyl]-3-methylpyridine-2-carboxylic acid Pyrrolidine (0.03 ml, 0.36 mmol) was added to a suspension of the tert-butyl 6-(3-formyl-4-methoxy-2-methylphenyl)-3-methylpyridine-2-carboxylate produced in Example 10-2 (1.31 g) and 5,5-dimethylcyclohexane-1,3-dione (1.17 g, 8.33 mmol) in ethanol (26.2 ml) at room temperature, and the mixture thus obtained was then stirred at 80° C. for 3 hours. After air-cooling, the solvent was distilled away from the reaction solution under reduced pressure. The residue thus obtained was dissolved in chloroform (26.2 ml), and p-toluenesulfonic acid monohydrate (0.19 g, 1.09 mmol) was then added to the solution obtained above at room temperature. The mixture thus obtained was stirred at 70° C. for 2.5 hours. After air-cooling, water was added to the reaction solution, and the mixed solution was then extracted with dichloromethane twice. The organic layer thus obtained was dried over anhydrous sodium sulfate, and the solvent was then distilled away under reduced pressure. The residue thus obtained was dissolved in dichloromethane (51 ml), and trifluoroacetic acid (25.5 ml) was then added to the solution obtained above at room temperature. The mixture thus obtained was stirred at the same temperature as above for 4.5 hours. Thereafter, the solvent was distilled away from the reaction solution under reduced pressure. A small amount of saturated aqueous solution of sodium hydrogen carbonate was added to the residue thus obtained, and thereafter, a 10% aqueous solution of citric acid was added thereto. The solution thus mixed was extracted with dichloromethane. The organic layer thus obtained was dried over anhydrous sodium sulfate. The solvent was distilled away under reduced pressure, and the residue thus obtained was then dissolved in THF (51 ml). A 1 N aqueous solution of sodium hydroxide (7.96 ml) was added to the solution obtained above, and the mixture thus obtained was then stirred at room temperature. Thereafter, water was added to the reaction solution, and the mixed solution was then washed with diethyl ether. A 1 N aqueous solution of hydrochloric acid (7.96 ml) was added to the water layer thus obtained, and the mixed solution was then extracted with dichloromethane. The organic layer thus obtained was dried over anhydrous sodium sulfate. The solvent was distilled away under reduced pressure, and the solid thus obtained was then washed with a mixed solution of diethyl ether and hexane, followed by collection by filtration and drying, to obtain the title compound (0.966 g, yield: 50%).

$^1$H-NMR Spectrum (500 MHz, CDCl$_3$) δ ppm: 7.71-7.69 (1H, m), 7.59-7.58 (1H, m), 7.18-7.17 (1H, m), 6.72-6.71 (1H, m), 5.07 (1H, s), 3.74 (3H, s), 2.88 (3H, s), 2.81 (3H, s), 2.50-2.36 (4H, m), 2.25-2.14 (4H, m), 1.11 (6H, s), 0.97 (6H, s);

MS (ESI) m/z: 530 [M+H]$^+$.

Example 11

3-Hydroxy-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid

[Formula 24]

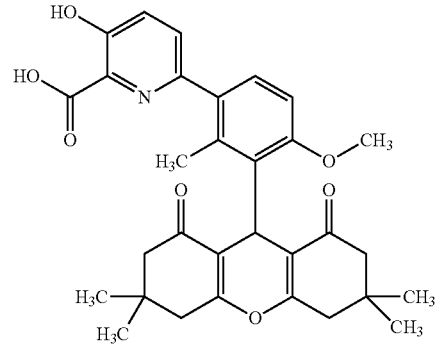

Example 11-1

Methyl 3-(benzyloxy)-6-(3-formyl-4-methoxy-2-methylphenyl)pyridine-2-carboxylate A suspension of the 6-methoxy-2-methyl-3-(4,4,5,5-tetramethyl-1,3,2-dioxaborolan-2-yl)benzaldehyde produced in Example 4-1 (1.91 g, 6.92 mmol), methyl 3-(benzyloxy)-6-bromopyridine-2-carboxylate (PCT Int. Appl., 2010080478, 15 Jul. 2010) (2.23 g, 6.92 mmol), sodium carbonate (2.20 g, 20.8 mmol), and tetrakis(triphenylphosphine)palladium(0) (0.40 g, 0.35 mmol) in 1,2-dimethoxyethane (38 ml) and water (17 ml) was prepared at room temperature, and the suspension thus prepared was then stirred at 90° C. for 3 hours. After air-cooling, water was added to the reaction solution, and the mixed solution was then extracted with ethyl acetate. The organic layer thus obtained was dried over anhydrous sodium sulfate. The solvent was distilled away under reduced pressure, and the residue thus obtained was then purified by silica gel column chromatography (ethyl acetate:hexane=2:3, v/v) to obtain the title compound (3.02 g, yield: 112%).

$^1$H-NMR Spectrum (400 MHz, CDCl$_3$) δ ppm: 10.67 (1H, s), 7.70-7.34 (8H, m), 6.91 (1H, d, J=8.6 Hz), 5.25 (2H, s), 3.97 (3H, s), 3.93 (3H, s), 2.49 (3H, s).

Example 11-2

Methyl 3-(benzyloxy)-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylate Pyrrolidine (0.057 ml, 0.69 mmol) was added to a suspension of the methyl 3-(benzyloxy)-6-(3-formyl-4-methoxy-2-methylphenyl)pyridine-2-carboxylate produced in Example 11-1 (3.02 g) and 5,5-dimethylcyclohexane-1,3-dione (2.23 g, 15.92 mmol) in ethanol (60 ml) at room temperature, and the mixture thus obtained was then stirred at 80° C. for 2 hours. After air-cooling, the solvent was distilled away from the reaction solution under reduced pressure. The residue thus obtained was dissolved in chloroform (60 ml), and p-toluenesulfonic acid monohydrate (0.357 g, 2.08 mmol) was then added to the solution obtained above at room temperature. The mixture thus obtained was stirred at 70° C. for 1.5 hours. After air-cooling, water was added to the reaction solution, and the mixed solution was then extracted with ethyl acetate. The organic layer thus obtained was dried over anhydrous sodium sulfate. The solvent was distilled away under reduced pressure, and the residue thus obtained was then purified by silica gel column chromatography (ethyl acetate:hexane=2:3 to 1:1, v/v) to obtain the title compound (3.56 g, yield: 81%).

$^1$H-NMR Spectrum (400 MHz, CDCl$_3$) δ ppm: 7.51-7.32 (7H, m), 7.23-7.20 (1H, m), 6.66 (1H, d, J=8.6 Hz), 5.24 (2H, s), 5.06 (1H, s), 3.96 (3H, s), 3.70 (3H, s), 2.84 (3H, s), 2.48-2.33 (4H, m), 2.22-2.10 (4H, m), 1.09 (6H, s), 0.94 (6H, s).

Example 11-3

Methyl 3-hydroxy-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylate A 10% palladium carbon catalyst (wet) (3.15 g) was added to a solution of the methyl 3-(benzyloxy)-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylate produced in Example 11-2 (3.15 g, 4.95 mmol) in THF (63 ml) at room temperature, and the mixture thus obtained was then stirred under a hydrogen atmosphere at room temperature for 3 hours. A solid was removed from the reaction solution by filtration, and the solvent was then distilled away from the filtrate thus obtained under reduced pressure to obtain the title compound (2.58 g, yield: 95%).

$^1$H-NMR Spectrum (400 MHz, CDCl$_3$) δ ppm: 10.71 (1H, s), 7.55 (1H, d, J=8.6 Hz), 7.37 (1H, d, J=8.6 Hz), 7.19-7.17 (1H, m), 6.66 (1H, d, J=8.6 Hz), 5.06 (1H, s), 4.02 (3H, s), 3.70 (3H, s), 2.84 (3H, s), 2.49-2.33 (4H, m), 2.23-2.10 (4H, m), 1.10 (6H, s), 0.94 (6H, s).

Example 11-4

3-Hydroxy-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid Lithium hydroxide monohydrate (84.6 mg, 2.02 mmol) was added to a solution of the methyl 3-hydroxy-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylate produced in Example 11-3 (250 mg, 0.46 mmol) in THF (5 ml) and water (2.5 ml) at room temperature, and the mixture thus obtained was then stirred at the same temperature as above for 21 hours. Thereafter, water was added to the reaction solution, and the mixed solution was then washed with diethyl ether. A 1 N aqueous solution of hydrochloric acid (2.02 ml) was added to the water layer, and the solution thus mixed was then extracted with dichloromethane seven times. The organic layer thus obtained was dried over anhydrous sodium sulfate. The solvent was distilled away under reduced pressure, and the residue thus obtained was then purified by silica gel column chromatography (methanol:dichloromethane=3:97 to 6:94, v/v). The fraction thus obtained was washed with a mixed solution of diethyl ether and hexane, followed by collection by filtration and drying, to obtain the title compound (95.6 mg, yield: 39%).

$^1$H-NMR Spectrum (400 MHz, DMSO-D$_6$) δ ppm: 7.23 (1H, s), 7.18 (1H, d, J=8.2 Hz), 7.03 (1H, d, J=8.6 Hz), 6.76 (1H, d, J=8.6 Hz), 4.83 (1H, s), 3.67 (3H, s), 2.66 (3H, s), 2.59-2.36 (4H, m), 2.27-2.01 (4H, m), 1.04 (6H, s), 0.87 (6H, s);

MS (ESI) m/z: 532 [M+H]$^+$.

Example 12

3-Ethynyl-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid

[Formula 25]

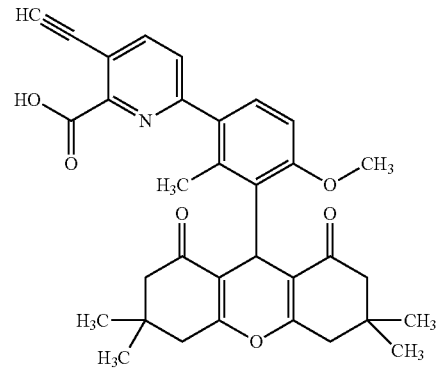

Example 12-1

Methyl 6-[4-methoxy-2-methyl-3-(3,3,6,6-tetramethyl-1,8-dioxo-2,3,4,5,6,7,8,9-octahydro-1H-xanthen-9-yl)phenyl]-3-{[(trifluoromethyl)sulfonyl]oxy}pyridine-2-carboxylate Anhydrous trifluoroacetic acid (0.361 ml, 2.20 mmol) was added to a solution of the methyl 3-hydroxy-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylate produced in Example 11-3 (1.00 g, 1.83 mmol) and pyridine (0.889 ml, 11.0 mmol) in dichloromethane (20 ml) under cooling on ice, and the mixture thus obtained was then stirred at the same temperature as above for 2.5 hours. Thereafter, water was added to the reaction solution, and the mixed solution was then extracted with dichloromethane. The organic layer thus obtained was dried over anhydrous sodium sulfate. The solvent was distilled away under reduced pressure, and the residue thus obtained was then purified by silica gel column chromatography (ethyl acetate:hexane=33:67, v/v) to obtain the title compound (1.02 g, yield: 82%).

$^1$H-NMR Spectrum (400 MHz, CDCl$_3$) δ ppm: 7.71-7.65 (2H, m), 7.27-7.25 (1H, m), 6.71 (1H, d, J=8.6 Hz), 5.06 (1H, s), 4.02 (3H, s), 3.72 (3H, s), 2.89 (3H, s), 2.50-2.34 (4H, m), 2.24-2.11 (4H, m), 1.10 (6H, s), 0.95 (6H, s).

Example 12-2

Methyl 6-[4-methoxy-2-methyl-3-(3,3,6,6-tetramethyl-1,8-dioxo-2,3,4,5,6,7,8,9-octahydro-1H-xanthen-9-yl)phenyl]-3-[(trimethylsilyl)ethynyl]pyridine-2-carboxylate A solution of the methyl 6-[4-methoxy-2-methyl-3-(3,3,6,6-tetramethyl-1,8-dioxo-2,3,4,5,6,7,8,9-octahydro-1H-xanthen-9-yl)phenyl]-3-{[(trifluoromethyl)sulfonyl]oxy}pyridine-2-carboxylate produced in Example 12-1 (800 mg, 1.47 mmol), ethynyl(trimethyl)silane (0.406 ml, 2.93 mmol), copper(I) iodide (27.9 mg, 0.15 mmol), triethylamine (0.817 ml, 5.86 mmol), and bis(triphenylphosphine)palladium(II) dichloride (103 mg, 0.15 mmol) in DMF (16 ml) was prepared at room temperature, and the solution thus prepared was then stirred at 60° C. for 2 hours. After air-cooling, water was added to the reaction solution, and the mixed solution was then extracted with ethyl acetate. The organic layer thus obtained was washed with water, and was then dried over anhydrous sodium sulfate. The solvent was distilled away under reduced pressure, and the residue thus obtained was then purified by silica gel column chromatography (ethyl acetate:hexane=33:67, v/v) to obtain the title compound (567 mg, yield: 62%).

$^1$H-NMR Spectrum (400 MHz, CDCl$_3$) δ ppm: 7.87 (1H, d, J=7.8 Hz), 7.52-7.50 (1H, m), 7.27-7.25 (1H, m), 6.68 (1H, d, J=8.6 Hz), 5.06 (1H, s), 3.97 (3H, s), 3.71 (3H, s), 2.86 (3H, s), 2.49-2.33 (4H, m), 2.22-2.10 (4H, m), 1.09 (6H, s), 0.94 (6H, s), 0.29 (9H, s).

Example 12-3

3-Ethynyl-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid Lithium hydroxide monohydrate (303 mg, 7.21 mmol) was added to a solution of the methyl 6-[4-methoxy-2-methyl-3-(3,3,6,6-tetramethyl-1,8-dioxo-2,3,4,5,6,7,8,9-octahydro-1H-xanthen-9-yl)phenyl]-3-[(trimethylsilyl)ethynyl]pyridine-2-carboxylate produced in Example 12-2 (564 mg, 0.90 mmol) in THF (11 ml) and water (5.5 ml) at room temperature, and the mixture thus obtained was then stirred at the same temperature as above for 17 hours. Thereafter, a 1 N aqueous solution of hydrochloric acid (7.21 ml) was added to the reaction solution, and water was then added thereto. The solution thus mixed was then extracted with dichloromethane. The organic layer thus obtained was dried over anhydrous sodium sulfate. The solvent was distilled away under reduced pressure, and the solid thus obtained was then washed with a mixed solution of diethyl ether and hexane, followed by collection by filtration and drying, to obtain the title compound (435 mg, yield: 89%).

$^1$H-NMR Spectrum (400 MHz, CDCl$_3$) δ ppm: 8.03 (1H, d, J=8.2 Hz), 7.68 (1H, d, J=8.2 Hz), 7.21 (1H, d, J=8.6 Hz), 6.73 (1H, d, J=8.6 Hz), 5.06 (1H, s), 3.75 (3H, s), 2.90 (3H, s), 2.52-2.35 (4H, m), 2.26-2.13 (4H, m), 1.11 (6H, s), 0.97 (6H, s);

MS (ESI) m/z: 540 [M+H]$^+$.

Example 13

3-Ethyl-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid

[Formula 26]

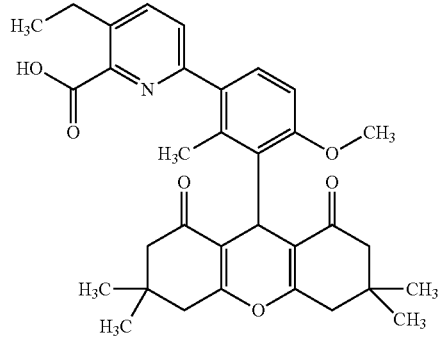

A suspension of the 3-ethynyl-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid produced in Example 12-3 (100 mg, 0.19 mmol) and 10% palladium carbon (wet) (100 mg) in methanol (2 ml) was prepared at room temperature, and the suspension thus prepared was then stirred at the same temperature as above under a hydrogen atmosphere for 2.5 hours. Thereafter, a solid was removed from the reaction solution by filtration, and the solvent was then distilled away from the filtrate thus obtained under reduced pressure. The residue thus obtained was purified by silica gel thin-layer chromatography (methanol:dichloromethane=1:10, v/v) to obtain the title compound (37.3 mg, yield: 37%).

$^1$H-NMR Spectrum (400 MHz, CDCl$_3$) δ ppm: 7.74 (1H, d, J=7.8 Hz), 7.62 (1H, d, J=7.8 Hz), 7.19-7.17 (1H, m), 6.71 (1H, d, J=8.6 Hz), 5.07 (1H, s), 3.74 (3H, s), 3.31-3.25 (2H, m), 2.89 (3H, s), 2.51-2.35 (4H, m), 2.25-2.14 (4H, m), 1.35-1.32 (3H, m), 1.11 (6H, s), 0.97 (6H, s);

MS (ESI) m/z: 544 [M+H]$^+$.

Example 14

6-[4-Methoxy-2-methyl-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide potassium salt Potassium tert-butoxide (1 mol/L THF solution, 0.58 ml, 0.58 mmol) was added dropwise to a solution of the 6-[4-methoxy-2-methyl-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide produced in Example 9 (342 mg, 0.58 mmol) in THF (7 ml) at room temperature, and the mixture thus obtained was then stirred at the same temperature as above for 20 minutes. Thereafter, diethyl ether was added to the reaction solution, and the precipitated solid was collected by filtration and was then dried to obtain the title compound (254 mg, yield: 70%).

$^1$H-NMR Spectrum (400 MHz, CDCl$_3$) δ ppm: 8.12 (1H, d, J=7.8 Hz), 7.72-7.68 (1H, m), 7.36-7.35 (1H, m), 7.05-7.03 (1H, m), 6.70 (1H, d, J=8.6 Hz), 4.88 (1H, s), 3.72 (3H, s), 2.85 (3H, s), 2.62 (3H, s), 2.47-2.33 (4H, m), 2.22-2.11 (4H, m), 1.06 (6H, s), 0.96 (6H, s);

MS (ESI) m/z: 593 [M+H]$^+$;

Anal. Calcd for $C_{32}H_{35}KN_2O_7S$: C, 60.93; H, 5.59; N, 4.44; S, 5.08; K, 6.20. Found: C, 57.78; H, 5.71; N, 4.12; S, 5.25; K, 6.47.

Example 15

1-{6-[4-Methoxy-3-(3,3,6,6-tetramethyl-1,8-dioxo-2,3,4,5,6,7,8,9-octahydro-1H-xanthen-9-yl)phenyl]pyridin-2-yl}-D-proline

[Formula 27]

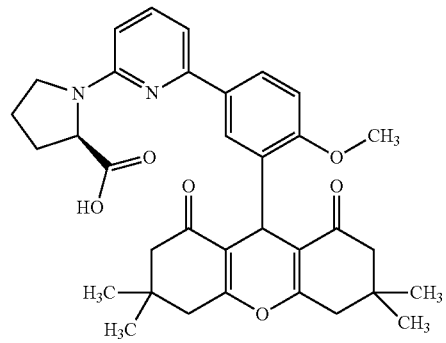

Example 15-1

Methyl 1-(6-bromopyridin-2-yl)-D-prolinate

Triethylamine (1.91 mL, 13.7 mmol) and D-proline methyl hydrochloride (1.13 g, 6.84 mmol) were added to a solution of 2-bromo-6-fluoropyridine (802 mg, 4.55 mmol) in 1,4-dioxane (9 mL) at room temperature. The mixture thus obtained was stirred at the same temperature as above for 30 minutes, and then at 80° C. for 3 hours. Thereafter, triethylamine (951 uL, 6.84 mmol) was further added to the resulting solution at room temperature, and the mixture thus obtained was then stirred at 80° C. for 2 hours. Thereafter, water was added to the reaction solution, and the mixed solution was then extracted with ethyl acetate three times. The organic layer thus obtained was dried over anhydrous magnesium sulfate, and the solvent was then distilled away under reduced pressure. The residue thus obtained was purified by silica gel column chromatography (hexane:ethyl acetate=9:1 to 1:1, v/v) to obtain the title compound (213 mg, yield: 16%).

$^1$H-NMR Spectrum (500 MHz, CDCl$_3$) δ ppm: 7.32-7.25 (1H, m), 6.74 (1H, d, J=7.32 Hz), 6.32 (1H, d, J=8.30 Hz), 4.59-4.51 (1H, m), 3.78 (3H, s), 3.68-3.61 (1H, m), 3.53-3.45 (1H, m), 2.37-2.28 (1H, m), 2.22-2.05 (3H, m).

Example 15-2

Methyl 1-{6-[4-methoxy-3-(3,3,6,6-tetramethyl-1,8-dioxo-2,3,4,5,6,7,8,9-octahydro-1H-xanthen-9-yl)phenyl]pyridin-2-yl}-D-prolinate Sodium carbonate (238 mg, 2.24 mmol) and tetrakistriphenylphosphine palladium(0) (86.3 mg, 74.7μμmol) were added to a solution of the methyl 1-(6-bromopyridin-2-yl)-D-prolinate (213 mg, 747 μmol) obtained in Example 15-1 and the [4-methoxy-3-(3,3,6,6-tetramethyl-1,8-dioxo-2,3,4,5,6,7,8,9-octahydro-1H-xanthen-9-yl)phenyl]boronic acid (317 mg, 747 μmol) obtained in Example 1-1 in dimethoxyethane/water (3:1, v/v) (4 mL) at room temperature. The mixture thus obtained was stirred at 80° C. for 4 hours. Thereafter, water was added to the reaction solution, and the mixed solution was then extracted with ethyl acetate three times. The organic layer thus obtained was dried over anhydrous magnesium sulfate, and the solvent was then distilled away under reduced pressure. The residue thus obtained was purified by silica gel column chromatography (hexane:ethyl acetate=8:2 to 1:3, v/v) to obtain the title compound (190 mg, yield: 44%).

$^1$H-NMR Spectrum (400 MHz, CDCl$_3$) δ ppm: 7.93 (1H, s), 7.87 (1H, d, J=8.21 Hz), 7.49 (1H, t, J=7.82 Hz), 7.09 (1H, d, J=7.43 Hz), 6.84 (1H, d, J=8.61 Hz), 6.30 (1H, d, J=8.23 Hz), 4.98 (1H, s), 4.73 (1H, m), 3.85 (3H, s), 3.74 (3H, s), 3.73-3.66 (1H, m), 3.56-3.48 (1H, m), 2.52-2.05 (8H, m), 1.11 (6H, s), 0.98 (6H, s);
MS (ESI) m/z: 585 [M+H]$^+$.

Example 15-3

1-{6-[4-Methoxy-3-(3,3,6,6-tetramethyl-1,8-dioxo-2,3,4,5,6,7,8,9-octahydro-1H-xanthen-9-yl)phenyl]pyridin-2-yl}-D-proline Lithium hydroxide (16.9 mg, 403 μmol) was added to a solution of the methyl 1-{6-[4-methoxy-3-(3,3,6,6-tetramethyl-1,8-dioxo-2,3,4,5,6,7,8,9-octahydro-1H-xanthen-9-yl)phenyl]pyridin-2-yl}-D-prolinate obtained in Example 15-2 (157 mg, 269 μmol) in a mixed solvent of THF/water (2:1, v/v) (3 mL) at room temperature. The mixture thus obtained was stirred at the same temperature as above for 30 minutes, and was further stirred at 60° C. for 1 hour. Thereafter, water and diethyl ether were added to the reaction solution, and the mixed solution was then extracted with water twice. The resultant was washed with diethyl ether. Thereafter, 1 N hydrochloric acid was added to the water layer thus obtained, so that the pH was adjusted to pH 4 or lower, and the mixed solution was then extracted with ethyl acetate three times. The organic layer thus obtained was dried over anhydrous magnesium sulfate, and the solvent was then distilled away under reduced pressure. The residue obtained was crystallized from hexane/ethyl acetate to obtain the title compound (107 mg, yield: 70%).

$^1$H-NMR Spectrum (500 MHz, CDCl$_3$) δ ppm: 7.85 (1H, d, J=2.34 Hz), 7.69-7.61 (2H, m), 7.18 (1H, d, J=7.43 Hz), 6.89 (1H, d, J=8.61 Hz), 6.48 (1H, d, J=8.21 Hz), 5.01 (1H, s), 4.57 (1H, d, J=7.82 Hz), 3.90 (3H, s), 3.49 (1H, t, J=7.4 Hz), 3.45-3.38 (1H, m), 2.79 (1H, dd, J=12.1, 5.48 Hz), 2.55-2.41 (4H, m), 2.24-2.10 (6H, m), 2.01-1.90 (1H, m), 1.11 (3H, s), 1.11 (3H, s), 1.00 (3H, s), 0.99 (3H, s);
MS (ESI) m/z: 571 [M+H]$^+$.

Example 16

6-[4-Methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide

[Formula 28]

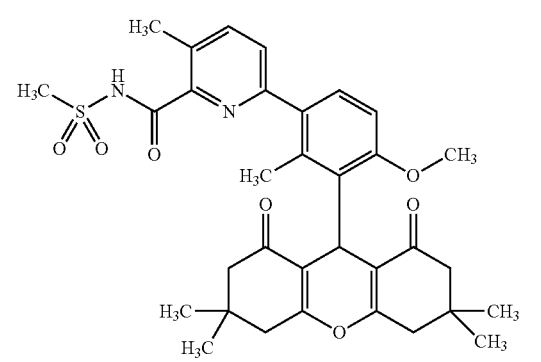

1,1'-Carbonyldiimidazole (99.5 mg, 0.61 mmol) was added to a solution of the 6-[4-methoxy-2-methyl-3-(3,3,6,6-tetramethyl-1,8-dioxo-2,3,4,5,6,7,8,9-octahydro-1H-xanthen-9-yl)phenyl]-3-methylpyridine-2-carboxylic acid produced in Example 10-3 (250 mg, 0.47 mmol) in DMF (5 ml) at room temperature, and the mixture thus obtained was then stirred at the same temperature as above for 1 hour and 45 minutes. Thereafter, methanesulfonamide (58.4 mg, 0.61 mmol) and 1,8-diazabicyclo[5.4.0]undec-7-ene (0.092 ml, 0.61 mmol) were added to the resulting solution at room temperature, and the mixture thus obtained was then stirred at the same temperature as above for 4 hours. Thereafter, an aqueous solution of citric acid (454 mg, 2.36 mmol) was added to the reaction solution, and the mixed solution was then extracted with ethyl acetate. The organic layer thus obtained was washed with water, and was then dried over anhydrous sodium sulfate. The solvent was distilled away under reduced pressure, and the residue thus obtained was then purified by silica gel column chromatography (methanol:dichloromethane=0:1 to 1:9, v/v). The solid thus obtained was washed with diethyl ether, followed by collection by filtration and drying, to obtain the title compound (240 mg, yield: 84%).

$^1$H-NMR Spectrum (400 MHz, CDCl$_3$) δ ppm: 7.66 (1H, d, J=8.6 Hz), 7.59-7.57 (1H, m), 7.18 (1H, d, J=8.6 Hz), 6.72 (1H, d, J=8.6 Hz), 5.06 (1H, s), 3.74 (3H, s), 3.39 (3H, s), 2.86 (3H, s), 2.78 (3H, s), 2.51-2.35 (4H, m), 2.25-2.14 (4H, m), 1.11 (6H, s), 0.98 (6H, s);

MS (ESI) m/z: 607 [M+H]$^+$.

Example 17

3-Ethyl-6-[4-methoxy-2-methyl-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide

[Formula 29]

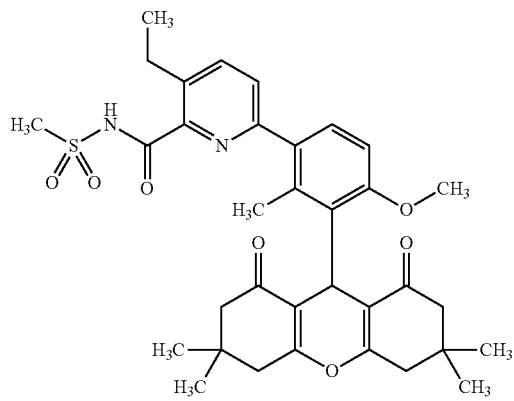

1,1'-Carbonyldiimidazole (104 mg, 0.64 mmol) was added to a solution of the 3-ethyl-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid produced in Example 13 (267 mg, 0.49 mmol) in DMF (5.3 ml) at room temperature, and the mixture thus obtained was then stirred at the same temperature as above for 1.5 hours. Thereafter, methanesulfonamide (60.7 mg, 0.64 mmol) and 1,8-diazabicyclo[5.4.0]undec-7-ene (0.096 ml, 0.64 mmol) were added to the resulting solution at room temperature, and the mixture thus obtained was then stirred at the same temperature as above for 3 hours. Thereafter, an aqueous solution of citric acid (472 mg, 2.46 mmol) was added to the reaction solution, and the mixed solution was then extracted with ethyl acetate. The organic layer thus obtained was washed with water, and was then dried over anhydrous sodium sulfate. The solvent was distilled away under reduced pressure, and the residue thus obtained was then purified by silica gel column chromatography (methanol:dichloromethane=0:1 to 1:9, v/v). The solid thus obtained was washed with diethyl ether, followed by collection by filtration and drying, to obtain the title compound (128 mg, yield: 42%).

$^1$H-NMR Spectrum (400 MHz, CDCl$_3$) δ ppm: 7.70 (1H, d, J=8.2 Hz), 7.61 (1H, d, J=8.2 Hz), 7.19 (1H, d, J=8.6 Hz), 6.73 (1H, d, J=8.6 Hz), 5.06 (1H, s), 3.74 (3H, s), 3.39 (3H, s), 3.26-3.20 (2H, m), 2.86 (3H, s), 2.51-2.35 (4H, m), 2.25-2.14 (4H, m), 1.35-1.31 (3H, m), 1.11 (6H, s), 0.98 (6H, s);

MS (ESI) m/z: 621 [M+H]$^+$.

Example 18

6-[4-methoxy-2-methyl-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide 2-methylpropan-2-amine salt 2-Methylpropan-2-amine (0.075 ml, 0.71 mmol) was added to a suspension of the 6-[4-methoxy-2-methyl-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide produced in Example 9 (209 mg, 0.35 mmol) in ethanol (2 ml) at room temperature, and the mixture thus obtained was then stirred at the same temperature as above for 30 minutes. Thereafter, diethyl ether was added to the reaction solution, and the solid thus generated was collected by filtration and was then dried to obtain the title compound (218 mg, yield: 93%).

$^1$H-NMR Spectrum (400 MHz, CDCl$_3$) δ ppm: 8.29-8.27 (1H, m), 7.90-7.86 (1H, m), 7.47-7.44 (1H, m), 7.15 (1H, d, J=8.2 Hz), 6.70 (1H, d, J=8.6 Hz), 4.99 (1H, s), 3.73 (3H, s), 3.27 (3H, s), 2.71 (3H, s), 2.55-2.37 (4H, m), 2.31-2.10 (4H, m), 1.13 (6H, s), 0.96 (6H, s), 0.92 (9H, s);

MS (ESI) m/z: 593 [M+H]$^+$;

Anal. Calcd for C$_{36}$H$_{47}$N$_3$O$_7$S: C, 64.93; H, 7.11; N, 6.31; S, 4.81. Found: C, 64.64; H, 6.98; N, 6.25; S, 4.77.

Example 19

6-[4-Methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide sodium salt A 1 N aqueous solution of sodium hydroxide (4.94 ml) was added to a suspension of the 6-[4-methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide produced in Example 16 (3.00 g, 4.94 mmol) in water (30 ml) at room temperature, and the mixture thus obtained was then stirred at the same temperature as above for 24 hours. Thereafter, the residue was removed from the reaction solution by filtration, and the filtrate thus obtained was then freeze-dried to obtain the title compound (3.04 g, yield: 98%).

$^1$H-NMR Spectrum (400 MHz, CDCl$_3$) δ ppm: 7.52 (1H, d, J=7.8 Hz), 7.25 (1H, d, J=7.8 Hz), 6.96 (1H, d, J=8.6 Hz), 6.61 (1H, d, J=8.6 Hz), 4.90 (1H, s), 3.67 (3H, s), 2.85 (3H, s), 2.65 (3H, s), 2.58 (3H, s), 2.46-2.30 (4H, m), 2.27 (2H, m), 2.13 (2H, m), 1.05 (6H, s), 0.92 (6H, s);

MS (ESI) m/z: 607 [M+H]$^+$;

Anal. Calcd for C$_{33}$H$_{37}$N$_2$NaO$_7$S: C, 63.04; H, 5.93; N, 4.46; S, 5.10; Na, 3.66. Found: C, 60.51; H, 6.19; N, 4.32; S, 5.31; Na, 3.83.

Example 20

6-[4-Methoxy-2-methyl-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide hemi-calcium salt A solution of calcium chloride (95%, 41.5 mg, 0.35 mmol) in water (0.5 ml) was added to a solution of the 6-[4-methoxy-2-methyl-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide potassium salt produced in Example 14 (407 mg, 0.65 mmol) in water (8 ml) at room temperature, and the mixture thus obtained was then stirred at 40° C. for 5 hours. Thereafter, the solid thus generated was collected by filtration and was then dried to obtain the title compound (322 mg, yield: 82%).

$^1$H-NMR Spectrum (400 MHz, DMSO-D$_6$) δ ppm: 7.87-7.78 (2H, m), 7.30-7.28 (1H, m), 7.05 (1H, d, J=8.2 Hz), 6.81 (1H, d, J=8.6 Hz), 4.86 (1H, s), 3.69 (3H, s), 2.87 (3H, s), 2.68 (3H, s), 2.60-2.37 (4H, m), 2.27-2.03 (4H, m), 1.04 (6H, s), 0.88 (6H, s);

MS (ESI) m/z: 593 [M+H]$^+$;

Anal. Calcd for C$_{64}$H$_{70}$CaN$_4$O$_{14}$S$_2$: C, 62.82; H, 5.77; N, 4.58; S, 5.24; Ca, 3.28. Found: C, 57.67; H, 6.31; N, 4.19; S, 4.80; Ca, 3.26.

Example 21

6-[4-Methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide hemi-calcium salt A solution of calcium chloride (95%, 36.7 mg, 0.31 mmol) in water (0.5 ml) was added to a solution of the 6-[4-methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide sodium salt produced in Example 19 (395 mg, 0.63 mmol) in water (8 ml) at room temperature, and the mixture thus obtained was then stirred at 40° C. for 5 hours. Thereafter, the solid thus generated was collected by filtration and was then dried to obtain the title compound (326 mg, yield: 83%).

$^1$H-NMR Spectrum (400 MHz, DMSO-D$_6$) δ ppm: 7.56 (1H, d, J=7.8 Hz), 7.10 (1H, d, J=7.8 Hz), 7.01 (1H, d, J=8.6 Hz), 6.78 (1H, d, J=8.6 Hz), 4.85 (1H, s), 3.67 (3H, s), 2.88 (3H, s), 2.69 (3H, s), 2.59-2.36 (4H, m), 2.31 (3H, s), 2.26-2.02 (4H, m), 1.04 (6H, s), 0.87 (6H, s);

MS (ESI) m/z: 607 [M+H]$^+$;

Anal. Calcd for C$_{66}$H$_{74}$CaN$_4$O$_{14}$S$_2$: C, 63.33; H, 5.96; N, 4.48; S, 5.12; Ca, 3.20. Found: C, 60.62; H, 6.29; N, 4.32; S, 5.00; Ca, 3.45.

Example 22

9-{3-[6-(Hydroxymethyl)pyridin-2-yl]-2-methoxyphenyl}-3,3,6,6-tetramethyl-3,4,5,6,7,9-hexahydro-1H-xanthene-1,8(2H)-dione

[Formula 30]

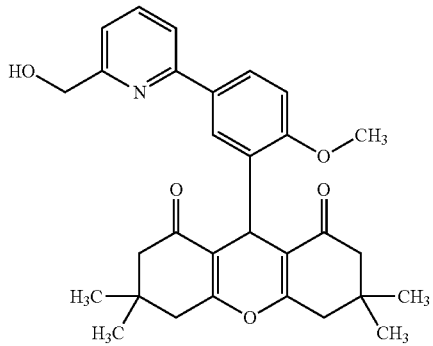

1,1'-Carbonyldiimidazole (38.8 mg, 0.239 mol) was added to a solution of the 6-[4-methoxy-3-(3,3,6,6-tetramethyl-1,8-dioxo-2,3,4,5,6,7,8,9-octahydro-1H-xanthen-9-yl)phenyl]pyridine-2-carboxylic acid obtained in Example 1-2 (100 mg, 0.199 mmol) in THF (1.0 mL) at room temperature, and the mixture thus obtained was then stirred at the same temperature as above for 30 minutes. Subsequently, the reaction solution was cooled to 0° C., sodium borohydride (7.5 mg, 0.199 mmol) and water (0.1 mL) were then added thereto, and the mixture thus obtained was then stirred at the same temperature as above for 30 minutes. Thereafter, a saturated aqueous solution of ammonium chloride was added to the reaction solution, and the mixed solution was then extracted with ethyl acetate twice. The organic layer thus obtained was washed with brine, and was then dried over anhydrous sodium sulfate. The solvent was distilled away under reduced pressure. The residue thus obtained was purified by silica gel column chromatography (hexane:ethyl acetate=3:1 to 3:7, v/v), and was then solidified with a mixed solution of diethyl ether-hexane to obtain the title compound (76.3 mg, yield: 78%).

$^1$H-NMR Spectrum (500 MHz, CDCl$_3$) δ ppm: 8.00 (1H, d, J=2.4 Hz), 7.87 (1H, dd, J=8.8, 2.4 Hz), 7.69 (1H, dd, J=7.8, 7.3 Hz), 7.65 (1H, d, J=7.8 Hz), 7.03 (1H, d, J=7.3 Hz), 6.88 (1H, d, J=8.8 Hz), 4.97 (1H, s), 4.76 (2H, s), 4.32 (1H, s), 3.85 (3H, s), 2.48 (2H, d, J=17.6 Hz), 2.40 (2H, d, J=17.6 Hz), 2.22 (2H, d, J=16.6 Hz), 2.14 (2H, d, J=16.6 Hz), 1.10 (6H, s), 0.96 (6H, s);

MS (ESI) m/z: 488 [M+H]$^+$.

Example 23

3-Methoxy-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid $^1$H-NMR Spectrum (400 MHz, CDCl$_3$) δ ppm: 7.68 (1H, d, J=8.6 Hz), 7.50 (1H, d, J=8.6 Hz), 7.18-7.16 (1H, m), 6.70 (1H, d, J=8.6 Hz), 5.06 (1H, s), 4.05 (3H, s), 3.73 (3H, s), 2.87 (3H, s), 2.51-2.35 (4H, m), 2.25-2.13 (4H, m), 1.11 (6H, s), 0.97 (6H, s);

MS (ESI) m/z: 544 [M−H]$^−$.

Example 24

3-Methoxy-6-[4-methoxy-3-(3,3,6,6-tetramethyl-1,8-dioxo-2,3,4,5,6,7,8,9-octahydro-1H-xanthen-9-yl)phenyl]pyridine-2-carboxylic acid $^1$H-NMR Spectrum (500 MHz, CDCl$_3$) δ ppm: 8.04-8.02 (1H, m), 7.94-7.94 (1H, m), 7.75-7.72 (1H, m), 7.54-7.52 (1H, m), 6.88 (1H, d, J=8.8 Hz), 4.92 (1H, s), 4.04 (3H, s), 3.83 (3H, s), 2.51-2.38 (4H, m), 2.25-2.13 (4H, m), 1.11 (6H, s), 0.96 (6H, s);

MS (ESI) m/z: 530 [M−H]$^−$.

Example 25

3-Chloro-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid $^1$H-NMR Spectrum (400 MHz, CDCl$_3$) δ ppm: 7.90 (1H, d, J=8.2 Hz), 7.64 (1H, d, J=8.2 Hz), 7.19-7.17 (1H, m), 6.73 (1H, d, J=8.6 Hz), 5.06 (1H, s), 3.74 (3H, s), 2.89 (3H, s), 2.51-2.35 (4H, m), 2.26-2.13 (4H, m), 1.11 (6H, s), 0.97 (6H, s);

MS (ESI) m/z: 548 [M−H]$^−$.

Example 26

3-Fluoro-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid $^1$H-NMR Spectrum (400 MHz, CDCl$_3$) δ ppm: 7.75-7.72 (1H, m), 7.67-7.63 (1H, m), 7.16 (1H, d, J=8.6 Hz), 6.72 (1H, d, J=8.6 Hz), 5.05 (1H, s), 3.74 (3H, s), 2.87 (3H, s), 2.52-2.35 (4H, m), 2.26-2.13 (4H, m), 1.11 (6H, s), 0.97 (6H, s);
MS (ESI) m/z: 532 [M−H]$^-$.

Example 27

3-(Benzyloxy)-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid $^1$H-NMR Spectrum (500 MHz, CDCl$_3$) δ ppm: 7.61-7.59 (1H, m), 7.57-7.55 (2H, m), 7.49-7.47 (1H, m), 7.42-7.39 (2H, m), 7.34-7.32 (1H, m), 7.16 (1H, d, J=8.3 Hz), 6.69 (1H, d, J=8.3 Hz), 5.36 (2H, s), 5.05 (1H, s), 3.73 (3H, s), 2.86 (3H, s), 2.50-2.35 (4H, m), 2.24-2.13 (4H, m), 1.11 (6H, s), 0.96 (6H, s);
MS (ESI) m/z: 622 [M+H]$^+$.

Example 28

3-Ethoxy-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid $^1$H-NMR Spectrum (400 MHz, CDCl$_3$) δ ppm: 7.65 (1H, d, J=8.6 Hz), 7.47 (1H, d, J=8.6 Hz), 7.17 (1H, d, J=8.6 Hz), 6.70 (1H, d, J=8.6 Hz), 5.06 (1H, s), 4.31-4.25 (2H, m), 3.73 (3H, s), 2.87 (3H, s), 2.51-2.35 (4H, m), 2.25-2.13 (4H, m), 1.59-1.55 (3H, m), 1.11 (6H, s), 0.97 (6H, s);
MS (ESI) m/z: 560 [M+H]$^+$.

Example 29

3-(2-Methoxyethoxy)-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid $^1$H-NMR Spectrum (400 MHz, CDCl$_3$) δ ppm: 7.65 (1H, d, J=8.6 Hz), 7.55 (1H, d, J=8.6 Hz), 7.18-7.16 (1H, m), 6.70 (1H, d, J=8.6 Hz), 5.06 (1H, s), 4.36-4.34 (2H, m), 3.90-3.88 (2H, m), 3.73 (3H, s), 3.51 (3H, s), 2.87 (3H, s), 2.50-2.35 (4H, m), 2.25-2.13 (4H, m), 1.11 (6H, s), 0.97 (6H, s);
MS (ESI) m/z: 590 [M+H]$^+$.

Example 30

6-[4-Methoxy-3-(3,3,6,6-tetramethyl-1,8-dioxo-2,3,4,5,6,7,8,9-octahydro-1H-xanthen-9-yl)phenyl]-3-methylpyridine-2-carboxylic acid $^1$H-NMR Spectrum (400 MHz, CDCl$_3$) δ ppm: 7.99 (1H, d, J=2.3 Hz), 7.91 (1H, d, J=8.2 Hz), 7.79-7.76 (1H, m), 7.73-7.71 (1H, m), 6.89 (1H, d, J=8.6 Hz), 4.94 (1H, s), 3.85 (3H, s), 2.77 (3H, s), 2.52-2.38 (4H, m), 2.26-2.12 (4H, m), 1.11 (6H, s), 0.96 (6H, s);
MS (ESI) m/z: 514 [M−H]$^-$.

Example 31

6-[4-Methoxy-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide $^1$H-NMR Spectrum (500 MHz, CDCl$_3$) δ ppm: 7.96-7.95 (1H, m), 7.93-7.91 (1H, m), 7.82-7.79 (1H, m), 7.69 (1H, d, J=8.1 Hz), 6.90 (1H, d, J=8.5 Hz), 4.93 (1H, s), 3.84 (3H, s), 3.41 (3H, s), 2.75 (3H, s), 2.50-2.41 (4H, m), 2.25-2.13 (4H, m), 1.10 (6H, s), 0.96 (6H, s);
MS (ESI) m/z: 593 [M+H]$^+$.

Example 32

6-[4-Methoxy-2-methyl-3-(3,3,6,6-tetramethyl-1,8-dioxo-2,3,4,5,6,7,8,9-octahydro-1H-xanthen-9-yl)phenyl]-4-methylpyridine-2-carboxylic acid

[Formula 31]

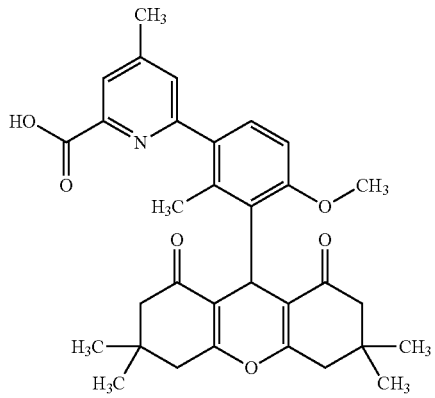

Example 32-1

Tert-butyl 6-chloro-4-methylpyridine-2-carboxylate p-Toluenesulfonyl chloride (1.11 g, 5.83 mmol) was added to a solution of 6-chloro-4-methylpyridine-2-carboxylic acid (0.50 g, 27.6 mmol) as a known compound in tert-butyl alcohol (16.5 ml) and pyridine (2.4 ml) at room temperature, and the mixture thus obtained was then stirred at the same temperature as above for 22 hours. Thereafter, a solution of sodium hydrogen carbonate (1.22 g, 14.6 mmol) in water (33 ml) was added to the resulting solution, and the mixture thus obtained was then stirred. The solvent was distilled away from the reaction solution under reduced pressure. Water was added to the residue thus obtained, and the mixed solution was then extracted with ethyl acetate. The organic layer thus obtained was dried over anhydrous sodium sulfate, and the solvent was then distilled away under reduced pressure to obtain the title compound (0.506 g, yield: 76%).

$^1$H-NMR Spectrum (500 MHz, CDCl$_3$) δ ppm: 7.76 (1H, m), 7.29 (1H, m), 2.41 (3H, m), 1.62 (9H, m).

Example 32-2

Tert-butyl 6-(3-formyl-4-methoxy-2-methylphenyl)-4-methylpyridine-2-carboxylate

A suspension of the 6-methoxy-2-methyl-3-(4,4,5,5-tetramethyl-1,3,2-dioxaborolan-2-yl)benzaldehyde produced in Example 4-1 (500 mg, 1.81 mmol), the tert-butyl 6-chloro-4-methylpyridine-2-carboxylate produced in Example 32-1 (412 mg, 1.81 mmol), sodium carbonate (576 mg, 5.43 mmol), and tetrakis(triphenylphosphine)palladium(0) (105 mg, 0.09 mmol) in 1,2-dimethoxyethane (10 ml) and water (4.4 ml) was prepared at room temperature. The suspension thus obtained was stirred at 90° C. for 2 hours. After air-cooling, water was added to the reaction solution, and the mixed solution was then extracted with ethyl acetate. The organic layer thus obtained was dried over anhydrous sodium sulfate. The solvent was distilled away under reduced pressure, and the residue thus obtained was then purified by silica gel column chromatography (ethyl acetate:dichloromethane=1:9, v/v) to obtain the title compound (769 mg, yield: 124%).

$^1$H-NMR Spectrum (400 MHz, CDCl$_3$) δ ppm: 10.68 (1H, s), 7.79 (1H, m), 7.61 (1H, d, J=8.6 Hz), 7.28 (1H, m), 6.91 (1H, d, J=8.6 Hz), 3.94 (3H, s), 2.51 (3H, s), 2.46 (3H, s), 1.63 (9H, s).

Example 32-3

6-[4-Methoxy-2-methyl-3-(3,3,6,6-tetramethyl-1,8-dioxo-2,3,4,5,6,7,8,9-octahydro-1H-xanthen-9-yl)phenyl]-4-methylpyridine-2-carboxylic acid Pyrrolidine (0.015 ml, 0.18 mmol) was added to a suspension of the tert-butyl 6-(3-formyl-4-methoxy-2-methylphenyl)-4-methylpyridine-2-carboxylate produced in Example 32-2 (762 mg) and 5,5-dimethylcyclohexane-1,3-dione (584 mg, 4.16 mmol) in ethanol (15 ml) at room temperature, and the mixture thus obtained was then stirred at 80° C. for 2.5 hours. After air-cooling, the solvent was distilled away from the reaction solution under reduced pressure. The residue thus obtained was dissolved in chloroform (15 ml), and p-toluenesulfonic acid monohydrate (93.5 mg, 0.54 mmol) was then added to the solution obtained above at room temperature. The mixture thus obtained was then stirred at 70° C. for 2.5 hours. After air-cooling, water was added to the reaction solution, and the mixed solution was then extracted with dichloromethane. The organic layer thus obtained was dried over anhydrous sodium sulfate. The solvent was distilled away under reduced pressure, and the residue thus obtained was then dissolved in dichloromethane (27 ml). After that, trifluoroacetic acid (13.5 ml) was added to the solution obtained above at room temperature, and the mixture thus obtained was then stirred at the same temperature as above for 3.5 hours. Thereafter, the solvent was distilled away from the reaction solution under reduced pressure. A small amount of saturated aqueous solution of sodium hydrogen carbonate was added to the obtained residue, and a 10% aqueous solution of citric acid was then added to the resulting solution. The solution thus mixed was extracted with dichloromethane. The organic layer thus obtained was dried over anhydrous sodium sulfate, and the solvent was then distilled away under reduced pressure. The residue thus obtained was dissolved in THF (27 ml), and a 1 N aqueous solution of sodium hydroxide (3.98 ml) was then added to the solution obtained above. The mixture thus obtained was stirred at room temperature. Thereafter, water was added to the reaction solution, and the mixed solution was then washed with diethyl ether. A 1 N aqueous solution of hydrochloric acid (3.98 ml) was added to the water layer thus obtained, and the mixed solution was then extracted with dichloromethane. The organic layer thus obtained was dried over anhydrous sodium sulfate. The solvent was distilled away under reduced pressure, and ethanol was then added to the residue. The solid thus obtained was collected by filtration and was then dried to obtain the title compound (0.515 g, yield: 54%).

$^1$H-NMR Spectrum (400 MHz, CDCl$_3$) δ ppm: 7.98 (1H, s), 7.49 (1H, s), 7.17-7.15 (1H, m), 6.71 (1H, d, J=8.6 Hz), 5.07 (1H, s), 3.74 (3H, s), 2.86 (3H, s), 2.51-2.35 (4H, m), 2.49 (3H, s), 2.26-2.13 (4H, m), 1.11 (6H, s), 0.97 (6H, s)

MS (ESI) m/z: 528 [M−H]$^-$.

Example 33

3-Methoxy-6-[4-methoxy-2-methyl-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide $^1$H-NMR Spectrum (400 MHz, CDCl$_3$) δ ppm: 7.67 (1H, d, J=8.6 Hz), 7.48-7.46 (1H, m), 7.19-7.16 (1H, m), 6.72 (1H, d, J=8.2 Hz), 5.05 (1H, s), 4.03 (3H, s), 3.74 (3H, s), 3.40 (3H, s), 2.85 (3H, s), 2.51-2.35 (4H, m), 2.25-2.13 (4H, m), 1.11 (6H, s), 0.97 (6H, s);

MS (ESI) m/z: 623 [M+H]$^+$.

Example 34

6-[4-Methoxy-2-methyl-3-(3,3,6,6-tetramethyl-1,8-dioxo-2,3,4,5,6,7,8,9-octahydro-1H-xanthen-9-yl)phenyl]-5-methylpyridine-2-carboxylic acid $^1$H-NMR Spectrum (400 MHz, CDCl$_3$) δ ppm: 8.10 (1H, d, J=7.8 Hz), 7.80-7.78 (1H, m), 6.97-6.95 (1H, m), 6.72 (1H, d, J=8.6 Hz), 5.00 (1H, s), 3.74 (3H, s), 2.61 (3H, s), 2.50-2.36 (4H, m), 2.23 (3H, s), 2.23-2.12 (4H, m), 1.11 (6H, s), 1.00-0.98 (6H, m);

MS (ESI) m/z: 528 [M−H]$^-$.

Example 35

6-[4-Methoxy-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide potassium salt $^1$H-NMR Spectrum (400 MHz, CDCl$_3$) δ ppm: 8.00 (1H, s), 7.48-7.40 (2H, m), 7.26 (1H, m), 6.79 (1H, d, J=8.6 Hz), 4.68 (1H, s), 3.72 (3H, s), 2.98 (3H, s), 2.50 (3H, s), 2.48-2.29 (4H, m), 2.22-2.12 (4H, m), 1.07 (6H, s), 0.92 (6H, s);

MS (ESI) m/z: 593 [M+H]$^+$;

Anal. Calcd for $C_{32}H_{35}KN_2O_7S$: C, 60.92; H, 5.59; N, 4.44; S, 5.08; K, 6.20. Found: C, 55.68; H, 5.86; N, 4.08; S, 4.56; K, 7.60.

Example 36

N-(Ethylsulfonyl)-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxamide $^1$H-NMR Spectrum (400 MHz, CDCl$_3$) δ ppm: 8.14-8.12 (1H, m), 7.93-7.89 (1H, m), 7.70-7.68 (1H, m), 7.22 (1H, d, J=8.6 Hz), 6.74 (1H, d, J=8.6 Hz), 5.07 (1H, s), 3.75 (3H, s), 3.58 (2H, q, J=7.4 Hz), 2.87 (3H, s), 2.51-2.36 (4H, m), 2.25-2.14 (4H, m), 1.46 (3H, t, J=7.4 Hz), 1.11 (6H, s), 0.98 (6H, s);

MS (ESI) m/z: 607 [M+H]$^+$.

Example 37

6-[4-Methoxy-2-methyl-3-(3,3,6,6-tetramethyl-1,8-dioxo-2,3,4,5,6,7,8,9-octahydro-1H-xanthen-9-yl)phenyl]-N-(propan-2-ylsulfonyl)pyridine-2-carboxamide $^1$H-NMR Spectrum (400 MHz, CDCl$_3$) δ ppm: 8.14-8.11 (1H, m), 7.92-7.88 (1H, m), 7.70-7.68 (1H, m), 7.23 (1H, d, J=8.6 Hz), 6.75 (1H, d, J=8.6 Hz), 5.07 (1H, s), 3.97-3.90 (1H, m), 3.75 (3H, s), 2.88 (3H, s), 2.51-2.36 (4H, m), 2.25-2.14 (4H, m), 1.49 (6H, d, J=7.0 Hz), 1.11 (6H, s), 0.98 (6H, s);

MS (ESI) m/z: 621 [M+H]$^+$.

Example 38

6-[4-Methoxy-2-methyl-3-(3,3,6,6-tetramethyl-1,8-dioxo-2,3,4,5,6,7,8,9-octahydro-1H-xanthen-9-yl)phenyl]-N-(propylsulfonyl)pyridine-2-carboxamide $^1$H-NMR Spectrum (400 MHz, CDCl$_3$) δ ppm: 8.14-8.11 (1H, m), 7.92-7.88 (1H, m), 7.70-7.68 (1H, m), 7.21 (1H, d, J=8.6 Hz), 6.74 (1H, d, J=8.6 Hz), 5.06 (1H, s), 3.75 (3H, s), 3.55-3.45 (2H, m), 2.87 (3H, s), 2.51-2.36 (4H, m), 2.25-2.14 (4H, m), 1.99-1.90 (2H, m), 1.11 (6H, s), 1.11-1.07 (3H, m), 0.98 (6H, s);

MS (ESI) m/z: 621 [M+H]$^+$.

Example 39

N-[(2-Methoxyethyl)sulfonyl]-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxamide $^1$H-NMR Spectrum (400 MHz, CDCl$_3$) δ ppm: 8.14-8.12 (1H, m), 7.92-7.88 (1H, m), 7.70-7.67 (1H, m), 7.22-7.19 (1H, m), 6.74 (1H, d, J=8.6 Hz), 5.06 (1H, s), 3.89-3.86 (2H, m), 3.81-3.78 (2H, m), 3.75 (3H, s), 3.29 (3H, s), 2.87 (3H, s), 2.51-2.36 (4H, m), 2.25-2.14 (4H, m), 1.11 (6H, s), 0.98 (6H, s);

MS (ESI) m/z: 637 [M+H]$^+$.

Example 40

6-[4-Methoxy-2-methyl-3-(3,3,6,6-tetramethyl-1,8-dioxo-2,3,4,5,6,7,8,9-octahydro-1H-xanthen-9-yl)phenyl]-4-methyl-N-(methylsulfonyl)pyridine-2-carboxamide

[Formula 32]

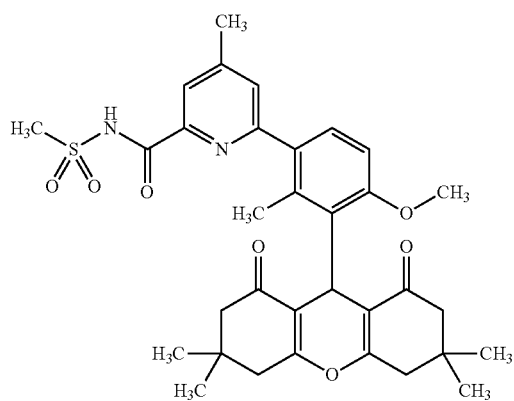

1,1'-Carbonyldiimidazole (99.5 mg, 0.61 mmol) was added to a solution of the 6-[4-methoxy-2-methyl-3-(3,3,6,6-tetramethyl-1,8-dioxo-2,3,4,5,6,7,8,9-octahydro-1H-xanthen-9-yl)phenyl]-4-methylpyridine-2-carboxylic acid produced in Example 32-3 (250 mg, 0.47 mmol) in DMF (5 ml) at room temperature, and the mixture thus obtained was then stirred at the same temperature as above for 1 hour and 30 minutes. Thereafter, methanesulfonamide (58.4 mg, 0.61 mmol) and 1,8-diazabicyclo[5.4.0]undec-7-ene (0.092 ml, 0.61 mmol) were added to the resulting solution at room temperature, and the mixture thus obtained was then stirred at the same temperature as above for 2 hours. Thereafter, an aqueous solution of citric acid (454 mg, 2.36 mmol) was added to the reaction solution, and the mixed solution was then extracted with ethyl acetate. The organic layer thus obtained was washed with water, and was then dried over anhydrous sodium sulfate. The solvent was distilled away under reduced pressure, and the residue thus obtained was then purified by silica gel column chromatography (methanol:dichloromethane=0:1 to 1:9, v/v). The solid thus obtained was washed with diethyl ether, followed by collection by filtration and drying, to obtain the title compound (230 mg, yield: 80%).

$^1$H-NMR Spectrum (400 MHz, CDCl$_3$) δ ppm:

7.96 (1H, s), 7.49 (1H, s), 7.17 (1H, d, J=8.6 Hz), 6.72 (1H, d, J=8.6 Hz), 5.06 (1H, s), 3.74 (3H, s), 3.39 (3H, s), 2.85 (3H, s), 2.51-2.36 (4H, m), 2.48 (3H, s), 2.25-2.14 (4H, m), 1.11 (6H, s), 0.97 (6H, s);

MS (ESI) m/z: 607 [M+H]$^+$.

Example 41

6-[4-Methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide 2-methylpropan-2-amine salt 2-Methylpropan-2-amine (0.048 ml, 0.45 mmol) was added to a suspension of the 6-[4-methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide produced in Example 16 (136 mg, 0.22 mmol) in ethanol (1.4 ml) at room temperature, and the mixture thus obtained was then stirred at the same temperature as above for 15 minutes. Thereafter, diethyl ether was added to the reaction solution, and the solid thus generated was collected by filtration and was then dried to obtain the title compound (130 mg, yield: 85%).

$^1$H-NMR Spectrum (400 MHz, CDCl$_3$) δ ppm: 7.63 (1H, d, J=7.8 Hz), 7.35 (1H, d, J=7.8 Hz), 7.12-7.10 (1H, m), 6.68 (1H, d, J=8.6 Hz), 5.00 (1H, s), 3.72 (3H, s), 3.34 (3H, s), 2.76 (3H, s), 2.68 (3H, s), 2.54-2.36 (4H, m), 2.29-2.10 (4H, m), 1.12 (6H, s), 0.96 (6H, s), 0.95 (9H, s);

MS (ESI) m/z: 607 [M+H]$^+$;

Anal. Calcd for C$_{37}$H$_{49}$N$_3$O$_7$S: C, 65.36; H, 7.26; N, 6.18; S, 4.72. Found: C, 65.17; H, 7.28; N, 6.09; S, 4.62.

Example 42

6-[4-Methoxy-2-methyl-3-(3,3,6,6-tetramethyl-1,8-dioxo-2,3,4,5,6,7,8,9-octahydro-1H-xanthen-9-yl)phenyl]-4-methyl-N-(methylsulfonyl)pyridine-2-carboxamide 2-methylpropan-2-amine salt 2-Methylpropan-2-amine (0.041 ml, 0.39 mmol) was added to a suspension of the 6-[4-methoxy-2-methyl-3-(3,3,6,6-tetramethyl-1,8-dioxo-2,3,4,5,6,7,8,9-octahydro-1H-xanthen-9-yl)phenyl]-4-methyl-N-(methylsulfonyl)pyridine-2-carboxamide produced in Example 40 (118 mg, 0.19 mmol) in ethanol (1.2 ml) at room temperature, and the mixture thus obtained was then stirred at the same temperature as above for 1 hour. Thereafter, diethyl ether was added to the reaction solution, and the solid thus generated was collected by filtration and was then dried to obtain the title compound (111 mg, yield: 84%).

$^1$H-NMR Spectrum (400 MHz, CDCl$_3$) δ ppm:
8.11-8.10 (1H, m), 7.28 (1H, m), 7.14 (1H, d, J=8.2 Hz), 6.68 (1H, d, J=8.2 Hz), 4.98 (1H, s), 3.72 (3H, s), 3.27 (3H, s), 2.70 (3H, s), 2.55-2.36 (4H, m), 2.44 (3H, s), 2.30-2.09 (4H, m), 1.13 (6H, s), 0.96 (6H, s), 0.92 (9H, s);
MS (ESI) m/z: 607 [M+H]$^+$;
Anal. Calcd for C$_{37}$H$_{49}$N$_3$O$_7$S: C, 65.36; H, 7.26; N, 6.18; S, 4.72. Found: C, 63.61; H, 7.35; N, 5.97; S, 4.60.

Example 43

6-[4-Methoxy-2-methyl-3-(3,3,6,6-tetramethyl-1,8-dioxo-2,3,4,5,6,7,8,9-octahydro-1H-xanthen-9-yl)phenyl]-3,4-dimethylpyridine-2-carboxylic acid $^1$H-NMR Spectrum (400 MHz, CDCl$_3$) δ ppm: 7.47 (1H, s), 7.15 (1H, d, J=8.6 Hz), 6.70 (1H, d, J=8.6 Hz), 5.06 (1H, s), 3.73 (3H, s), 2.87 (3H, s), 2.78 (3H, s), 2.51-2.35 (4H, m), 2.43 (3H, s), 2.25-2.13 (4H, m), 1.11 (6H, s), 0.97 (6H, s);
MS (ESI) m/z: 544 [M+H]$^+$.

Example 44

6-[4-Methoxy-2-methyl-3-(3,3,6,6-tetramethyl-1,8-dioxo-2,3,4,5,6,7,8,9-octahydro-1H-xanthen-9-yl)phenyl]-3,4-dimethyl-N-(methylsulfonyl)pyridine-2-carboxamide $^1$H-NMR Spectrum (400 MHz, CDCl$_3$) δ ppm: 7.46 (1H, s), 7.15 (1H, d, J=8.6 Hz), 6.72-6.70 (1H, m), 5.06 (1H, s), 3.74 (3H, s), 3.38 (3H, s), 2.85 (3H, s), 2.72 (3H, s), 2.51-2.35 (4H, m), 2.41 (3H, s), 2.25-2.14 (4H, m), 1.11 (6H, s), 0.98 (6H, s);
MS (ESI) m/z: 621 [M+H]$^+$.

Example 45

3-Ethyl-6-[4-methoxy-3-(3,3,6,6-tetramethyl-1,8-dioxo-2,3,4,5,6,7,8,9-octahydro-1H-xanthen-9-yl)phenyl]pyridine-2-carboxylic acid $^1$H-NMR Spectrum (400 MHz, CDCl$_3$) δ ppm: 7.98 (1H, d, J=2.3 Hz), 7.94 (1H, d, J=7.8 Hz), 7.79-7.75 (2H, m), 6.90 (1H, d, J=8.6 Hz), 4.95 (1H, s), 3.85 (3H, s), 3.27-3.22 (2H, m), 2.52-2.38 (4H, m), 2.26-2.12 (4H, m), 1.32-1.28 (3H, m), 1.11 (6H, s), 0.96 (6H, s);
MS (ESI) m/z: 530 [M+H]$^+$.

Example 46

3-Ethyl-6-[4-methoxy-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide $^1$H-NMR Spectrum (400 MHz, CDCl$_3$) δ ppm: 7.96-7.93 (2H, m), 7.80 (1H, dd, J=8.6, 2.3 Hz), 7.73 (1H, d, J=8.2 Hz), 6.90 (1H, d, J=8.6 Hz), 4.94 (1H, s), 3.85 (3H, s), 3.41 (3H, s), 3.22-3.16 (2H, m), 2.51-2.41 (4H, m), 2.25-2.12 (4H, m), 1.31-1.28 (3H, m), 1.10 (6H, s), 0.96 (6H, s);
MS (ESI) m/z: 607 [M+H]$^+$.

Example 47

3-[4-Methoxy-2-methyl-3-(3,3,6,6-tetramethyl-1,8-dioxo-2,3,4,5,6,7,8,9-octahydro-1H-xanthen-9-yl)phenyl]-5,6,7,8-tetrahydroisoquinoline-1-carboxylic acid $^1$H-NMR Spectrum (400 MHz, CDCl$_3$) δ ppm: 7.38 (1H, s), 7.16-7.14 (1H, m), 6.70 (1H, d, J=8.6 Hz), 5.07 (1H, s), 3.73 (3H, s), 3.39-3.36 (2H, m), 2.89-2.86 (2H, m), 2.87 (3H, s), 2.51-2.35 (4H, m), 2.25-2.13 (4H, m), 1.92-1.81 (4H, m), 1.11 (6H, s), 0.97 (6H, s);
MS (ESI) m/z: 570 [M+H]$^+$.

Example 48

3-Amino-6-[4-methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid $^1$H-NMR Spectrum (400 MHz, CDCl$_3$) δ ppm:
7.44 (1H, d, J=8.6 Hz), 7.15-7.12 (2H, m), 6.68 (1H, d, J=8.6 Hz), 5.84 (2H, s), 5.05 (1H, s), 3.72 (3H, s), 2.86 (3H, s), 2.50-2.35 (4H, m), 2.25-2.13 (4H, m), 1.10 (6H, s), 0.96 (6H, s);
MS (ESI) m/z: 531 [M+H]$^+$.

Example 49

3-Amino-6-[4-methoxy-2-methyl-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide $^1$H-NMR Spectrum (400 MHz, CDCl$_3$) δ ppm: 7.41 (1H, d, J=8.6 Hz), 7.15-7.07 (2H, m), 6.69 (1H, d, J=8.6 Hz), 5.93 (2H, s), 5.04 (1H, s), 3.72 (3H, s), 3.37 (3H, s), 2.83 (3H, s), 2.50-2.35 (4H, m), 2.25-2.13 (4H, m), 1.10 (6H, s), 0.97 (6H, s);
MS (ESI) m/z: 608 [M+H]$^+$.

Example 50

5-Chloro-6-[4-methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide $^1$H-NMR Spectrum (400 MHz, CDCl$_3$) δ ppm: 7.76-7.75 (1H, m), 6.98 (1H, d, J=8.6 Hz), 6.72 (1H, d, J=8.6 Hz), 5.03 (1H, s), 3.75 (3H, s), 3.39 (3H, s), 2.77 (3H, s), 2.68 (3H, s), 2.51-2.36 (4H, m), 2.24-2.15 (4H, m), 1.11 (6H, s), 1.00 (6H, s);
MS (ESI) m/z: 641 [M+H]$^+$.

Example 51

3-Amino-6-[4-methoxy-3-(3,3,6,6-tetramethyl-1,8-dioxo-2,3,4,5,6,7,8,9-octahydro-1H-xanthen-9-yl)phenyl]pyridine-2-carboxylic acid $^1$H-NMR Spectrum (400 MHz, CDCl$_3$) δ ppm: 7.89 (1H, d, J=2.3 Hz), 7.79 (1H, d, J=9.0 Hz), 7.69-7.66 (1H, m), 7.16 (1H, d, J=9.0 Hz), 6.87-6.85 (1H, m), 5.80 (2H, s), 4.92 (1H, s), 3.82 (3H, s), 2.51-2.37 (4H, m), 2.25-2.12 (4H, m), 1.10 (6H, s), 0.96 (6H, s);
MS (ESI) m/z: 517 [M+H]$^+$.

Example 52

3-Amino-6-[4-methoxy-3-(3,3,6,6-tetramethyl-1,8-dioxo-2,3,4,5,6,7,8,9-octahydro-1H-xanthen-9-yl)phenyl]-N-(methylsulfonyl)pyridine-2-carboxamide $^1$H-NMR Spectrum (400 MHz, CDCl$_3$) δ ppm: 7.85-7.80 (2H, m), 7.72-7.69 (1H, m), 7.13 (1H, d, J=8.6 Hz), 6.87 (1H, d, J=8.6 Hz), 5.91 (2H, s), 4.92 (1H, s), 3.83 (3H, s), 3.40 (3H, s), 2.51-2.40 (4H, m), 2.25-2.12 (4H, m), 1.10 (6H, s), 0.96 (6H, s);
MS (ESI) m/z: 594 [M+H]$^+$.

Example 53

6-[4-Methoxy-2-methyl-3-(3,3,6,6-tetramethyl-1,8-dioxo-2,3,4,5,6,7,8,9-octahydro-1H-xanthen-9-yl)phenyl]-3-(methylamino)pyridine-2-carboxylic acid $^1$H-NMR Spectrum (400 MHz, CDCl$_3$) δ ppm: 7.73-7.69 (1H, m), 7.52 (1H, d, J=8.6 Hz), 7.17-7.13 (2H, m), 6.68 (1H, d, J=8.6 Hz), 5.06 (1H, s), 3.72 (3H, s), 2.99-2.98 (3H, m), 2.87 (3H, s), 2.50-2.35 (4H, m), 2.25-2.13 (4H, m), 1.11 (6H, s), 0.97 (6H, s);
MS (ESI) m/z: 545 [M+H]$^+$.

Example 54

6-[4-Methoxy-2-methyl-3-(3,3,6,6-tetramethyl-1,8-dioxo-2,3,4,5,6,7,8,9-octahydro-1H-xanthen-9-yl)phenyl]-3-(methylamino)-N-(methylsulfonyl)pyridine-2-carboxamide $^1$H-NMR Spectrum (400 MHz, CDCl$_3$) δ ppm: 7.88-7.84 (1H, m), 7.52 (1H, d, J=8.6 Hz), 7.17-7.11 (2H, m), 6.69 (1H, d, J=8.6 Hz), 5.05 (1H, s), 3.73 (3H, s), 3.36 (3H, s), 2.98-2.97 (3H, m), 2.85 (3H, s), 2.50-2.35 (4H, m), 2.24-2.13 (4H, m), 1.10 (6H, s), 0.97 (6H, s);
MS (ESI) m/z: 622 [M+H]$^+$.

Example 55

6-[4-Methoxy-3-(3,3,6,6-tetramethyl-1,8-dioxo-2,3,4,5,6,7,8,9-octahydro-1H-xanthen-9-yl)phenyl]pyridine-2-carboxamide $^1$H-NMR Spectrum (400 MHz, DMSO-D$_6$) δ ppm: 8.09-7.91 (4H, m), 7.79-7.78 (1H, m), 7.40 (2H, s), 6.99 (1H, d, J=8.6 Hz), 4.71 (1H, s), 3.80 (3H, s), 2.62-2.39 (4H, m), 2.28-1.99 (4H, m), 1.04 (6H, s), 0.86 (6H, s);
MS (ESI) m/z: 501 [M+H]$^+$.

Example 56

9-{2-Methoxy-5-[6-(1H-1,2,4-triazol-1-yl)pyridin-2-yl]phenyl}-3,3,6,6-tetramethyl-3,4,5,6,7,9-hexahydro-1H-xanthene-1,8(2H)-dione $^1$H-NMR Spectrum (400 MHz, CDCl$_3$) δ ppm: 9.31 (1H, s), 8.13 (1H, s), 8.12 (1H, d, J=2.4 Hz), 7.94-7.89 (2H, m), 7.79 (1H, dd, J=7.8, 0.8 Hz), 7.76 (1H, dd, J=7.8, 0.8 Hz), 6.92 (1H, d, J=9.0 Hz), 4.99 (1H, s), 3.87 (3H, s), 2.52 (2H, d, J=18 Hz), 2.42 (2H, d, J=18 Hz), 2.26 (2H, d, J=17 Hz), 2.17 (2H, d, J=17 Hz), 1.13 (6H, s), 0.99 (6H, s);
MS (ESI) m/z: 525 [M+H]$^+$.

Example 57

6-[4-Methoxy-2-methyl-5-(3,3,6,6-tetramethyl-1,8-dioxo-2,3,4,5,6,7,8,9-octahydro-1H-xanthen-9-yl)phenyl]pyridine-2-carboxylic acid $^1$H-NMR Spectrum (400 MHz, CDCl$_3$) δ ppm: 8.13 (1H, d, J=7.8 Hz), 7.98 (1H, dd, J=7.8, 7.6 Hz), 7.77 (1H, d, J=7.6 Hz), 7.53 (1H, s), 6.69 (1H, s), 4.85 (1H, s), 3.82 (3H, s), 2.48 (2H, d, J=17 Hz), 2.37 (2H, d, J=17 Hz), 2.23 (2H, d, J=16 Hz), 2.14 (2H, d, J=16 Hz), 1.10 (6H, s), 0.98 (6H, s);
MS (ESI) m/z: 514 [M−H]$^−$.

Example 58

9-[5-(6-Aminopyridin-2-yl)-2-methoxyphenyl]-3,3,6,6-tetramethyl-3,4,5,6,7,9-hexahydro-1H-xanthene-1,8(2H)-dione $^1$H-NMR Spectrum (400 MHz, CDCl$_3$) δ ppm: 7.91 (1H, d, J=2.3 Hz), 7.74 (1H, dd, J=8.6, 2.3 Hz), 7.44 (1H, d, J=7.8 Hz), 7.07 (1H, d, J=7.8 Hz), 6.82 (1H, d, J=8.6 Hz), 6.38 (1H, d, J=7.8 Hz), 4.95 (1H, s), 4.43 (2H, s), 3.81 (3H, s), 2.47 (2H, d, J=18 Hz), 2.35 (2H, d, J=18 Hz), 2.21 (2H, d, J=16 Hz), 2.13 (2H, d, J=16 Hz), 1.09 (6H, s), 0.96 (6H, s);
MS (ESI) m/z: 473 [M+H]$^+$.

Example 59

N-{6-[4-Methoxy-3-(3,3,6,6-tetramethyl-1,8-dioxo-2,3,4,5,6,7,8,9-octahydro-1H-xanthen-9-yl)phenyl]pyridin-2-yl}methanesulfonamide $^1$H-NMR Spectrum (500 MHz, CDCl$_3$) δ ppm: 8.01 (1H, s), 7.90-7.71 (3H, m), 7.16 (1H, d, J=8.3 Hz), 6.86 (1H, d, J=8.3 Hz), 4.96 (1H, s), 3.85 (3H, s), 3.62 (3H, s), 2.48 (2H, d, J=17 Hz), 2.38 (2H, d, J=17 Hz), 2.22 (2H, d, J=16 Hz), 2.14 (2H, d, J=16 Hz), 1.10 (3H, s), 0.96 (3H, s);
MS (ESI) m/z: 551 [M+H]$^+$.

Example 60

1-(2-Hydroxyethyl)-3-{6-[4-methoxy-3-(3,3,6,6-tetramethyl-1,8-dioxo-2,3,4,5,6,7,8,9-octahydro-1H-xanthen-9-yl)phenyl]pyridin-2-yl}urea $^1$H-NMR Spectrum (500 MHz, CDCl$_3$) δ ppm: 8.34 (1H, s), 8.15 (1H, s), 7.55-7.50 (2H, m), 7.16 (1H, d, J=7.3 Hz), 6.80 (1H, d, J=8.3 Hz), 6.60 (1H, d, J=8.3 Hz), 4.86 (1H, s), 4.30-4.18 (1H, m), 3.88-3.80 (2H, m), 3.75 (4H, m), 2.48 (2H, d, J=18 Hz), 2.38 (2H, d, J=18 Hz), 2.27-2.10 (4H, m), 1.10 (6H, s), 0.95 (6H, s);

MS (ESI) m/z: 560 [M+H]$^+$.

Example 61

N-{6-[4-Methoxy-3-(3,3,6,6-tetramethyl-1,8-dioxo-2,3,4,5,6,7,8,9-octahydro-1H-xanthen-9-yl)phenyl]pyridin-2-yl}acetamide $^1$H-NMR Spectrum (400 MHz, CDCl$_3$) δ ppm: 8.08 (1H, d, J=2.0 Hz), 8.10-7.95 (2H, m), 7.72 (1H, dd, J=8.6, 2.0 Hz), 7.68 (1H, d, J=8.2 Hz), 7.44 (1H, d, J=7.6 Hz), 6.82 (1H, d, J=8.6 Hz), 4.92 (1H, s), 3.79 (3H, s), 2.48 (2H, d, J=18 Hz), 2.38 (2H, d, J=18 Hz), 2.23 (3H, s), 2.22 (2H, d, J=16 Hz), 2.14 (2H, d, J=16 Hz), 1.10 (6H, s), 0.95 (6H, s);

MS (ESI) m/z: 515 [M+H]$^+$.

Example 62

1-{6-[4-Methoxy-3-(3,3,6,6-tetramethyl-1,8-dioxo-2,3,4,5,6,7,8,9-octahydro-1H-xanthen-9-yl)phenyl]pyridin-2-yl}-1H-1,2,4-triazole-3-carboxamide $^1$H-NMR Spectrum (400 MHz, CDCl$_3$) δ ppm:
9.33 (1H, s), 8.12 (1H, d, J=1.8 Hz), 7.93-7.86 (3H, m), 7.80 (1H, dd, J=7.4, 1.8 Hz), 7.15 (1H, bs), 6.90 (1H, d, J=8.6 Hz), 5.88 (1H, bs), 4.96 (1H, s), 3.84 (3H, s), 2.50 (2H, d, J=18 Hz), 2.40 (2H, d, J=18 Hz), 2.24 (2H, d, J=16 Hz), 2.14 (2H, d, J=16 Hz), 1.11 (6H, s), 0.97 (6H, s);

MS (ESI) m/z: 568 [M+H]$^+$.

Example 63

9-[3-(6-Aminopyridin-2-yl)-6-methoxy-2-methylphenyl]-3,3,6,6-tetramethyl-3,4,5,6,7,9-hexahydro-1H-xanthene-1,8(2H)-dione $^1$H-NMR Spectrum (500 MHz, CDCl$_3$) δ ppm: 7.48 (1H, dd, J=8.1, 7.5 Hz), 7.17 (1H, d, J=8.4 Hz), 6.78 (1H, d, J=7.5 Hz), 6.68 (1H, d, J=8.4 Hz), 6.46 (1H, d, J=8.1 Hz), 5.33 (1H, s), 5.11 (1H, s), 4.58 (1H, bs), 3.72 (3H, s), 2.88 (3H, s), 2.49 (2H, d, J=17 Hz), 2.39 (2H, d, J=17 Hz), 2.24 (2H, d, J=17 Hz), 2.16 (2H, d, J=17 Hz), 1.12 (6H, s), 0.98 (6H, s);

MS (ESI) m/z: 487 [M+H]$^+$.

Example 64

N-{6-[4-Methoxy-3-(3,3,6,6-tetramethyl-1,8-dioxo-2,3,4,5,6,7,8,9-octahydro-1H-xanthen-9-yl)phenyl]pyridin-2-yl}glycine $^1$H-NMR Spectrum (400 MHz, CDCl$_3$) δ ppm: 7.88-7.80 (2H, m), 7.69 (1H, d, J=9.4 Hz), 7.13 (1H, d, J=7.4 Hz), 6.92 (1H, d, J=8.6 Hz), 6.62 (1H, d, J=9.4 Hz), 4.82 (1H, s), 4.12 (2H, s), 3.79 (3H, s), 2.49 (2H, d, J=18 Hz), 2.40 (2H, d, J=18 Hz), 2.24 (2H, d, J=16 Hz), 2.17 (2H, d, J=16 Hz), 1.11 (6H, s), 0.97 (6H, s);

MS (ESI) m/z: 529 [M−H]$^-$.

Example 65

6-[4-Methoxy-3-(3,3,6,6-tetramethyl-1,8-dioxo-2,3,4,5,6,7,8,9-octahydro-1H-xanthen-9-yl)phenyl]pyridine-2-sulfonamide $^1$H-NMR Spectrum (400 MHz, CDCl$_3$) δ ppm:
8.06 (1H, d, J=2.3 Hz), 7.93-7.81 (4H, m), 6.86 (1H, d, J=8.6 Hz), 5.22 (2H, s), 4.89 (1H, s), 3.81 (3H, s), 2.49 (2H, d, J=18 Hz), 2.47 (2H, d, J=18 Hz), 2.23 (2H, d, J=17 Hz), 2.14 (2H, d, J=17 Hz), 1.11 (6H, s), 0.96 (6H, s);

MS (ESI) m/z: 537 [M+H]$^+$.

Example 66

1-{6-[4-Methoxy-3-(3,3,6,6-tetramethyl-1,8-dioxo-2,3,4,5,6,7,8,9-octahydro-1H-xanthen-9-yl)phenyl]pyridin-2-yl}piperidine-2-carboxylic acid $^1$H-NMR Spectrum (400 MHz, CDCl$_3$) δ ppm: 7.98 (1H, d, J=2.3 Hz), 7.64 (1H, dd, J=8.6, 2.3 Hz), 7.58 (1H, dd, J=8.2, 7.4 Hz), 7.18 (1H, d, J=7.4 Hz), 6.83 (1H, d, J=8.6 Hz), 6.72 (1H, d, J=8.2 Hz), 4.97 (1H, s), 4.81-4.77 (1H, m), 3.85 (3H, s), 3.72-3.65 (2H, m), 3.35-3.26 (m, 1H), 2.53-2.33 (7H, m), 2.25-2.10 (6H, m), 1.08 (6H, s), 0.96-0.87 (6H, m);

MS (ESI) m/z: 585 [M+H]$^+$.

Example 67

N-({6-[4-methoxy-3-(3,3,6,6-tetramethyl-1,8-dioxo-2,3,4,5,6,7,8,9-octahydro-1H-xanthen-9-yl)phenyl]pyridin-2-yl}sulfonyl)acetamide $^1$H-NMR Spectrum (400 MHz, CDCl$_3$) δ ppm: 8.11 (1H, d, J=2.4 Hz), 8.01-7.92 (3H, m), 7.81-7.77 (1H, m), 6.86 (1H, d, J=9.0 Hz), 4.87 (1H, s), 3.79 (3H, s), 2.49 (2H, d, J=18 Hz), 2.39 (2H, d, J=18 Hz), 2.27-2.18 (5H, m), 2.14 (2H, d, J=17 Hz), 1.10 (6H, s), 0.97 (6H, s);

MS (ESI) m/z: 577 [M−H]$^-$.

Example 68

1-{6-[4-Methoxy-2-methyl-3-(3,3,6,6-tetramethyl-1,8-dioxo-2,3,4,5,6,7,8,9-octahydro-1H-xanthen-9-yl)phenyl]pyridin-2-yl}pyrrolidine-3-carboxylic acid $^1$H-NMR Spectrum (400 MHz, CDCl$_3$) δ ppm: 7.47 (1H, t, J=7.8 Hz), 7.13 (1H, d, J=7.8 Hz), 6.63 (1H, d, J=8.2 Hz), 6.59 (1H, d, J=6.7 Hz), 6.36-6.27 (1H, m), 5.00 (1H, s), 3.78-3.53 (6H, m), 3.47-3.38 (1H, m), 3.20-3.08 (1H, m), 2.80 (3H, s), 2.44 (2H, d, J=18 Hz), 2.34 (2H, d, J=18 Hz), 2.28-1.80 (6H, m), 1.07 (6H, s), 0.93 (6H, s);

MS (ESI) m/z: 585 [M+H]$^+$.

Example 69

1-{6-[4-Methoxy-2-methyl-3-(3,3,6,6-tetramethyl-1,8-dioxo-2,3,4,5,6,7,8,9-octahydro-1H-xanthen-9-yl)phenyl]pyridin-2-yl}proline $^1$H-NMR Spectrum (500 MHz, CDCl$_3$) δ ppm: 7.59 (1H, dd, 8.3, 7.4 Hz), 7.19 (1H, d, J=8.5 Hz), 6.83 (1H, d, J=7.4 Hz), 6.68 (1H, d, J=8.3 Hz), 6.49 (1H, d, J=8.5 Hz), 5.05 (1H, s), 4.56 (1H, d, J=8.1 Hz), 3.71 (3H, s), 3.53-3.43 (1H, m), 3.33-3.27 (1H, m), 2.88 (3H, s), 2.75-2.68 (1H, m), 2.46 (2H, d, J=18 Hz), 2.37 (2H, d, J=18 Hz), 2.24-2.06 (6H, m), 1.96-1.88 (1H, m), 1.10 (6H, s), 0.97 (3H, s), 0.96 (3H, s);

MS (ESI) m/z: 585 [M+H]$^+$.

Example 70

9-[2-Methoxy-5-(pyridin-3-yl)phenyl]-3,3,6,6-tetramethyl-3,4,5,6,7,9-hexahydro-1H-xanthene-1,8(2H)-dione $^1$H-NMR Spectrum (400 MHz, CDCl$_3$) δ ppm: 8.80 (1H, d, J=2.0 Hz), 8.51 (1H, dd, J=1.5, 4.9 Hz), 7.87 (1H, td, 2.0, 7.8 Hz), 7.63 (1H, d J=2.4 Hz), 7.34 (1H, dd, 8.8, 2.4 Hz), 7.31 (1H, dd, J=7.8, 4.9 Hz), 6.87 (1H d, J=8.8 Hz), 4.94 (1H, s), 3.84 (3H, s), 2.48 (2H, ABq, J=17.6 Hz), 2.39 (2H, ABq, 17.6 Hz), 2.23 (2H, ABq, J=16.6 Hz), 2.15 (2H, ABq, 16.6 Hz), 1.10 (6H, s), 0.97 (6H, s);
MS (ESI) m/z: 458 [M+H]$^+$.

Example 71

9-[2-Methoxy-5-(pyridin-2-yl)phenyl]-3,3,6,6-tetramethyl-3,4,5,6,7,9-hexahydro-1H-xanthene-1,8(2H)-dione $^1$H-NMR Spectrum (400 MHz, CDCl$_3$) δ ppm: 8.61 (1H, brd), 7.98 (1H, d, J=2.4 Hz), 7.89 (1H, dd, J=2.4, 8.8 Hz), 7.76 (1H, d, J=7.8 Hz), 7.68 (1H, dt, J=1.8, 7.7 Hz), 7.12 (1H, ddd, 1.1, 4.8, 7.4), 6.86 (1H, d, J=8.8 Hz), 4.95 (1H, s), 3.82 (3H, s), 2.47 (2H, ABq, J=17.6 Hz), 2.40 (2H, ABq, J=17.6 Hz), 2.22 (2H, ABq, J=16.6 Hz) 2.14 (2H, ABq, 16.6 Hz), 1.10 (6H, s), 0.96 (6H, s);
MS (ESI) m/z: 458 [M+H]$^+$.

Example 72

9-[2-Methoxy-5-(pyridin-4-yl)phenyl]-3,3,6,6-tetramethyl-3,4,5,6,7,9-hexahydro-1H-xanthene-1,8(2H)-dione $^1$H-NMR Spectrum (400 MHz, CDCl$_3$) δ ppm: 8.58 (2H, d, J=5.9 Hz), 7.75 (1H, d, J=2.0 Hz), 7.9 (2H, d, J=5.9 Hz), 7.41 (1H, d, J=2.0, 8.3 Hz), 6.85 (1H, d, J=8.3 Hz), 4.92 (1H, s), 3.82 (3H, s), 2.48 (2H, ABq, J=17.6 Hz), 2.39 (2H, Abq, J=17.6 Hz), 2.23 (4H, Abq, J=16.6 Hz), 2.14 (2H, Abq, J=16.6 Hz), 1.10 (6H, s), 0.96 (6H, s);
MS (ESI) m/z: 458 [M+H]$^+$.

Example 73

6-[4-Methoxy-3-(3,3,6,6-tetramethyl-1,8-dioxo-2,3,4,5,6,7,8,9-octahydro-1H-xanthen-9-yl)phenyl]pyridine-3-carboxylic acid MS (ESI) m/z: 502 [M+H]$^+$

Example 74

5-[4-Methoxy-3-(3,3,6,6-tetramethyl-1,8-dioxo-2,3,4,5,6,7,8,9-octahydro-1H-xanthen-9-yl)phenyl]pyridine-2-carboxylic acid MS (ESI) m/z: 502 [M+H]$^+$

Example 75

4-[4-Methoxy-2-methyl-3-(3,3,6,6-tetramethyl-1,8-dioxo-2,3,4,5,6,7,8,9-octahydro-1H-xanthen-9-yl)phenyl]pyrimidine-2-carboxylic acid amide

[Formula 33]

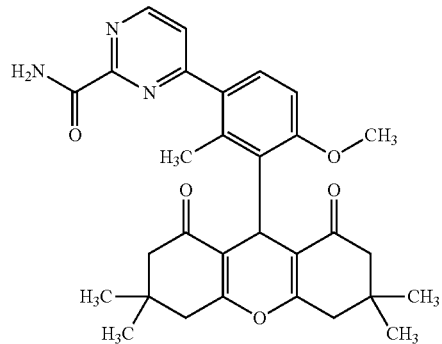

Example 75-1

3-(2-Chloropyrimidin-4-yl)-6-methoxy-2-methylbenzaldehyde

A 2 M aqueous solution of sodium carbonate (2.72 mL, 5.43 mol) and tetrakistriphenylphosphine palladium(0) (209 mg, 0.181 mmol) were added to a suspension of the 6-methoxy-2-methyl-3-(4,4,5,5-tetramethyl-1,3,2-dioxaborolan-2-yl)benzaldehyde obtained in Example 4-1 (500 mg, 1.81 mmol) and 2,4-dichloropyrimidine (405 mg, 2.72 mmol) in dimethoxyethane (5.4 mL) at room temperature. The mixture thus obtained was stirred at 80° C. for 10 hours. Thereafter, the resulting solution was cooled to room temperature. Water was added to the reaction solution, and the precipitated crude product was collected by filtration and was then washed with water and diisopropyl ether to obtain the title compound (418 mg, yield: 88%).
$^1$H-NMR Spectrum (500 MHz, CDCl$_3$) δ ppm:
10.67 (1H, s), 8.65 (1H, d, J=5.4 Hz), 7.67 (1H, d, J=8.8 Hz), 7.33 (1H, d, J=5.4 Hz), 6.99 (1H, d, J=8.8 Hz), 3.97 (3H, s), 2.58 (3H, s), 1.55 (3H, s).

Example 75-2

Methyl 4-(3-formyl-4-methoxy-2-methylphenyl)pyrimidine-2-carboxylate

Triethylamine (656 μL, 4.71 mol) and a [1,1'-bis(diphenylphosphino)ferrocene]palladium(II) dichloride dichloromethane adduct (256 mg, 0.314 mmol) were added to a solution of the 3-(2-chloropyrimidin-4-yl)-6-methoxy-2-methylbenzaldehyde obtained in Example 75-1 (412 mg, 1.57 mmol) in DMF (4.0 mL) and methanol (4.0 mL) at room temperature, and the mixture thus obtained was then stirred under a carbon monoxide atmosphere at 80° C. for 8 hours. Thereafter, the reaction solution was cooled to room temperature, and water was then added to the reaction solution. The mixed solution was extracted with ethyl acetate twice. The organic layer thus obtained was washed with water and brine, and was then dried over anhydrous sodium sulfate. Thereafter, the solvent was distilled away under reduced pressure. The residue thus obtained was purified by silica gel column chromatography (hexane:ethyl acetate=1:1 to 0:1, v/v) to obtain the title compound (150 mg, yield: 33%).
$^1$H-NMR Spectrum (500 MHz, CDCl$_3$) δ ppm:
10.68 (1H, s), 8.95 (1H, d, J=5.1 Hz), 7.68 (1H, d, J=8.6 Hz), 7.53 (1H, d, J=5.1 Hz), 6.99 (1H, d, J=8.6 Hz), 4.08 (3H, s), 3.97 (3H, s), 2.57 (3H, s).

Example 75-3

Methyl 4-[4-methoxy-2-methyl-3-(3,3,6,6-tetramethyl-1,8-dioxo-2,3,4,5,6,7,8,9-octahydro-1H-xanthen-9-yl)phenyl]pyrimidine-2-carboxylate Dimedone (127 mg, 0.907 mol) and pyrrolidine (34.4 µL, 0.0412 mmol) were added to a suspension of the methyl 4-(3-formyl-4-methoxy-2-methylphenyl)pyrimidine-2-carboxylate obtained in Example 75-2 (118 mg, 0.412 mmol) in ethanol (2.0 mL) at room temperature, and the mixture thus obtained was then stirred at 80° C. for 1.5 hours. Thereafter, the reaction solution was cooled to room temperature, and the solvent was then distilled away under reduced pressure. The residue thus obtained was dissolved in chloroform (2.0 mL), and p-toluenesulfonic acid monohydrate (23.5 mg, 0.124 mmol) was then added to the solution thus obtained at room temperature. The mixture thus obtained was stirred at 70° C. for 1 hour. Thereafter, the reaction solution was cooled to room temperature, and a saturated aqueous solution of sodium hydrogen carbonate was then added to the reaction solution. The mixed solution was extracted with dichloromethane twice, and the organic layer thus obtained was then dried over anhydrous sodium sulfate. After that, the solvent was distilled away under reduced pressure. The residue thus obtained was purified by silica gel column chromatography (hexane:ethyl acetate=1:1 to 0:1, v/v) to obtain the title compound (209 mg, yield: 95%).

$^1$H-NMR Spectrum (500 MHz, CDCl$_3$) δ ppm:
8.86 (1H, d, J=5.4 Hz), 7.60 (1H, d, J=5.4 Hz), 7.34 (1H, d, J=8.3 Hz), 6.74 (1H, d, J=8.3 Hz), 5.07 (1H, s), 4.06 (3H, s), 3.73 (3H, s), 2.93 (3H, s), 2.48 (2H, d, J=17.6 Hz), 2.36 (2H, d, J=17.6 Hz), 2.22 (2H, d, J=16.6 Hz), 2.13 (2H, d, J=16.6 Hz), 1.10 (6H, s), 0.95 (6H, s).

Example 75-4

4-[4-Methoxy-2-methyl-3-(3,3,6,6-tetramethyl-1,8-dioxo-2,3,4,5,6,7,8,9-octahydro-1H-xanthen-9-yl)phenyl]pyrimidine-2-carboxylic acid A 1 M aqueous solution of sodium hydroxide (466 µL, 0.466 mol) was added to a solution of the methyl 4-[4-methoxy-2-methyl-3-(3,3,6,6-tetramethyl-1,8-dioxo-2,3,4,5,6,7,8,9-octahydro-1H-xanthen-9-yl)phenyl]pyrimidine-2-carboxylate obtained in Example 75-3 (206 mg, 0.388 mmol) in THF (0.5 mL) and methanol (0.5 mL) at room temperature. The mixture thus obtained was stirred at the same temperature as above for 15 minutes. Thereafter, the solvent was distilled away under reduced pressure, and water was then added to the residue. The mixed solution was washed with diethyl ether, and 1 M-hydrochloric acid was then added to the water layer thus obtained, so that it was converted to an acidic aqueous solution. The resulting solution was extracted with ethyl acetate twice. The organic layer thus obtained was washed with brine, and was then dried over anhydrous sodium sulfate. The solvent was distilled away under reduced pressure, and the residue thus obtained was then solidified with dichloromethane and hexane to obtain the title compound (158 mg, yield: 79%).

$^1$H-NMR Spectrum (500 MHz, CDCl$_3$) δ ppm:
8.94 (1H, d, J=5.4 Hz), 7.68 (1H, d, J=5.4 Hz), 7.32 (1H, d, J=8.8 Hz), 6.77 (1H, d, J=8.8 Hz), 5.07 (1H, s), 3.76 (3H, s), 2.96 (3H, s), 2.49 (2H, d, J=17.6 Hz), 2.38 (2H, d, J=17.6 Hz), 2.24 (2H, d, J=16.6 Hz), 2.15 (2H, d, J=16.6 Hz), 1.11 (6H, s), 0.96 (6H, s).

Example 75-5

4-[4-Methoxy-2-methyl-3-(3,3,6,6-tetramethyl-1,8-dioxo-2,3,4,5,6,7,8,9-octahydro-1H-xanthen-9-yl)phenyl]pyrimidine-2-carboxylic acid amide 1,1'-Carbonyldiimidazole (50.1 mg, 0.309 mol) was added to a solution of the 4-[4-methoxy-2-methyl-3-(3,3,6,6-tetramethyl-1,8-dioxo-2,3,4,5,6,7,8,9-octahydro-1H-xanthen-9-yl)phenyl]pyrimidine-2-carboxylic acid obtained in Example 75-4 (133 mg, 0.257 mmol) in THF (2.0 mL) and DMF (0.5 mL) at room temperature, and the mixture thus obtained was then stirred at the same temperature as above for 30 minutes. Thereafter, 27% ammonia water was added to the resulting solution, and the mixture thus obtained was further stirred at the same temperature as above for 30 minutes. Thereafter, water was added to the reaction solution, and the mixed solution was then extracted with ethyl acetate twice. The organic layer thus obtained was washed with 1 M-hydrochloric acid and brine, and was then dried over anhydrous sodium sulfate. After that, the solvent was distilled away under reduced pressure. The residue thus obtained was solidified with diethyl ether to obtain the title compound (114 mg, yield: 86%).

$^1$H-NMR Spectrum (500 MHz, CDCl$_3$) δ ppm:
8.89 (1H, d, J=5.1 Hz), 7.94 (1H, s), 7.56 (1H, d, J=5.1 Hz), 7.23 (1H, d, J=8.6 Hz), 6.74 (1H, d, J=8.6 Hz), 5.84 (1H, s), 5.08 (1H, s), 3.75 (3H, s), 2.94 (3H, s), 2.49 (2H, d, J=17.6 Hz), 2.37 (2H, d, J=17.6 Hz), 2.23 (2H, d, J=16.4 Hz), 2.15 (2H, d, J=16.4 Hz), 1.11 (6H, s), 0.96 (6H, s);
MS (ESI) m/z: 516 [M+H]$^+$.

Example 76

9-{3-[2-(Hydroxymethyl)pyrimidin-4-yl]-6-methoxy-2-methylphenyl}-3,3,6,6-tetramethyl-3,4,5,6,7,9-hexahydro-1H-xanthene-1,8(2H)-dione

[Formula 34]

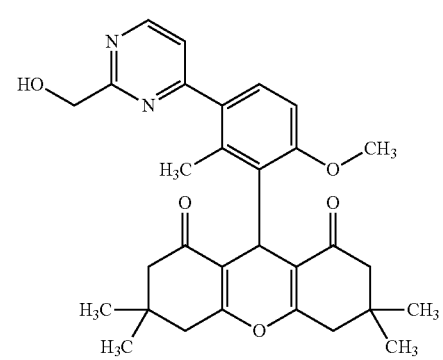

1,1'-Carbonyldiimidazole (33.9 mg, 0.209 mol) was added to a suspension of the 4-[4-methoxy-2-methyl-3-(3,3,6,6-tetramethyl-1,8-dioxo-2,3,4,5,6,7,8,9-octahydro-1H-xanthen-9-yl)phenyl]pyrimidine-2-carboxylic acid obtained in Example 75-4 (90.0 mg, 0.174 mmol) in THF (2.0 mL) at room temperature, and the mixture thus obtained was then stirred at 50° C. for 1.5 hours. Thereafter, DMF (0.5 mL) was added to the resulting solution, and the mixture thus obtained was further stirred at the same temperature as above for 20 minutes. Subsequently, the reaction solution was cooled to 0° C., and sodium borohydride (13.2 mg, 0.348 mmol) and water (0.1 mL) were then added to the reaction solution. The mixture thus obtained was stirred at room temperature for 30 minutes. Thereafter, water and 1 M-hydrochloric acid were added to the reaction solution, and the mixed solution was then extracted with ethyl acetate twice. The organic layer thus obtained was washed with brine, and was then dried over anhydrous sodium sulfate. After that, the solvent was distilled away under reduced pressure. The residue thus obtained was purified by silica gel column chromatography (dichloromethane:methanol=1:0 to 10:1, v/v), and was then solidified with diethyl ether to obtain the title compound (49.9 mg, yield: 56%).

$^1$H-NMR Spectrum (500 MHz, CDCl$_3$) δ ppm:
8.68 (1H, d, J=5.4 Hz), 7.35 (1H, d, J=5.4 Hz), 7.28 (1H, d, J=8.8 Hz), 6.73 (1H, d, J=8.8 Hz), 5.08 (1H, s), 4.88 (2H, d, J=4.9 Hz), 3.90 (1H, t, J=4.9 Hz), 3.73 (3H, s), 2.94 (3H, s), 2.48 (2H, d, J=17.6 Hz), 2.37 (2H, d, J=17.6 Hz), 2.22 (2H, d, J=16.6 Hz), 2.14 (2H, d, J=16.6 Hz), 1.11 (6H, s), 0.95 (6H, s);
MS (ESI) m/z: 503 [M+H]$^+$.

Example 77

N-(2-hydroxyethyl)-4-[4-methoxy-2-methyl-3-(3,3,6,6-tetramethyl-1,8-dioxo-2,3,4,5,6,7,8,9-octahydro-1H-xanthen-9-yl)phenyl]pyrimidine-2-carboxylic acid amide $^1$H-NMR Spectrum (500 MHz, CDCl$_3$) δ ppm: 8.90 (1H, d, J=5.5 Hz), 8.61 (1H, s), 7.54 (1H, d, J=5.5 Hz), 7.25 (1H, d, J=8.6 Hz), 6.73 (1H, d, J=8.6 Hz), 5.08 (1H, s), 3.87 (2H, t, J=5.1 Hz), 3.74 (3H, s), 3.68 (2H, dt, J=5.5, 5.1 Hz), 3.12 (1H, t, J=5.5 Hz), 2.92 (3H, s), 2.49 (2H, d, J=17.6 Hz), 2.37 (2H, d, J=17.6 Hz), 2.24 (2H, d, J=16.4 Hz), 2.15 (2H, d, J=16.4 Hz), 1.11 (6H, s), 0.96 (6H, s);
MS (ESI) m/z: 560 [M+H]$^+$.

Example 78

9-[2-Methoxy-5-(pyrimidin-2-yl)phenyl]-3,3,6,6-tetramethyl-3,4,5,6,7,9-hexahydro-1H-xanthene-1,8(2H)-dione MS (ESI) m/z: 459 [M+H]$^+$.

Test Example

Oral Glucose Tolerance Test (1) Used Animals
Commercially available mice (C57BL/6J mice; male; 8 to 12 weeks old when used; distributed by Charles River Laboratories Japan, Inc.) were used.

(2) Experimental Methods/Results
After acclimatization with freely feeding (FR-2, Funabashi Farm Co., Ltd.) for one week or more, the mice were fasted overnight and then used for the test. A 0.5% methylcellulose (Wako Pure Chemical Industries, Ltd.) solution (0.5% MC) containing a test compound at a concentration of 1 mg/ml and a mixed solution (PG:Tween) of propylene glycol (80 v/v %, Nacalai Tesque, Inc.) and Tween 80 (20 v/v %, Nacalai Tesque, Inc.) containing a test compound at a concentration of 2 mg/ml were prepared for administration to the mice. The prepared solution was administered by oral gavage to four or five mice in each group at a dose of 10 mg/kg as the test compound. For a control group, a 0.5% methylcellulose solution (dose: 10 ml/kg) or a mixed solution of propylene glycol and Tween 80 (dose: 5 ml/kg) was orally administered to mice. An oral glucose tolerance test was carried out by administering a glucose solution (Otsuka Glucose Solution 50%; Otsuka Pharmaceutical Factory, Inc.) orally at a dose of 3 g/kg to the mice 30 minutes after administration of the test compound.

Blood was collected from the tail vein of each mouse immediately before administration of the test compound (T0), 25 minutes after administration of the test compound (T1), and 30 minutes (T2) and 90 minutes (T3) after oral glucose loading. The blood glucose level was measured using a blood glucose level measuring apparatus (ACCU-CHEK Aviva; Roche Diagnostics, K.K.). The blood glucose level T1 was analyzed as a value obtained 30 minutes after administration of the compound and immediately before glucose loading. According to the following formula, the area under the curve of blood glucose level was calculated, and thereafter, the blood glucose lowering rate (%) was calculated as a value relative to the control group. The results are shown in Table 1.

The area under the curve of blood glucose level=
[(blood glucose level T0+blood glucose level T1)×30]÷2+[(blood glucose level T1+blood glucose level T2)×30]÷2+[(blood glucose level T2+blood glucose level T3)×60]÷2

Blood glucose lowering rate(%)=[1−(the area under the curve of blood glucose level for the test compound group/the area under the curve of blood glucose level for the control group)]×100

TABLE 1

| Example No. | Solvent | Dose (mg/kg) | Blood glucose lowering rate (%) |
|---|---|---|---|
| 1 | PG:Tween | 10 | 39 |
| 4 | PG:Tween | 10 | 60 |
| 5 | PG:Tween | 10 | 43 |
| 8 | PG:Tween | 10 | 38 |
| 9 | PG:Tween | 10 | 42 |
| 10 | PG:Tween | 10 | 55 |
| 11 | PG:Tween | 10 | 42 |
| 23 | PG:Tween | 10 | 46 |
| 28 | PG:Tween | 10 | 60 |
| 75 | PG:Tween | 10 | 35 |
| 12 | 0.5% MC | 10 | 31 |
| 13 | 0.5% MC | 10 | 61 |
| 14 | 0.5% MC | 10 | 46 |
| 16 | 0.5% MC | 10 | 45 |
| 17 | 0.5% MC | 10 | 43 |
| 18 | 0.5% MC | 10 | 31 |
| 19 | 0.5% MC | 10 | 40 |
| 20 | 0.5% MC | 10 | 41 |
| 21 | 0.5% MC | 10 | 54 |
| 29 | 0.5% MC | 10 | 32 |
| 30 | 0.5% MC | 10 | 55 |
| 31 | 0.5% MC | 10 | 42 |
| 32 | 0.5% MC | 10 | 59 |
| 34 | 0.5% MC | 10 | 58 |
| 35 | 0.5% MC | 10 | 52 |
| 40 | 0.5% MC | 10 | 38 |
| 41 | 0.5% MC | 10 | 44 |
| 42 | 0.5% MC | 10 | 44 |
| 43 | 0.5% MC | 10 | 60 |
| 44 | 0.5% MC | 10 | 44 |
| 45 | 0.5% MC | 10 | 42 |
| 46 | 0.5% MC | 10 | 47 |
| 47 | 0.5% MC | 10 | 56 |
| 48 | 0.5% MC | 10 | 62 |
| 49 | 0.5% MC | 10 | 34 |
| 51 | 0.5% MC | 10 | 39 |
| 52 | 0.5% MC | 10 | 44 |
| 53 | 0.5% MC | 10 | 64 |

TABLE 1-continued

| Example No. | Solvent | Dose (mg/kg) | Blood glucose lowering rate (%) |
|---|---|---|---|
| 54 | 0.5% MC | 10 | 49 |
| 76 | 0.5% MC | 10 | 33 |

From the results of the tests described above, it is found that the compound of the present invention has an excellent glucose lowering effect, an effect to suppress postprandial glucose levels, an effect to improve impaired glucose tolerance, and the like. Accordingly, it is considered that the compound of the present invention is useful as a prophylactic agent and/or a therapeutic agent for hyperglycemia, diabetes, and pathologic conditions or diseases associated with these diseases.

Preparation Examples

Preparation Example 1

Capsule Preparation

| | |
|---|---|
| Compound of Example 4 or 13 | 50 mg |
| Lactose | 128 mg |
| Cornstarch | 70 mg |
| Magnesium stearate | 2 mg |
| | 250 mg |

The powder with the aforementioned formulation is mixed, and then sieved through a sieve with 60 meshes. The resulting powders are placed in a 250 mg gelatin capsule to prepare a capsule preparation.

Preparation Example 2

Tablet

| | |
|---|---|
| Compound of Example 21 or 10 | 50 mg |
| Lactose | 126 mg |
| Cornstarch | 23 mg |
| Magnesium stearate | 1 mg |
| | 200 mg |

The powder with the aforementioned formulation is mixed, and the mixed powder is granulated with cornstarch glue and then dried. The resultant is subjected to tableting using a tableting machine so as to prepare a tablet (200 mg/tablet). This tablet can be coated with sugar, as necessary.

[Industrial Applicability]

The novel phenylxanthene derivative represented by the above described general formula (I) of the present invention or a pharmacologically acceptable salt thereof has an excellent glucose lowering effect and is useful as a medicament.

The invention claimed is:
1. A compound of formula (I):

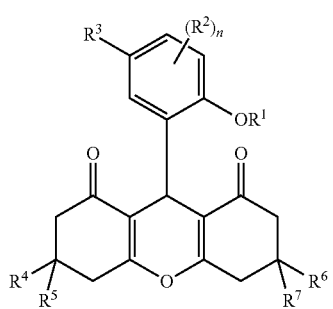

or a pharmacologically acceptable salt thereof, wherein
$R^1$ is a C1-C3 alkyl group,
each $R^2$ is independently a C1-C3 alkyl group,
$R^3$ is
  a pyridyl group optionally substituted with 1 to 4 substituents independently selected from substituent group α,
  a 5,6,7,8-tetrahydroisoquinolyl group optionally substituted with 1 to 4 substituents independently selected from substituent group α, or
  a pyrimidinyl group optionally substituted with 1 to 3 substituents independently selected from substituent group α,
$R^4$ and $R^5$ are each independently a C1-C3 alkyl group,
$R^6$ and $R^7$ are each independently a C1-C3 alkyl group,
n is an integer selected from 0 to 3, and
substituent group α is:
  a C1-C3 alkyl group,
  a C2-C3 alkynyl group,
  a C1-C3 alkoxy group optionally monosubstituted with a C6-C10 aryl group or a C1-C3 alkoxy group,
  a hydroxy C1-C3 alkyl group,
  a carbamoyl group optionally monosubstituted with a C1-C3 alkylsulfonyl group, which is optionally monosubstituted with a C1-C3 alkoxy group, or with a hydroxy C1-C3 alkyl group,
  a 3- to 10-membered heterocyclic group comprising 1 to 4 heteroatoms independently selected from nitrogen, oxygen, and sulfur, and which is optionally monosubstituted with a carbamoyl group or a carboxyl group,
  a 3- to 10-membered heterocyclic carbonyl group comprising 1 to 4 heteroatoms independently selected from nitrogen, oxygen, and sulfur,
  an amino group optionally monosubstituted with a C1-C3 alkylsulfonyl group, a C1-C3 alkylcarbonyl group, or a carboxy C1-C3 alkyl group,
  a ureido group optionally monosubstituted with a hydroxy C1-C3 alkyl group,
  an aminosulfonyl group optionally monosubstituted with a C1-C3 alkylcarbonyl group,
  a halogen atom,
  a carboxyl group,
  a hydroxyl group, and
  a cyano group.

2. The compound of claim 1 or a pharmacologically acceptable salt thereof, wherein $R^1$ is a methyl group.

3. The compound of claim 1, or a pharmacologically acceptable salt thereof, wherein $R^2$ is a methyl group.

4. The compound of claim 1 or a pharmacologically acceptable salt thereof, wherein $R^4$, $R^5$, $R^6$, and $R^7$ are each a methyl group.

5. A compound of formula (IA):

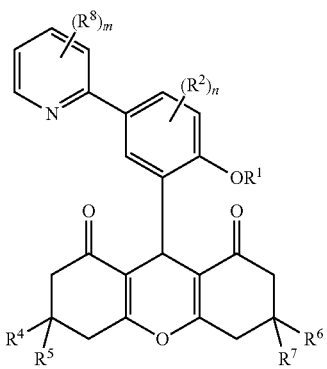

(IA)

or a pharmacologically acceptable salt thereof, wherein
$R^1$ is a C1-C3 alkyl group,
each $R^2$ is independently a C1-C3 alkyl group,
$R^4$ and $R^5$ are each independently a C1-C3 alkyl group,
$R^6$ and $R^7$ are each independently a C1-C3 alkyl group,
each $R^8$ is independently selected from substituent group α,
m is an integer selected from 0 to 4,
n is an integer selected from 0 to 3, and
substituent group α is:
 a C1-C3 alkyl group,
 a C2-C3 alkynyl group,
 a C1-C3 alkoxy group optionally monosubstituted with a C6-C10 aryl group or a C1-C3 alkoxy group,
 a hydroxy C1-C3 alkyl group,
 a carbamoyl group optionally monosubstituted with a C1-C3 alkylsulfonyl group, which is optionally monosubstituted with a C1-C3 alkoxy group, or with a hydroxy C1-C3 alkyl group,
 a 3- to 10-membered heterocyclic group comprising 1 to 4 heteroatoms independently selected from nitrogen, oxygen, and sulfur, wherein the 3- to 10-membered heterocyclic group may be monosubstituted with a carbamoyl group or a carboxyl group,
 a 3- to 10-membered heterocyclic carbonyl group comprising 1 to 4 heteroatoms independently selected from nitrogen, oxygen, and sulfur,
 an amino group optionally monosubstituted with a C1-C3 alkylsulfonyl group, a C1-C3 alkylcarbonyl group, or a carboxy C1-C3 alkyl group,
 a ureido group optionally monosubstituted with a hydroxy C1-C3 alkyl group,
 an aminosulfonyl group optionally monosubstituted with a C1-C3 alkylcarbonyl group,
 a halogen atom,
 a carboxyl group,
 a hydroxyl group, and
 a cyano group.

6. The compound of claim 5 or a pharmacologically acceptable salt thereof, wherein $R^1$, $R^2$, $R^4$, $R^5$, $R^6$, and $R^7$ are each a methyl group.

7. A compound of formula (II):

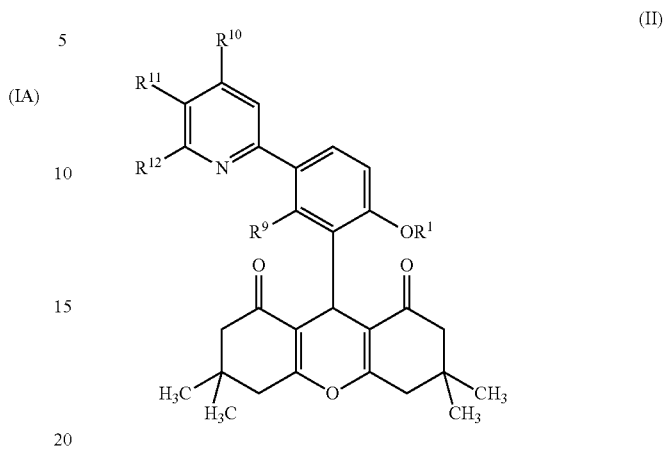

(II)

or a pharmacologically acceptable salt thereof, wherein
$R^9$ is a hydrogen atom or a C1-C3 alkyl group,
$R^{10}$ is a hydrogen atom or a C1-C3 alkyl group,
$R^{11}$ is a hydrogen atom, a C1-C3 alkyl group, or a C2-C3 alkynyl group, and
$R^{12}$ is
 a hydroxy C1-C3 alkyl group,
 a carbamoyl group optionally monosubstituted with a C1-C3 alkylsulfonyl group, which is optionally monosubstituted with a C1-C3 alkoxy group, or with a hydroxy C1-C3 alkyl group,
 a 3- to 10-membered heterocyclic group comprising 1 to 4 heteroatoms independently selected from nitrogen, oxygen, and sulfur, and which is optionally-monosubstituted with a carbamoyl group or a carboxyl group,
 a 3- to 10-membered heterocyclic carbonyl group comprising 1 to 4 heteroatoms independently selected from nitrogen, oxygen, and sulfur,
 a carboxyl group, or
 a cyano group.

8. The compound of claim 7 or a pharmacologically acceptable salt thereof, wherein $R^9$ is a methyl group.

9. The compound of claim 7, or a pharmacologically acceptable salt thereof, wherein $R^{10}$ is a hydrogen atom or a methyl group.

10. The compound of claim 7, or a pharmacologically acceptable salt thereof, wherein $R^{11}$ is a hydrogen atom or a methyl group.

11. The compound of claim 7, or a pharmacologically acceptable salt thereof, wherein $R^{12}$ is:
 a carbamoyl group optionally monosubstituted with a C1-C3 alkylsulfonyl group, or
 a carboxyl group.

12. The compound 6-[4-Methoxy-2-methyl-3-(3,3,6,6-tetramethyl-1,8-dioxo-2,3,4,5,6,7,8,9-octahydro-1H-xanthen-9-yl)phenyl]pyridine-2-carboxylic acid, represented by the following formula:

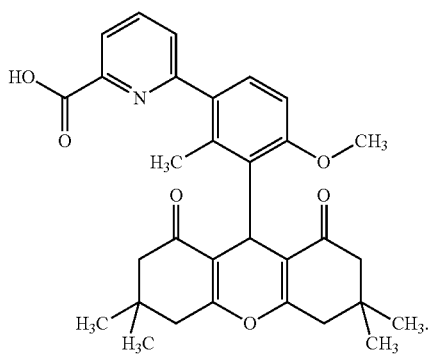 [SMILES: COc1ccc(-c2cccc(C(=O)O)n2)c(C)c1C1C2=C(CC(C)(C)CC2=O)OC2=C1C(=O)CC(C)(C)C2]

13. The compound 3-Ethyl-6-[4-methoxy-2-methyl-3-(3,3,6,6-tetramethyl-1,8-dioxo-2,3,4,5,6,7,8,9-octahydro-1H-xanthen-9yl)phenyl]pyridine-2-carboxylic acid, represented by the following formula:

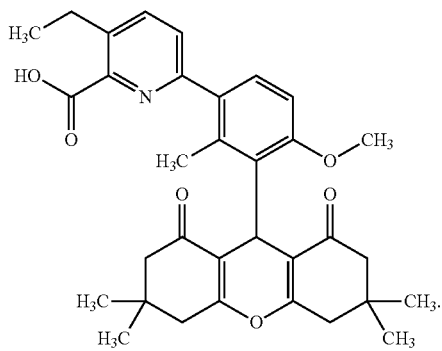 [SMILES: CCc1ccc(-c2ccc(OC)c(C3C4=C(CC(C)(C)CC4=O)OC4=C3C(=O)CC(C)(C)C4)c2C)nc1C(=O)O]

14. The compound 6-[4-Methoxy-2-methyl-3-(3,3,6,6-tetramethyl-1,8-dioxo-2,3,4,5,6,7,8,9-octahydro-1H-xanthen-9-yl)phenyl]-3-methylpyridine-2-carboxylic acid, represented by the following formula:

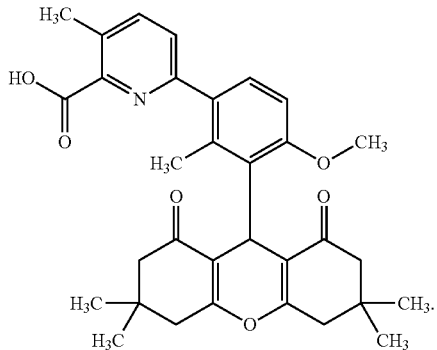 [SMILES: COc1ccc(-c2ccc(C)c(C(=O)O)n2)c(C)c1C1C2=C(CC(C)(C)CC2=O)OC2=C1C(=O)CC(C)(C)C2]

15. The compound 6-[4-Methoxy-2-methyl-3-(3,3,6,6-tetramethyl-1,8-dioxo-2,3,4,5,6,7,8,9-octahydro-1H-xanthen-9-yl)phenyl]-3-methyl-N-(methylsulfonyl)pyridine-2-carboxamide, represented by the following formula:

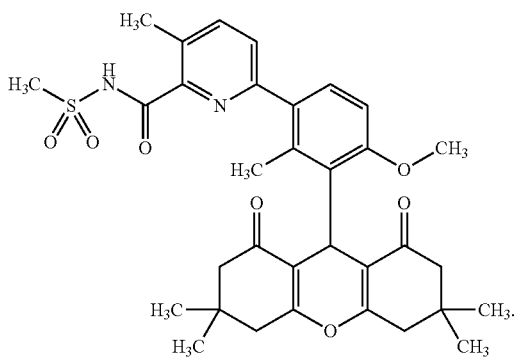 [SMILES: COc1ccc(-c2ccc(C)c(C(=O)NS(C)(=O)=O)n2)c(C)c1C1C2=C(CC(C)(C)CC2=O)OC2=C1C(=O)CC(C)(C)C2]

16. The compound 6-[4-Methoxy-2-methyl-3-(3,3,6,6-tetramethyl-1,8-dioxo-2,3,4,5,6,7,8,9-octahydro-1H-xanthen-9-yl)phenyl]-4-methylpyridine-2-carboxylic acid, represented by the following formula:

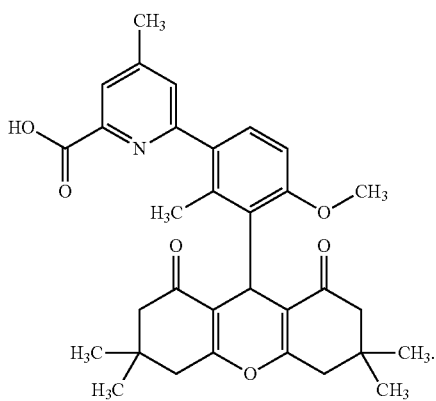 [SMILES: COc1ccc(-c2cc(C)cc(C(=O)O)n2)c(C)c1C1C2=C(CC(C)(C)CC2=O)OC2=C1C(=O)CC(C)(C)C2]

17. The compound 6-[4-Methoxy-2-methyl-3-(3,3,6,6-tetramethyl-1,8-dioxo-2,3,4,5,6,7,8,9-octahydro-1H-xanthen-9-yl)phenyl]-4-methyl-N-(methylsulfonyl)pyridine-2-carboxamide, represented by the following formula:

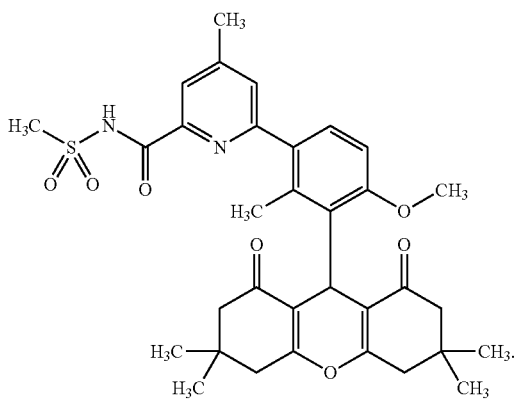 [SMILES: COc1ccc(-c2cc(C)cc(C(=O)NS(C)(=O)=O)n2)c(C)c1C1C2=C(CC(C)(C)CC2=O)OC2=C1C(=O)CC(C)(C)C2]

18. A pharmaceutical composition comprising the compound of claim 1 or a pharmacologically acceptable salt thereof, and a pharmaceutically acceptable agent.

19. A method of treating diabetes, postprandial hyperglycemia, impaired glucose tolerance, or insulin resistance, comprising administering a pharmacologically effective amount of the compound of claim 1 or a pharmacologically acceptable salt thereof to a warm-blooded animal.

20. The method of claim 19, wherein the diabetes is type II diabetes.

21. A pharmacologically acceptable salt of the compound of claim 15.

22. An alkali metal salt or an alkaline-earth metal salt of the compound of claim 15.

23. A hemi-calcium salt of the compound of claim 15.

24. A sodium salt of the compound of claim 15.

25. A 2-methylpropan-2-amine salt of the compound of claim 15.

26. A hemi-calcium salt of the compound of claim 17.

27. A sodium salt of the compound of claim 17.

28. A 2-methylpropan-2-amine salt of the compound of claim 17.

\* \* \* \* \*

UNITED STATES PATENT AND TRADEMARK OFFICE
CERTIFICATE OF CORRECTION

PATENT NO.        : 8,975,263 B2                              Page 1 of 1
APPLICATION NO.   : 14/291860
DATED             : March 10, 2015
INVENTOR(S)       : Shigeo Yamanoi et al.

It is certified that error appears in the above-identified patent and that said Letters Patent is hereby corrected as shown below:

In the Claims

In claim 7, in column 64, delete formula (II):

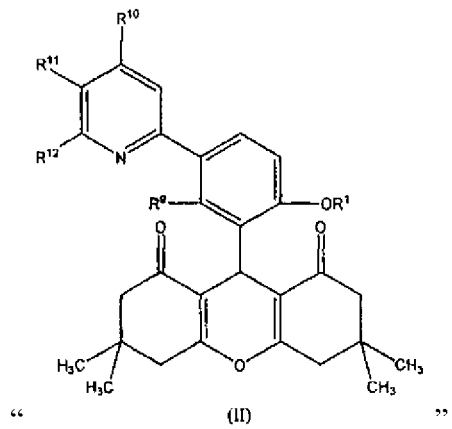

" (II) "

and insert therefor formula (II):

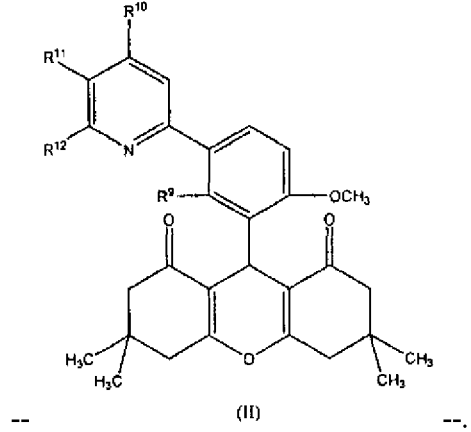

-- (II) --.

In claim 13, in column 65, line 21, delete "xanthen-9yl)phenyl]pyridine-2-carboxylic acid, represented" and insert therefor -- xanthen-9-yl)phenyl]pyridine-2-carboxylic acid, represented --.

Signed and Sealed this
Fourth Day of August, 2015

Michelle K. Lee
*Director of the United States Patent and Trademark Office*